(12) United States Patent
Boyle et al.

(10) Patent No.: US 6,414,145 B1
(45) Date of Patent: Jul. 2, 2002

(54) IMIDAZOLYL COMPOUNDS AS INHIBITORS OF FARNESYL-PROTEIN TRANFERASE

(75) Inventors: Francis Thomas Boyle; Gareth Morse Davies; James Michael Wardleworth, all of Macclesfield (GB); Jean-Claude Arnould, Reims Cedex (FR)

(73) Assignees: Zeneca Limited (GB); Zeneca Pharma S.A. (FR)

( * ) Notice: Subject to any disclaimer, the term of this patent is extended or adjusted under 35 U.S.C. 154(b) by 0 days.

(21) Appl. No.: 09/355,440

(22) PCT Filed: Jan. 27, 1998

(86) PCT No.: PCT/GB98/00230

§ 371 (c)(1),
(2), (4) Date: Jul. 28, 1999

(87) PCT Pub. No.: WO98/32741

PCT Pub. Date: Jul. 30, 1998

(30) Foreign Application Priority Data

Jan. 29, 1997 (EP) ............................................. 97400207

(51) Int. Cl.$^7$ .................... C07D 233/61; C07D 233/64; C07D 401/12; C07D 417/06; C07D 409/12; C07D 413/12; A61K 31/415
(52) U.S. Cl. ................. 544/139; 514/235.8; 514/236.8; 514/326; 514/341; 514/342; 514/365; 514/399; 514/400; 546/209; 546/210; 546/269.7; 546/275.1; 548/204; 548/338.1
(58) Field of Search ............................. 548/338.1, 204; 546/209, 210, 269.7, 275.1; 514/399, 400, 365, 341, 390, 326, 235.8, 236.8; 544/139

(56) References Cited

U.S. PATENT DOCUMENTS

| | | | | |
|---|---|---|---|---|
| 5,238,922 A | * | 8/1993 | Graham et al. | 514/18 |
| 5,326,773 A | * | 7/1994 | De Solms et al. | 514/336 |
| 5,340,828 A | * | 8/1994 | Graham et al. | 514/357 |
| 5,352,705 A | * | 10/1994 | Deana et al. | 514/630 |
| 5,534,537 A | * | 7/1996 | Ciccarone et al. | 514/397 |

FOREIGN PATENT DOCUMENTS

| | | | |
|---|---|---|---|
| WO | 95-25086 | * | 9/1995 |
| WO | 99-41235 | * | 8/1999 |

* cited by examiner

*Primary Examiner*—Floyd D. Higel
(74) *Attorney, Agent, or Firm*—Finnegan, Henderson, Farabow, Garrett & Dunner

(57) ABSTRACT

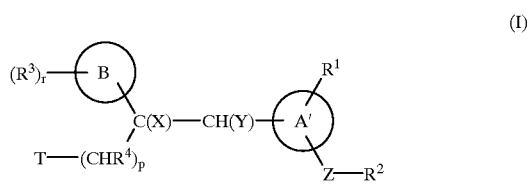

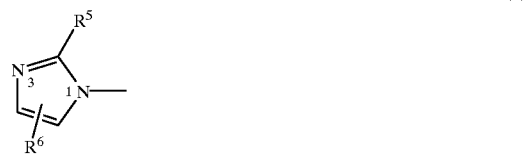

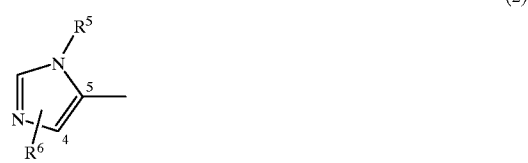

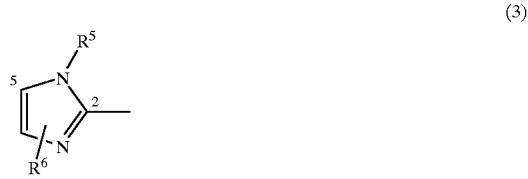

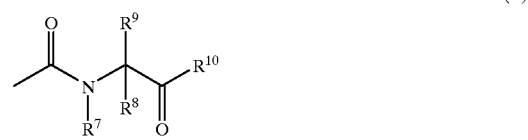

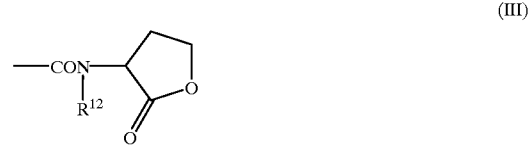

The present invention relates to inhibitors of ras farnesylation of Formula (I), wherein T is of Formula (1) or (2) or (3); A is aryl or heteroaryl; B is aryl or heteroaryl; X and Y represent hydrogen, or both X and Y can represent a single bond (so as to form a double bond); $R^1$ represents a group of Formula (II) or (III), the group of Formula (II) or Formula (III) (having L or D configuration at the chiral alpha carbon in the corresponding free amino acid); $R^2$ represents hydrogen, aryl or heteroaryl; Z represents a direct bond, methylene, ethylene, vinylene, oxy, —$CH_2$—O— or —O—$CH_2$—; and $R^3$—$R^4$, p and r are as defined in the specification or a pharmaceutically-acceptable salt, prodrug or solvate thereof. Processes for their preparation, their use as therapeutic agents and pharmaceutical compositions containing them. A particular use is in cancer therapy.

32 Claims, No Drawings

IMIDAZOLYL COMPOUNDS AS INHIBITORS OF FARNESYL-PROTEIN TRANFERASE

This application is a 35 U.S.C. §371 national stage application of PCT/GB 98/00230 filed on Jan. 27, 1998. This invention relates to compounds that inhibit farnesylation of mutant ras gene products through inhibition of the enzyme farnesyl-protein transferase (FPTase). The invention also relates to methods of manufacturing the compounds, pharmaceutical compositions and methods of treating diseases, especially cancer, which are mediated through farnesylation of ras.

This invention relates to compounds that inhibit farnesylation of mutant ras gene products through inhibition of the enzyme farnesyl-protein transferase (FPTase). The invention also relates to methods of manufacturing the compounds, pharmaceutical compositions and methods of treating diseases, especially cancer, which are mediated through farnesylation of ras.

Cancer is believed to involve alteration in expression or function of genes controlling cell growth and differentiation. Whilst not wishing to be bound by theoretical considerations the following text sets out the scientific background to ras in cancer. Ras genes are frequently mutated in tumours. Ras genes encode guanosine triphosphate (GTP) binding proteins which are believed to be involved in signal transduction, proliferation and malignant transformation. H-, K- and N-ras genes have been identified as mutant forms of ras (Barbacid M, Ann. Rev. Biochem. 1987, 56: 779–827). Post translational modification of ras protein is required for biological activity. Farnesylation of ras catalysed by FPTase is believed to be an essential step in ras processing. It occurs by transfer of the farnesyl group of farnesyl pyrophosphate (FPP) to a cysteine at the C-terminal tetrapeptide of ras in a structural motif called the CAAX box. After further post-translational modifications, including proteolytic cleavage at the cysteine residue of the CAAX box and methylation of the cysteine carboxyl, ras is able to attach to the cell membrane for relay of growth signals to the cell interior. In normal cells activated ras is believed to act in conjunction with growth factors to stimulate cell growth. In tumour cells it is believed that mutations in ras cause it to stimulate cell division even in the absence of growth factors (Travis J, Science 1993, 260: 1877–1878), possibly through being permanently in GTP activated form rather than cycled back to GDP inactivated form. Inhibition of farnesylation of mutant ras gene products will stop or reduce activation.

One class of known inhibitors of farnesyl transferase is based on farnesyl pyrophosphate analogues; see for example European patent application EP 534546 from Merck. Inhibitors of farnesyl transferase based on mimicry of the CAAX box have been reported. Reiss (1990) in Cell 62, 81–8 disclosed tetrapeptides such as CVIM (Cys-Val-Ile-Met). James (1993) in Science 260, 1937–1942 disclosed benzodiazepine based peptidomimetic compounds. Lerner (1995) in J. Biol. Chem. 270, 26802 and Eisai in International Patent Application WO 95/25086 disclosed further peptidomimetic compounds based on Cys as the first residue. Bristol-Myers Squibb in European Patent Application EP 696593 disclosed farnesyl transferase inhibitors having a 4-sulfanylpyrrolidine residue in the first position.

According to one aspect of the present invention there is provided an inhibitor of ras farnesylation of Formula I:

Formula I

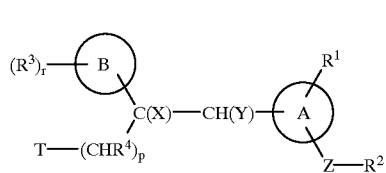

wherein T is of the formula:

(1)

or (2)

or (3)

;

A is aryl or heteroaryl;
B is aryl or heteroaryl;
X and Y represent hydrogen, or both X and Y can represent a single bond (so as to form a double bond);
$R^1$ represents a group of the Formula II:

Formula II

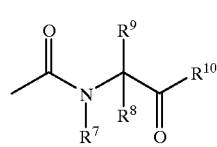

wherein $R^7$ is hydrogen or $C_{1-4}$alkyl, $R^8$ is hydrogen or $C_{1-4}$alkyl, $R^9$ is of the formula —$(CH_2)_q$—$R^{11}$ where q is 0–4 and $R^{11}$ is $C_{1-4}$alkylsulfanyl, $C_{1-4}$alkylsulfinyl, $C_{1-4}$alkylsulfonyl, hydroxy, amino, $C_{1-4}$alkoxy, carbamoyl, N-($C_{1-4}$alkyl)carbamoyl, N-(di$C_{1-4}$alkyl)carbamoyl, $C_{1-4}$alkyl, phenyl, thienyl, or $C_{1-4}$alkanoylamino, $R^{10}$ is hydroxy, amino, heterocyclyl$C_{1-4}$alkoxy, heterocyclalkyloxy, $C_{1-4}$alkoxy, $C_{5-7}$cycloalkyl$C_{1-4}$alkoxy or —NH—$SO_2$—$R^{13}$ wherein $R^{13}$ represents $CF_3$, $C_{1-4}$alkyl, aryl, heteroaryl, aryl$C_{1-4}$alkyl or heteroaryl$C_{1-4}$alkyl or $R^1$ represents a lactone of Formula III:

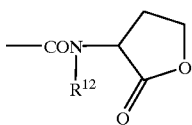

Formula III where $R^{12}$ is hydrogen or $C_{1-4}$alkyl;

the group of Formula II or III (having L or D configuration at the chiral alpha carbon in the corresponding free amino acid);

$R^2$ represents hydrogen, aryl or heteroaryl;

Z represents a direct bond, methylene, ethylene, vinylene, oxy, —$CH_2$—O— or —O—$CH_2$—;

$R^3$ represents hydrogen, $C_{1-4}$alkyl, halogen, hydroxy, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, carbamoyl, $C_{1-4}$alkoxycarbonyl, thiol, $C_{1-4}$alkylsulfanyl, $C_{1-4}$alkylsulfinyl, $C_{1-4}$alkylsulfonyl, aminosulfonyl, carbamoyl$C_{1-4}$alkyl, N-($C_{1-4}$alkyl)carbamoyl$C_{1-4}$alkyl, N-(di$C_{1-4}$alkyl)carbamoyl-$C_{1-4}$alkyl, hydroxy$C_{1-4}$alkyl and $C_{1-4}$alkoxy$C_{1-4}$alkyl;

r is 0–3 and $R^3$ can have the same or different values when r is 2–3;

$R^4$ is hydrogen or $C_{1-4}$alkyl; $R^5$ is hydrogen, $C_{1-4}$alkyl or aryl$C_{1-4}$alkyl; and $R^6$ is hydrogen, $C_{1-4}$alkyl, hydroxy$C_{1-4}$alkyl, aryl$C_{1-4}$alkyl, sulfanyl$C_{1-4}$alkyl, amino$C_{1-4}$alkyl or $C_{1-4}$alkylaminoalkyl;

p is 0–3 and $R^4$ can have the same or different values when p is 2–3;

or a pharmaceutically acceptable salt, prodrug or solvate thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting FTPase. The synthesis of optically active forms may be carried out by standard techniques of organic chemistry well known in the art, for example by synthesis from optically active starting materials or by resolution of a racemic form. Similarly, inhibitory properties against FTPase may be evaluated using the standard laboratory techniques referred to hereinafter.

The term "aryl" refers to phenyl or naphthyl. The term "heteroaryl" refers to a 5–10 membered monocyclic or bicyclic heteroaryl ring containing upto 5 heteroatoms selected from O, N and S. An aryl or heteroaryl ring in $R^2$, $R^5$, $R^6$ or $R^{13}$ is optionally mono- or di-substituted with substituents independently selected from $C_{1-4}$alkyl, halogen, hydroxy, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, carbamoyl, $C_{1-4}$alkoxycarbonyl, thiol, $C_{1-4}$alkylsulfanyl, $C_{1-4}$alkylsulfinyl, $C_{1-4}$alkylsulfonyl, $C_{1-4}$alkylsulfonamido, carbamoyl$C_{1-4}$alkyl, N-($C_{1-4}$alkyl)carbamoyl$C_{1-4}$alkyl, N-(di$C_{1-4}$alkyl)carbamoyl-$C_{1-4}$alkyl, hydroxy$C_{1-4}$alkyl and $C_{1-4}$alkoxy$C_{1-4}$alkyl. Bicyclic aryl and bicyclic heteroaryl rings refer to ring systems in which both rings of the bicyclic system are aromatic.

The term heterocyclyl refers to a 5- ro 6-membered monocyclic ring containing 1 to 3 heteroatoms selected from nitrogen, oxygen and sulfur.

The term "halogen" refers to fluorine, chlorine, bromine and iodine. The term "carbamoyl" refers to —C(O)$NH_2$. The term "BOC" refers to tert-butyl-O—C(O)—.

Examples of $C_{1-4}$alkyl include methyl, ethyl, propyl, isopropyl, sec-butyl and tert-butyl; examples of $C_{1-4}$alkoxy include methoxy, ethoxy and propoxy; examples of $C_{1-4}$alkanoyl include formyl, acetyl and propionyl; examples of $C_{1-4}$alkanoyloxy include acetyloxy and propionyloxy, examples of $C_{1-4}$alkylamino include methylamino, ethylamino, propylamino, isopropylamino, sec-butylamino and tert-butylamino; examples of di-($C_{1-4}$alkyl)amino include di-methylamino, di-ethylamino and N-ethyl-N-methylamino; examples of $C_{1-4}$alkanoylamino include acetamido and propionylamino; examples of $C_{1-4}$alkoxycarbonyl include methoxycarbonyl, ethoxycarbonyl and propoxycarbonyl; examples of $C_{1-4}$alkylsulfanyl include methylsulfanyl, ethylsulfanyl, propylsulfanyl, isopropylsulfanyl, sec-butylsulfanyl and tert-butylsulfanyl; examples of $C_{1-4}$alkylsulfinyl include methylsulfinyl, ethylsulfinyl, propylsulfinyl, isopropylsulfinyl, sec-butylsulfinyl and tert-butylsulfinyl; examples of $C_{1-4}$alkylsulfonyl include methylsulfonyl, ethylsulfonyl, propylsulfonyl, isopropylsulfonyl, sec-butylsulfonyl and tert-butylsulfonyl; examples of carbamoyl$C_{1-4}$alkyl include carbamoylmethyl, carbamoylethyl and carbamoylpropyl; examples of N-($C_{1-4}$alkyl)carbamoyl$C_{1-4}$alkyl include N-methyl-carbamoylmethyl and N-ethyl-carbamoylethyl; examples of N-(di$C_{1-4}$alkyl)carbamoyl-$C_{1-4}$alkyl include N,N-dimethylcarbamoylethyl and N-methyl-N-ethylcarbamoylethyl; examples of hydroxy$C_{1-4}$alkyl include hydroxymethyl, hydroxyethyl, hydroxypropyl, 2-hydroxypropyl, 2-(hydroxymethyl)propyl and hydroxybutyl; examples of $C_{1-4}$alkoxy$C_{1-4}$alkyl include methoxyethyl, ethoxyethyl and methoxybutyl; examples of sulfanyl$C_{1-4}$alkyl include sulfanylmethyl, sulfanylethyl, sulfanylpropyl; and examples of N-($C_{1-4}$alkyl)amino$C_{1-4}$alkyl include N-methyl-aminomethyl and N-ethyl-aminoethyl.

Examples of 5–10 membered monocyclic or bicyclic heteroaryl rings containing upto 5 heteroatoms selected from O, N and S include the following. Examples of 5- or 6-membered heteroaryl ring systems include imidazole, triazole, pyrazine, pyrimidine, pyridazine, pyridine, isoxazole, oxazole, isothiazole, thiazole and thiophene. A 9 or 10 membered bicyclic heteroaryl ring system is an aromatic bicyclic ring system comprising a 6-membered ring fused to either a 5 membered ring or another 6 membered ring. Examples of 5/6 and 6/6 bicyclic ring systems include benzofuran, benzimidazole, benzthiophene, benzthiazole, benzisothiazole, benzoxazole, benzisoxazole, pyridoimidazole, pyrimidoimidazole, quinoline, isoquinoline, quinoxaline, quinazoline, phthalazine, cinnoline and naphthyridine.

Preferably monocyclic heteroaryl rings contain upto 3 heteroatoms and bicyclic heteroaryl rings contain upto 5 heteroatoms. Preferred heteroatoms are N and S, especially N. In general, attachment of heterocyclic rings to other groups is via carbon atoms. Suitable values of heterocycles containing only N as the heteroatom are pyrrole, pyridine, indole, quinoline, isoquinoline, imidazole, pyrazine, pyrimidine, purine and pteridine.

Examples of heterocyclyl rings include pyrrolidinyl, morpholinyl, piperidinyl, dihydropyridinyl and dihydropyrimidinyl.

Preferred heteroatoms are N and S, especially N. In general, attachment of heterocyclic rings to other groups is via carbon atoms.

Examples values for $R^9$ in Formula II are side chains of lipophilic amino acids including such as for example methionine, phenylglycine, phenylalanine, serine, leucine, isoleucine or valine. L configuration in the corresponding free amino acid is preferred. Examples of amino acid side chains are set out below.

| Amino Acid | Side Chain |
|---|---|
| methionine | —$CH_2$—$CH_2$—S—$CH_3$ |
| phenylglycine | phenyl |
| phenylalanine | benzyl |
| thienylalanine | thien-2-ylmethyl |
| serine | —$CH_2OH$ or a $C_{1-4}$alkyl (preferably methyl) ether thereof. |
| leucine | —$CH_2$—$CHMe_2$ |
| homoserine | —$CH_2$—$CH_2$—OH or a $C_{1-4}$alkyl (preferably methyl) ether thereof |
| N-acetyl-lysine | —$CH_2$—$CH_2$—$CH_2$—$CH_2$—NH—CO—$CH_3$ |

The lactone in Formula III can be formed from a group of Formula II when $R^{10}$ is hydroxy to give a carboxy group and $R^9$ is —$CH_2$—$CH_2$—OH where $R^9$ and $R^{10}$ together lose a water molecule to form part of a dihydrofuran-2-one heterocyclic ring.

Preferably T is imidazol-1-yl or imidazol-5-yl. Most preferably T is imidazol-1-yl. Preferably, $R^5$ is hydrogen, methyl or cyanobenzyl. $R^6$ is preferably hydrogen, hydroxy$C_{1-4}$alkyl, cyanobenzyl, sulfanyl$C_{1-4}$alkyl or N-($C_{1-4}$alkyl)amino$C_{1-4}$alkyl. More preferably $R^6$ is hydrogen, methyl or hydroxy$C_{1-4}$alkyl, and especially hydroxymethyl.

Preferably $R^4$ is hydrogen or methyl. Most preferably $R^4$ is hydrogen.

Preferably p is 1–3. More preferably p is 1–2. Most preferably p is 1.

$R^3$ is preferably hydrogen or fluoro.

When B is phenyl then $R^3$ is preferably fluoro, particularly mono-substituted (r=1) and especially mono-substituted in the para position.

When B is heteroaryl (especially thiazolyl), $R^3$ is preferably hydrogen.

A preferred aryl value for B is phenyl. A preferred heteroaryl value for B is thiazolyl, especially thiazol-2-yl.

A preferred value for X and Y is a direct bond (so as to form a double bond). Preferably rings A and B are on the same side of the double bond containing X and Y (this will give either E or Z isomeric configuration depending on the substituents). A is preferably a 6-membered aryl or heteroaryl ring. Most preferably A is phenyl.

In one aspect of the invention, $R^2$ is preferably aryl or heteroaryl, preferably a 6-membered ring, more preferably aryl, and especially phenyl. When Z is a direct bond and A is phenyl, A is preferably substituted by $R^1$ in the 4-position and —$ZR^2$ in the 3- or the 5-position. When Z is not a direct bond and A is phenyl, A is preferably substituted by $R^1$ in either the 3- or 5-position and —$ZR^2$ in the 4-position.

In another aspect of the invention $R^2$ is hydrogen. In another aspect of the invention $R^2$ is preferably aryl or heteroaryl. More preferably $R^2$ is phenyl or monocyclic heteroaryl. Most preferably $R^2$ is phenyl, thienyl or pyridyl.

When $R^2$ is heteroaryl it is preferably unsubstituted.

When $R^2$ is phenyl it is preferably unsubstituted or mono-substituted by fluoro.

Preferably Z is a direct bond, methylene or ethylene.

Particular values for —Z—$R^2$ are hydrogen, phenyl, 4-fluorophenyl, 2-(4-fluorophenyl)ethyl, thienyl or pyridyl.

$R^1$ is preferably a group of Formula II. More preferably $R^1$ has the following configuration:

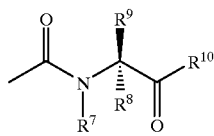

$R^7$ is preferably hydrogen. $R^8$ is preferably hydrogen or methyl, especially hydrogen. In $R^9$, q is preferably 1–4, more preferably 1–3, more preferably 2–3 and especially 2. Within $R^9$, $R^{11}$ is preferably $C_{1-4}$alkylsulfanyl, $C_{1-4}$alkylsulfinyl, $C_{1-4}$alkylsulfonyl, hydroxy, thienyl or carbamoyl, more preferably methylsulfanyl or carbamoyl. Most preferably $R^{11}$ is methylsulfanyl. In another aspect of the invention $R^9$ is thien-2-ylmethyl, or acetamidobutyl.

$R^{10}$ is preferably hydroxy, $C_{1-4}$alkoxy, heterocyclyloxy, heterocyclylalkoxy, amino or of the formula —$NHSO_2R^{13}$ wherein $R^{13}$ is $CF_3$, $C_{1-4}$alkyl, aryl, heteroaryl or aryl$C_{1-4}$alkyl.

More preferably $R^{10}$ is hydroxy, methoxy tert-butoxy, piperidin-4yloxy, 3-(morpholino)propan-2-yloxy, 1-methylpiperidin-4-yloxy, amino or of the formula —$NHSO_2R^{13}$ wherein $R^{13}$ is methyl, 4-chlorophenyl, benzyl, trifluoromethyl or 3,5-dimethylisoxaol-4-yl.

Most preferably $R^{10}$ is hydroxy or tert-butoxy.

A preferred class of compounds is of the formula (I) wherein:
A is phenyl;
>C(X)—CH(Y)— is >C=CH—;
$R^4$ is hydrogen;
p is 1;
and $R^1$—$R^3$, r, B, T and Z are as hereinabove defined;
and a pharmaceutically-acceptable salt, prodrug or solvate thereof.

A more preferred class of compound is of the formula (I) wherein:
A is phenyl;
>C(X)—CH(Y)— is >C=CH—;
$R^4$ is hydrogen;
p is 1;
T is of the formula (1) or (2);
and $R^1$—$R^3$, $R^5$, $R^6$, r, B and Z are as hereinabove defined;

and a pharmaceutically-acceptable salt, prodrug or solvate thereof.

A yet more preferred class of compound is of the formula (I) wherein:
A is phenyl;
>C(X)—CH(Y)— is >C=CH—;
p is 1;
T is of the formula (1) or (2);
B—($R^3$)r is thiazolyl or 4-fluorophenyl; and $R^1$, $R^2$, $R^5$, $R^6$ and Z are as hereinabove defined;
and a pharmaceutically-acceptable salt, prodrug or solvate thereof.

A yet more preferred class of compound is of the formula (I) wherein:
A is phenyl;
>C(X)—CH(Y)— is >C=CH—;
$R^4$ is hydrogen;
p is 1;
T is of the formula (1) or (2);
—B—($R^3$)r is thiazolyl or 4-fluorophenyl;
—Z—$R^2$ is hydrogen, phenyl, 4-fluorophenyl, 2-(4-fluorophenyl)ethyl, thienyl or pyridyl;
and $R^1$, $R^5$ and $R^6$ are as hereinabove defined;
and a pharmaceutically-acceptable salt, prodrug or solvate thereof.

The most preferred class of compounds is of the formula (I) wherein:
A is phenyl;
>C(X)—CH(Y)— is >C=CH—;
$R^4$ is hydrogen;
p is 1;
T is of the formula (1) or (2);
$R^5$ is hydrogen, methyl or cyanobenzyl; $R^6$ is hydrogen, methyl or hydroxy$C_{1-4}$alkyl;
$R^5$ is hydrogen, methyl, hydroxy$C_{1-4}$alkyl, cyanobenzyl, sulfanyl$C_{1-4}$alkyl or N-($C_{1-4}$alkyl)amino $C_{1-4}$alkyl) amino$C_{1-4}$alkyl;
$R^6$ is hydrogen or methyl;
—B—($R^3$)r is thiazolyl or 4-fluorophenyl;
—Z—$R^2$ is hydrogen, phenyl, 4-fluorophenyl, 2-(4-fluorophenyl)ethyl, thienyl or pyridyl; and
$R^1$ is of the formula (II) wherein $R^7$ is hydrogen, $R^8$ is hydrogen or methyl; $R^9$ is of the formula —(CH)$_q$—$R^{11}$ wherein q is 1–4;
$R^{11}$ is $C_{1-4}$alkylsulfanyl, $C_{1-4}$alkylsulfinyl, $C_{1-4}$alkylsulfonyl, hydroxy, thienyl or carbamoyl; and $R^{10}$ is hydroxy, $C_{1-4}$alkoxy, heterocycloxy, heterocyclyl$C_{1-4}$alkoxy, amino or of the formula —NHSO$_2$$R^{13}$ wherein $R^{13}$ is CF$_3$, $C_{1-4}$alkyl, aryl, heteroaryl or aryl$C_{1-4}$alkyl; and a pharmaceutically-acceptable salt, prodrug or solvate thereof.

Preferred individualised compounds of the invention are as follows:

(2S)-2-{4-[(E)-2-(4-fluorophenyl)-3-(5-methylimidazol-1-yl)-prop-1-enyl]-2-phenylbenzamido}-4-methylsulfanylbutyric acid;
(2S)-2-{4-[2-(4-fluorophenyl)-3-(5-methylimidazol-1-yl)-propyl]-2-phenyl-benzamido}-4-methylsulfanylbutyric acid;
(2S)-2-{3-[(E)-2-(4-fluorophenyl)-3-(imidazol-1-yl)-prop-1-enyl]-benzamido}-4-methylsulfanylbutyric acid;
(2S)-2-{4-[(Z)-3-(imidazol-1-yl)-2-(thiazol-2-yl)-prop-1-enyl]-2-phenyl-benzamido}-4-methylsulfanylbutyric acid;
(2S)-2-{3-[(E)-2-(4-fluorophenyl)-3-(imidazol-1-yl)-prop-1-enyl]-benzamido}-4-carbamoylbutyric acid;
(2S)-2-{3-[(E)-2-(4-fluorophenyl)-3-(imidazol-1-yl)-prop-1-enyl]-benzamido}-4-methylsulfanyl-N-(trifluoromethylsulfonyl)-butanamide;
(2S)-2-{3-[(Z)-2-(4-fluorophenyl)-4-(imidazol-1-yl)-but-1-enyl]-benzamido}-4-methylsulfanylbutyric acid;
(2S)-2-{3-[(E)-2-(4-fluorophenyl)-3-(imidazol-1-yl)-prop-1-enyl]-benzamido}-4-hydroxybutyric acid;
(2S)-2-{3-[(Z)-2-(4-fluorophenyl)-3-(imidazol-1-yl)-prop-1-enyl]-benzamido}-4-methylsulfanylbutyric acid;
(2S)-2-{3-[(E)-2-(4-fluorophenyl)-3-(imidazol-1-yl)-prop-1-enyl]-benzamido}-4-methylsulfonylbutyric acid;
(2S)-2-{4-[(E)-2-(4-fluorophenyl)-3-(5-methylimidazol-1-yl)-prop-1-enyl]-2-phenylbenzamido}-4-carbamoylbutyric acid;
(2S)-2-{3-[(Z)-3-(imidazol-1-yl)-2-(thiazol-2-yl)-prop-1-enyl]-benzamido}-4-carbamoylbutyric acid;
(2S)-2-{3-[(E)-2-(4-fluorophenyl)-3-(5-methylimidazol-1-yl)-prop-1-enyl]-benzamido}-4-methylsulfanylbutyric acid;
(2S)-2-{3-[(Z)-3-(imidazol-1-yl)-2-(thiazol-2-yl)prop-1-enyl]-benzamido}-4-methylsulfanylbutyric acid;
methyl (2S)-2-{3-[(E)-2-(4-fluorophenyl)-3-(imidazol-1-yl) prop-1-enyl]-benzamido}-4-methylsulfanylbutanoate;
tert-butyl (2S)-2-{3-[(E)-2-(4-fluorophenyl)-3-(imidazol-1-yl)-prop-1-enyl]-benzamido}-4-carbamoylbutanoate;
(2S)-2-{4-[(Z)-3-(imidazol-1-yl)-2-(thiazol-2-yl)-prop-1-enyl]-2-phenyl-benzamido}-4-carbamoylbutyric acid;
(2S)-2-{3-[(E)-2-(4-fluorophenyl)-4-(imidazol-1-yl)-but-1-enyl]-benzamido}-4-methylsulfanylbutyric acid;
(2S)-2-{4-[(E)-2-(4-fluorophenyl)-3-(imidazol-1-yl)-prop-1-enyl]-benzamido}-4-carbamoylbutyric acid;
methyl (2S)-2-{4-[(E)-2-(4-fluorophenyl)-3-(5-methylimidazol-1-yl)-prop-1-enyl]-2-phenylbenzamido}-4-methylsulfanylbutanoate;
(2S)-2-{4-[(E)-2-(4-fluorophenyl)-3-(imidazol-1-yl)prop-1-enyl]-2-phenyl-benzamido}-4-methylsulfanylbutyric acid;
methyl (2S)-2-{4-[(E)-2-(4-fluorophenyl)-3-(imidazol-1-yl) prop-1-enyl]-2-phenyl-benzamido}-4-methylsulfanylbutyrate;
(2S)-2-{4-[(E)-2-(4-fluorophenyl)-3-(imidazol-1-yl)prop-1-enyl]-2-(4-fluorophenyl)benzamido}-4-methylsulfanylbutyric acid;
methyl (2S)-2-{4-[(E)-2-(4-fluorophenyl)-3-(imidazol-1-yl) prop-1-enyl]-2-(4-fluorophenyl)benzamido}-4-methylsulfanylbutyrate;
t-butyl (2S)-2-{4-[(E)-2-(4-fluorophenyl)-3-(imidazol-1-yl) prop-1-enyl]-2-(4-fluorophenyl)-benzamido}-4-methylsulfanylbutyrate;
(2S)-2-{4-[(E)-2-(4-fluorophenyl)-3-(imidazol-1-yl)prop-1-enyl]-2-(4-fluorophenyl)-benzamido}-4-methylsulfonylbutyric acid;
methyl (2S)-2-{4-[(E)-2-(4-fluorophenyl)-3-(imidazol-1-yl) prop-1-enyl]-2-(4-fluorophenyl)benzamido}-4-methylsulfonylbutyrate;
t-butyl(2S)-2-{4-[(E)-2-(4-fluorophenyl)-3-(imidazol-1-yl) prop-1-enyl]-2-(4-fluorophenyl)benzamido}-4-methylsulfonylbutyrate;

(2S)-2-{4-[(E)-2-(4-fluorophenyl)-3-(imidazol-1-yl)prop-1-enyl]-2-(4-fluorophenyl)-benzamido}-4-methylsulfinylbutyric acid;
methyl (2S)-4-{3-[(E)-2-(4-fluorophenyl)-3-(imidazol-1-yl)prop-1-enyl]-2-(4-fluorophenyl)benzamido}-4-methylsulfinylbutyrate;
N-methylpiperidin-4-yl (2S)-2-{4-[(E)-2-(4-fluorophenyl)-3-(imidazol-1-yl)prop-1-enyl]-2-(4-fluorophenyl)benzamido}-4-methylsulfanylbutyrate;
1-(morpholin-4-yl)prop-2-yl-(2S)-2-{4-[(E)-2-(4-fluorophenyl)-3-(imidazol-1-yl)prop-1-enyl]-benzamido}-4-methylsulfanylbutyrate;
(2S)-2-{4-[(Z)-2-(thiazol-2-yl)-3-(imidazol-1-yl)prop-1-enyl]-2-(4-fluorophenyl)-benzamido}-4-methylsulfanylbutyric acid;
methyl (2S)-4-{[(Z)-2-(thiazol-2-yl)-3-(imidazol-1-yl)prop-1-enyl]-2-(4-fluorophenyl)benzamido}-4-methylsulfanylbutyrate;
tert-butyl(2S)-2-{4-[(Z)-2-(thiazol-2-yl)-3-(imidazol-1-yl)prop-1-enyl]-2-(4-fluorophenyl)benzamido}-4-methylsulfanylbutyrate;
(2S)-2-{4-[(Z)-2-(thiazol-2-yl)-3-(imidazol-1-yl)prop-1-enyl]-2-(4-fluorophenyl)-benzamido}-4-methylsulfonylbutyric acid;
methyl (2S)-2-{4-[(Z)-2-(thiazol-2-yl)-3-(imidazol-1-yl)prop-1-enyl]-2-(4-fluorophenylbenzamido}-4-methylsulfonylbutyrate;
tert-butyl (2S)-2-{4-[(Z)-2-(thiazol-2-yl)-3-(imidazol-1-yl)prop-1-enyl]-2-(4-fluorophenyl)benzamido}-4-methylsulfonylbutyrate;
N-methylpiperidin-4-yl (2S)-2-{4-[(Z)-2-(thiazol-2-yl)-3-(imidazol-1-yl)prop-1-enyl]-2-(4-fluorophenyl)benzamido}-4-methylsulfanylbutyrate;
(2S)-2-{4-[(Z)-2-(thiazol-2-yl)-3-(imidazol-1-yl)prop-1-enyl]-2-(thien-3-yl)benzamido}-4-methylsulfanylbutyric acid;
methyl (2S)-2-{4-[(Z)-2-(thiazol-2-yl)-3-(imidazol-1-yl)prop-1-enyl]-2-(thien-3-yl)benzamido}-4-methylsulfanylbutyrate;
methyl (2S)-2-{4-[(Z)-2-(thiazol-2-yl)-3-(imidazol-1-yl)prop-1-enyl]-2-(pyrid-3-yl)benzamido}-4-methylsulfanylbutyrate;
methyl (2S)-2-{4-[(Z)-2-(4-fluorophenyl)-3-(imidazol-1-yl)prop-1-enyl]-2-(pyrid-3-yl)benzamido}-4-methylsulfanylbutyric acid;
N-(3,5-dimethylisoxazol-4-ylsulfonyl)(2S)-2-{4-[(Z)-2-(4-fluorophenyl)-3-(imidazol-1-yl)prop-1-enyl]-2-(4-fluorophenyl}benzamido}-4-methylsulfanylbutyramide;
N-(4-chlorophenylsulfonyl)(2S)-2-{4-[(E)-2-(4-fluorophenyl)-3-(imidazol-1-yl)prop-1-enyl]-2-(4-fluorophenyl)benzamido}-4-methylsulfanylbutyramide;
(2S)-2-{4-[(E)-2-(4-fluorophenyl)-3-(imidazol-1-yl)prop-1-enyl]-2-(4-fluorophenyl)benzamido}-4-methylsulfanylbutyric acid;
methyl(2S)-2-{4-[(E)-2-(4-fluorophenyl)-3-(imidazol-1-yl)prop-1-enyl]-2-(4-fluorophenyl)benzamido}-4-methylsulfanylbutyrate;
N-benzylsulfonyl(2S)-2-{4-[(E)-2-(4-fluorophenyl)-3-(imidazol-1-yl)prop-1-enyl]-2-(4-fluorophenyl)benzamido}-4-methylsulfanylbutyramide;
(2S)-2-{4-[(E)-2-(4-fluorophenyl)-3-(imidazol-1-yl)prop-1-enyl]-2-(4-fluorophenyl)benzamido}propanoic acid;
methyl (2S)-2-{4-[(E)-2-(4-fluorophenyl)-3-(imidazol-1-yl)prop-1-enyl]-2-(4-fluorophenyl)benzamido}-4-propanoate;
(2S)-2-{4-[(Z)-2-(thiazol-2-yl)-3-(imidazol-1-yl)prop-1-enyl]-3-phenylbenzamido}-4-methylsulfanylbutyric acid;

methyl (2S)-2-{4-[(Z)-2-(thiazol-2-yl)-3-(imidazol-1-yl)prop-1-enyl]-3-phenylbenzamido}-4-methylsulfanylbutyrate;
(2S)-2-{4-[(E)-2-(4-fluorophenyl)-3-(imidazol-1-yl)prop-1-enyl]-2-(4-fluorophenyl)benzamido}-4-methylsulfanylbutyric acid;
methyl(2S)-2-{4-[(E)-2-(4-fluorophenyl)-3-(imidazol-1-yl)prop-1-enyl]-2-(4-fluorophenyl)benzamido}-4-methylsulfanylbutyrate;
(2S)-2-{5-[(E)-2-(4-fluorophenyl)-3-(imidazol-1-yl)prop-1-enyl]-2-(2-(4-fluorophenyl)ethyl)benzamido}-4-methylsulfanylbutyric acid;
methyl (2R)-2-{3-[(E)-2-(4-fluorophenyl)-3-(imidazol-1-yl)prop-1-enyl]benzamido}-4-methylsulfanylbutyrate;
methyl (2S)-2-{3-[(E)-2-(4-fluorophenyl)-3-(imidazol-1-yl)prop-1enyl]benzamido}-4-methylsulfanylbutyrate;
methyl (2S)-2-{3-[(R/S)-2-(4-fluorophenyl)-3-(imidazol-1-yl)prop-1-enyl]benzamido}-3-(thien-2-yl)propanoate
methyl (2S)-2-{3-[(E)-2-(4-fluorophenyl)-3-(imidazol-1-yl)prop-1-enyl]benzamido}-6-aminohexanoate;
(2S)-2-{3-[(E)-2-(4-fluorophenyl)-3-(imidazol-1-yl)prop-1-enyl]benzamido}-4-methylsulfanylbutyramide;
trifluoromethanesulfonyl (2S)-2-{3-[(E)-2-(4-fluorophenyl)-3-(imidazol-1-yl)prop-1-enyl]-benzamido}-4-methylsulfanylbutyramide;
methanesulfonyl (2S)-2-{3-[(E)-2-(4-fluorophenyl)-3-(imidazol-1-yl)prop-1-enyl]-benzamido}-4-methylsulfanylbutyramide; and
pharmaceutically acceptable salts thereof.

In another aspect the present invention provides an inhibitor of ras farnesylation of the Formula XI:

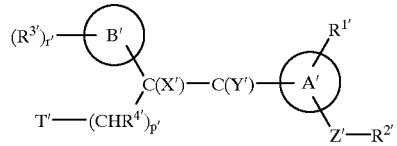

Formula XI wherein
T' represents

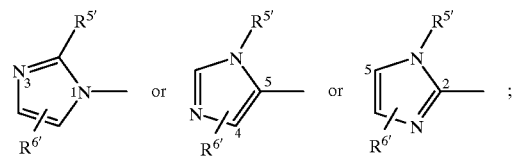

A' is aryl or heteroaryl;
B' is aryl or heteroaryl;
X' and Y' represent hydrogen, or both X' and Y' can represent a single bond (so as to form a double bond);
R¹' represents a group of the Formula XII

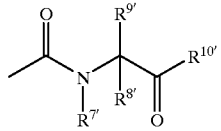

Formula XII a group of Formula XII, where $R^{7'}$ is H or $C_{1-4}$alkyl, $R^{8'}$ is H or $C_{1-4}$alkyl, $R^{9'}$ is selected from —$(CH_2)_{q'}$—

$R^{11'}$ where q' is 0–4 and $R^{11'}$ is $C_{1-4}$alkylsulfanyl, $C_{1-4}$alkylsulfinyl, $C_{1-4}$alkylsulfonyl, hydroxy, $C_{1-4}$alkoxy, carbamoyl, N-(mono$C_{1-4}$alkyl)carbamoyl, N-(di$C_{1-4}$alkyl)carbamoyl, $C_{1-4}$alkyl, phenyl, thienyl, or $C_{1-4}$alkanoylamino, $R^{10'}$ is hydroxy, $C_{1-4}$alkoxy, or —NH—$SO_2$—$R^{13'}$ wherein $R^{13'}$ represents $CF_3$, $C_{1-4}$alkyl, aryl or heteroaryl, or $R^{1'}$ represents a lactone of Formula XIII

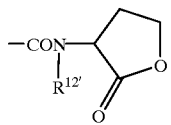

Formula XIII where $R^{12'}$ is H or $C_{1-4}$alkyl;

the group of Formula XII or XIII (having L or D configuration at the chiral alpha carbon in the corresponding free amino acid);

$R^{2'}$ represents hydrogen, aryl or heteroaryl;

Z' represents a direct bond, methylene, ethylene, vinylene, oxy, —$CH_2$—O— or —O—$CH_2$—;

$R^{3'}$ represents hydrogen, $C_{1-4}$alkyl, halogen, OH, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, carbamoyl, $C_{1-4}$alkoxycarbonyl, thiol, $C_{1-4}$alkylsulfanyl, $C_{1-4}$alkylsulfinyl, $C_{1-4}$alkylsulfonyl, sulfonamido, carbamoyl$C_{1-4}$alkyl, N-(mono$C_{1-4}$alkyl)carbamoyl$C_{1-4}$alkyl, N-(di$C_{1-4}$alkyl)carbamoyl-$C_{1-4}$alkyl, hydroxy$C_{1-4}$alkyl and $C_{1-4}$alkoxy$C_{1-4}$alkyl;

r' is 0–3 and $R^{3'}$ can have the same or different values when r' is 2–3;

$R^{4'}$, $R^{5'}$ and $R^{6'}$ independently represent hydrogen or $C_{1-4}$alkyl and, provided $R^{5'}$ is attached to carbon on the imidazole ring in T', then $R^{5'}$ can also represent hydroxy$C_{1-4}$alkyl, sulfanyl$C_{1-4}$alkyl, or N-(mono$C_{1-4}$alkyl)amino$C_{1-4}$alkyl;

p' is 0–3 and $R^{4'}$ can have the same or different values when p' is 2–3;

or an enantiomer, diastereoisomer, pharmaceutically acceptable salt, prodrug or solvate thereof.

Compounds of Formula I may form salts which are within the ambit of the invention. Pharmaceutically acceptable salts are preferred although other salts may be useful in, for example, isolating or purifying compounds.

When the compound contains a basic moiety it may form pharmaceutically acceptable salts with a variety of inorganic or organic acids, for example hydrochloric, hydrobromic, sulphuric, phosphoric, trifluoroacetic, citric or maleic acid. A suitable pharmaceutically-acceptable salt of the invention when the compound contains an acidic moiety is an alkali metal salt, for example a sodium or potassium salt, an alkaline earth metal salt, for example a calcium or magnesium salt, an ammonium salt or a salt with an organic base which affords a pharmaceutically-acceptable cation, for example a salt with methylamine, dimethylamine, trimethylamine, piperidine, morpholine or tris-(2-hydroxyethyl)amine.

Solvates, for example hydrates, are also within the ambit of the invention and may be prepared by generally known methods.

Various forms of prodrugs are well known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113–191 (1991);

c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

Examples of pro-drugs include in vivo hydrolysable esters of a compound of the Formula I. Suitable pharmaceutically-acceptable esters for carboxy include $C_{1-8}$alkyl esters, $C_{5-8}$cycloalkyl esters, cyclic amine esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl wherein alkyl, cycloalkyl and cylicamino groups are optionally substituted by, for example, aryl, heterocyclyl, alkyl, amino, alkylamino, dialkylamino, hydroxy, alkoxy, aryloxy or benzyloxy, and may be formed at any carboxy group in the compounds of this invention.

According to another aspect of the invention there is provided a pharmaceutical composition comprising a compound as defined in Formula I or an individual compound listed above together with a pharmaceutically acceptable diluent or carrier. A preferred pharmaceutical composition is in the form of a tablet.

The compositions of the invention may be in a form suitable for oral use (for example as tablets, lozenges, hard or soft capsules, aqueous or oily suspensions, emulsions, dispersible powders or granules, syrups or elixirs) for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, $30\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch: Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of ras.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used.

Similarly, for administration by inhalation, a dose in the range, for example, 0.5 mg to 25 mg per kg body weight will be used. Oral administration is however preferred.

Compounds of this invention may be useful in combination with known anti-cancer and cytotoxic agents. If formulated as a fixed dose such combination products employ the compounds of this invention within the dosage range described herein and the other pharmaceutically active agent within its approved dosage range. Sequential use is contemplated when a combination formulation is inappropriate. According to another aspect of the invention there is provided a compound of Formula I or a pharmaceutically-acceptable salt thereof, for use as a medicament.

Therefore in a further aspect, the present invention provides a compound of the Formula I or a pharmaceutically acceptable salt thereof for use in a method of therapeutic treatment of the human or animal body.

In yet a further aspect, the present invention provides a compound of the Formula I or a pharmaceutically acceptable salt thereof for use in treating a disease condition mediated through farnesylation of ras.

In yet a further aspect the present invention provides a method of treating a disease or medical condition mediated through farnesylation of ras which comprises administering to a warm-blooded animal an effective amount of a compound of the Formula I or a pharmaceutically acceptable salt thereof.

The present invention also provides the use of a compound of the Formula I or a pharmaceutically acceptable salt thereof in the preparation of a medicament for use in a disease condition mediated through farnesylation of ras.

In yet a further aspect, the present invention provides a compound of the Formula I or a pharmaceutically acceptable salt thereof in the preparation of a medicament for treating cancer.

Diseases or medical conditions may be mediated alone or in part by farnesylated ras. A particular disease of interest is cancer. Specific cancers of interest include:

carcinoma, including that of the bladder, breast, colon, kidney, liver, lung, ovary, pancreas, stomach, cervix, thyroid and skin;

hematopoietic tumors of lymphoid lineage, including acute lymphocytic leukemia, B-cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, tetratocarcinoma, neuroblastoma and glioma.

The compounds of Formula I are especially useful in treatment of tumors having a high incidence of ras mutation, such as colon, lung, and pancreatic tumors. By the administration of a composition having one (or a combination) of the compounds of this invention, development of tumors in a mammalian host is reduced.

Compounds of Formula I may also be useful in the treatment of diseases other than cancer that may be associated with signal transduction pathways operating through Ras, e.g., neuro-fibromatosis.

Compounds of Formula I may also be useful in the treatment of diseases associated with CAAX-containing proteins other than Ras (e.g., nuclear lamins and transducin) that are also post-translationally modified by the enzyme farnesyl protein transferase.

Although the compounds of the Formula I are primarily of value as therapeutic agents for use in warm-blooded animals (including man), they are also useful whenever it is required to inhibit the effects of activation of ras by farnesylation. Thus, they are useful as pharmacological standards for use in the development of new biological tests and in the search for new pharmacological agents.

In another aspect the present invention provides a process for preparing a compound of the Formula I or a pharmaceutically acceptable salt or in vivo hydrolysable ester thereof which process comprises:

reacting a compound of the Formula IV:

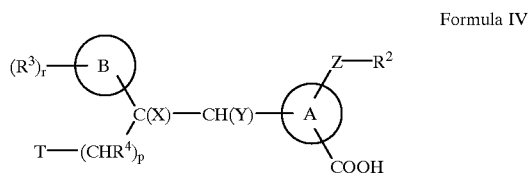

Formula IV with a compound of the Formula V

 Formula V under standard amide bond forming conditions, wherein A, B, T, Z, r, p and $R^2$—$R^4$ are as hereinabove defined and $X^1$ is of the formula —$C(R^8)R^9C(O)R^{10}$ or 2-oxotetrahydrofuran-3-yl wherein $R^8$—$R^{10}$ are as defined in claim 1, and wherein any functional group is protected, if necessary, and thereafter:

i. removing any protecting groups;

ii. optionally forming a pharmaceutically acceptable salt or in vivo hydrolysable ester.

Typically a carbodiimide coupling reagent is used in the presence of an organic solvent (preferably an anhydrous polar aprotic organic solvent) at a non-extreme temperature, for example in the region −10 to 40°, typically ambient temperature of about 20°.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg benzyl, p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C) alkenyl groups (eg allyl and vinylethyl).

Methods particularly appropriate for the removal of carboxyl protecting groups include for example acid-, base-, metal- or enzymically-catalysed hydrolysis.

Examples of hydroxyl protecting groups include lower alkyl groups (eg t-butyl), lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups.

Examples of amino protecting groups include formyl, aralkyl groups (eg benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl; trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

The compound of Formula IV may be prepared by reacting a compound of Formula VI:

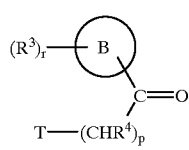

Formula VI with a compound of Formula VII:

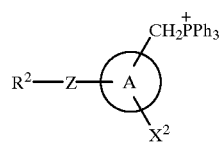

Formula VII wherein $X^2$ represents a carboxy group in protected form and variable groups are as hereinbefore defined or an activated derivative thereof, under standard Wittig reaction conditions to form a double bond, wherein any functional group is protected, if necessary, and thereafter:

i. optionally hydrogenating the double bond thus formed (to give compounds of Formula IV in which X and Y are hydrogen if desired); and ii. removing any protecting groups.

Suitable Wittig reaction conditions include using a polar aprotic organic solvent in the presence of a crown ether and an alkali metal cation, preferably at −50 to −5° C. C18 HPLC may be used to separate E and Z isomers at this stage or later if appropriate. Suitable hydrogenation conditions include use of a catalyst, preferably palladium on carbon in the presence of an organic solvent at a non-extreme temperature.

Biological activity was tested as follows. Farnesyl protein transferase (FPT) was partially purified from human placenta by ammonium sulphate fractionation followed by a single Q-Sepharose™ (Pharmacia, Inc) anion exchange chromatography essentially as described by Ray and Lopez-Belmonte (Ray K P and Lopez-Belmonte J (1992) Biochemical Society Transations 20 494–497). The substrate for FPT was Kras (CVIM C-terminal sequence). The cDNA for oncogenic val12 variant of human c-Ki-ras-2 4B was obtained from the plasmid pSW11-1 (ATCC). This was then subcloned into the polylinker of a suitable expression vector e.g. pIC147, The Kras was obtained after expression in the E. coli strain, BL21. The expression and purification of c-KI-ras-2 4B and the val12 variant in E. coli has also been reported by Lowe et al (Lowe P N et al. J. Biol. Chem. (1991) 266 1672–1678).

Incubations with enzyme contained 300 nM tritiated farnesyl pyrophosphate (DuPont/New England Nuclear), 120 nM ras-CVIM, 50 mM Tris HCl pH 8.0, 5 mM $MgCl_2$, 10 μM $ZnCl_2$, 5 mM dithiotheitol and compounds were added at appropriate concentrations in DMSO (3% final concentration in test and vehicle control). Incubations were for 20 minutes at 37° and were stopped with acid ethanol as described by Pompliano et al. (Pompliano D L et al (1992) 31 3800–3807). Precipitated protein was then collected onto glass fibre filter mats (B) using a Tomtec™ cell harvester and tritiated label was measured in a Wallac™ 1204 Beta-plate scintillation counter.

Although the pharmacological properties of the compounds of the Formula I vary with structural change as expected, in general compounds of the Formula I possess an $IC_{50}$ in the above test in the range, for example, 0.0005 to 50 μM. Thus by way of example the compound of Example 6 herein has an $IC_{50}$ of approximately 0.15 μM. No physiologically unacceptable toxicity was observed at the effective dose for compounds tested of the present invention.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) C18 reverse phase silica separation;

(iv) yields are given for illustration only and are not necessarily the maximum attainable;

(v) the end-products of the Formula I have satisfactory microanalyses and their structures were confirmed by nuclear magnetic resonance (NMR) and mass spectral techniques; chemical shift values were measured on the delta scale; the following abbreviations have been used: s, singlet; d, doublet; t or tr, triplet; m, multiplet; br, broad;

(vi) intermediates were not generally fully characterised and purity was assessed by thin layer chromatographic, HPLC, infra-red (IR) or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:
BOC tert-butoxycarbonyl
DCCI 1,3-dicyclohexylcarbodiimide
DMA N,N-dimethylacetamide
DMAP 4-dimethyl-aminopyridine
DMF N,N-dimethylformamide
DMSO dimethylsulfoxide
EDC 1-(3-dimethylaminopropyl)-3-ethyl-carbodiimide
EEDQ 2-ethoxy-1-ethoxycarbonyl-1,2-dihydroquinoline
HOBT 1-hydroxybenzotriazole
NMM N-methylmorpholine
NMM-O 4-methylmorpholine-N-oxide
RT room temperature
TFA trifluoroacetic acid
THF tetrahydrofuran
TMSI trimethylsilyliodide
TPAP tetrapropylammonium perruthenate

EXAMPLE 1

Preparation of a) (2S)-2-{3-[(E)-2-(4-Fluorophenyl)-3-(imidazol-1-yl)-prop-1-enyl]-benzamido}-4-methylsulfanylbutyric acid b) Isopropyl (2S)-2-{3-[(E)-2-(4-fluorophenyl)-3-(imidazol-1-yl)-prop-1-enyl]-benzamido}-4-methylsulfanylbutanoate c) (2S)-2-{3-[(E)-2-(4-Fluorophenyl)-3-(imidazol-1-yl)-prop-1-enyl]-benzamido}-4-carbamoylbutyric acid d) (2S)-2-{3-[(E)-2-(4-Fluorophenyl)-3-(imidazol-1-yl)-prop-1-enyl]-benzamido}-4-methylsulfonylbutyric acid; and e) (2S)-2-{3-[(E)-2-(4-Fluorophenyl)-3-(imidazol-1-yl)-prop-1-enyl]-benzamido}-4-hydroxybutyric acid

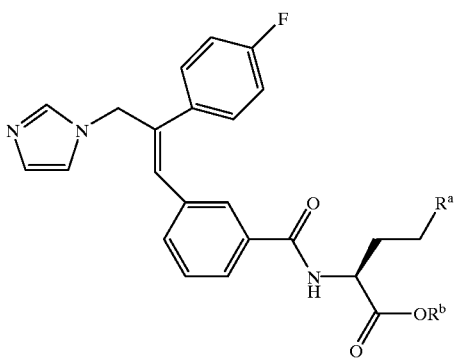

| Compound | $R^a$ | $R^b$ |
| --- | --- | --- |
| a) | $SCH_3$ | H |
| b) | $SCH_3$ | $CHMe_2$ |
| c) | $CONH_2$ | H |
| d) | $SO_2Me$ | H |
| e) | OH | H |

Preparation of Compound a)

A) The desired end product was prepared as follows. A solution of starting material methyl (2S)-2-{3-[(E)-2-(4-fluorophenyl)-3-(imidazol-1-yl)-prop-1-enyl]-benzamido}-4-methylsulfanylbutanoate (0.1 g; 0.22 mmol) in methanol (5 ml) was treated with 2N aqueous sodium hydroxide solution (0.5 ml) and stirred at room temperature for 2 h 20 min. After evaporation of the methanol, the aqueous reaction mixture was acidified to pH 5 and purified on reverse phase silica eluting with a gradient of 50–60% MeOH/$(NH_4)_2CO_3$ buffer (2 g/l, pH 7). The appropriate fractions were concentrated and freeze-dried to give the desired end product as a solid (70 mg; 70%). Melting Point=102–104° C.

$^1$H NMR ($CDCl_3$+$CF_3COOD$, 400 MHz) δ2.1–2.3 (5H, m); 2.6–2.8 (2H, m); 4.95 (1H, m); 5.19 (2H, m); 6.89–7.6 (11H, m); 8.68 (1H, s).

Anal. calcd for $C_{24}H_{24}FN_3O_3S$, 0.2 $H_2O$ C, 63.07; H, 5.35; N, 9.19; S, 7.00.

Found: C, 63.29; H, 5.79; N, 8.76; S, 7.08.

MS (ESI) m/z 454 (MH$^+$)

The desired starting material was prepared as follows

B) Potassium tert-butoxide (8.8 g, 72 mmol) was added to a mixture of 1-(4-fluorophenyl)-2-(imidazol-1-yl)-ethanone (9.8 g, 48 mmol), 3-(methoxycarbonylbenzyl)-triphenylphosphonium bromide (35.4 g, 72 mmol) and 18-crown-6 (0.25 g, 0.94 mmol) in methylene chloride (300 ml), at −40° C. under an argon atmosphere. After stirring overnight, at room temperature, the resulting mixture was treated by a saturated solution of $NH_4Cl$ and extracted with $CH_2Cl_2$ and subjected to flash chromatography eluting with $CH_2Cl_2$/MeOH (98/2) to give methyl 3-(2-(4-fluorophenyl)-3-imidazol-1-yl-propenyl)benzoate as a mixture of E and Z isomers (11 g). Yield (E+Z)=68%

C) For characterisation purposes, a pure sample of E isomer was obtained after purification on reverse phase silica (Nucleosil 120 C18 10 μm 1"×25 cm) eluting a gradient of methanol 40–60% in $(NH_4)_2$ $CO_3$ buffer (2 g/l pH 7). Appropriate fractions were evaporated and extracted with dichloromethane. After removal of the solvent the residue was taken up in ether, treated with HCl/ether to give methyl 3-((E)-2-(4-fluorophenyl)-3-(imidazol-1-yl)-prop-1-enyl)benzoate as a solid which was filtered.

Melting Point: 145–148° C.

¹H NMR (CDCl₃, 400 MHz) δ3.85 (3H, s); 5.39 (2H, s); 6.9–7.3 (8H, m); 7.7–7.9 (2H, m); 9.49 (1H, s)

Anal calcd for $C_{20}H_{17}FN_2O_2$, 1 HCl, 0.2 $H_2O$ C, 64.13; H, 4.94; N, 7.48; Cl, 8.99.

Found: C, 64.57; H, 5.24; N, 7.42; Cl, 8.90.

MS (ESI) m/z 337 (MH⁺).

D) A solution of the product from step B (E and Z isomers) (11 g, 32.7 mmol) in MeOH (150 ml) was treated with 2N NaOH (32 ml, 65 mmol) for 3 hours. Methanol was then evaporated and the solution was acidified to pH 5.5 with 6N HCl. The resulting precipitate was filtered and washed with a small quantity of water. The precipitate was taken up in MeOH. The insoluble material was washed with a mixture of MeOH/ether to give after drying 2.3 g of E isomer 3-((E)-2-(4-fluorophenyl)-3-(imidazol-1-yl)-prop-1-enyl)benzoic acid (22%). The above filtrate was evaporated and triturated in ether to give the E isomer 3-((E)-2-(4-fluorophenyl)-3-(imidazol-1-yl)-prop-1-enyl)benzoic acid (7.7 g, 67%) as a solid.

Melting Point=185–187° C.

¹H NMR (CDCl₃+CF₃COOD, 400 MHz) δ5.20 (2H, s); 6.91–7.81 (9H, m); 7.7–7.95 (2H, m); 8.75 (1H, s)

Anal. calcd for $C_{19}H_{15}FN_2O_2$ C, 70.8; H, 4.69; N, 8.69.

Found: C, 70.30; H, 4.82; N, 8.70.

MS (ESI) m/z 323 (MH⁺)

E) A mixture of E isomer from step D (0.2 g, 0.62 mmol), L-methionine methyl ester hydrochloride (0.124 g, 0.62 mmol), HOBT (0.084 g, 0.62 mmol), EDC (0.120 g, 0.62 mmol) and N-methylmorpholine (0.068 ml, 0.62 mmol) in CH₂Cl₂ (20 ml) was stirred overnight at room temperature, washed with saturated NaHCO₃ (aqueous). The organic phase was evaporated and the residue purified on reverse phase silica eluting a gradient of 40–50% MeOH/(NH₄)₂CO₃ buffer (2 g/l pH 7). Appropriate fractions were evaporated and extracted with CH₂Cl₂, evaporated and triturated with pentane to give the desired starting material as a foam (0.140 g 50%).

Melting Point=50–53° C.

¹H NMR (CDCl₃, 400 MHz) δ2.0–2.30 (2H, m); 2.10 (3H, s); 2.50–2.55 (2H, m); 3.79 (3H, s); 4.87 (2H, s); 6.50–7.61 (12H, m).

MS (ESI) m/z 468 (MH⁺)

Anal. Calcd for $C_{25}H_{26}FN_3O_3S$ C, 64.2; H, 5.61; N, 8.99; S, 6.86.

Found: C, 64.72; H, 5.98; N, 8.98; S, 6.69.

Preparation of Compound b)

A) Compound b) was synthesised in an analogous manner to that described for compound a), step E, but substituting L-methionine isopropyl ester (in lieu of the methyl ester).

Melting Point: 115–118° C.

¹H NMR (CDCl₃) δ1.27 (6H, d); 1.9–2.3 (2H, m); 2.10 (3H, s); 2.4–2.56 (2H, m); 4.70–4.80 (1H, m); 4.87 (2H, s); 5.05–5.15 (1H, m); 6.54 (2H, m); 6.92–7.60 (10H, m)

Anal. calculated for $C_{27}H_{30}FN_3O_3S$ C, 65.4; H, 6.10; N, 8.48; S, 6.47.

Found: C, 65.95; H, 6.63; N, 8.0; S, 5.84.

MS (ESI) m/z 496 (MH⁺)

Preparation of Compound c)

A) Compound c) was prepared as follows. Starting material tert-butyl (2S)-2-{3-[(E)-2-(4-fluorophenyl)-3-(imidazol-1-yl)-prop-1-enyl]-benzamido}-4-carbamoylbutanoate (0.360 g; 0.7 mmol) was treated in TFA (3 ml) at room temperature for 1 hour. After evaporation, the residue was taken up in water, basified to pH 6 with 2N NaOH and purified on reverse phase silica eluting with a gradient of 30–40% MeOH in (NH₄)₂CO₃ buffer (2 g/l pH 7) and freeze dried to give the end product as a foam (0.247 g; 84%).

Melting Point=121–124° C.

¹H NMR (DMSO-D₆+CF₃COOD) δ1.8–2.15 (2H, m); 2.15–2.3 (2H, m); 4.32 (1H, m); 5.35 (2H, s); 6.94 (1H, s); 7.0–7.27 (5H, m); 7.64–7.72 (4H, m); 8.7 (1H, d); 9.08 (1H, s).

Anal. calculated for $C_{24}H_{23}FN_4O_4$, 1.35 $H_2O$ C, 60.71; H, 5.46; N, 11.80.

Found: C, 60.28; H, 5.38; N, 12.00.

MS (ESI) m/z 451 (MH⁺)

B) The starting material was synthesised using analogous methodology to that described for compound a), step E but using L-glutamine tert-butyl ester (in lieu of L-Met methyl ester), yield=55%.

¹H NMR (DMSO-D₆+CF₃COOD, 400 MHz) δ1.41 (9H, s); 1.90–2.15 (2H, m); 2.19–2.23 (2H, m); 4.24 (1H, m); 5.35 (2H, s); 6.94–7.25 (7H, m); 7.64–7.72 (4H, m); 8.67 (1H, m); 9.09 (1H, s).

Anal. Calculated for $C_{28}H_{31}FN_4O_4$, 2.2 $H_2O$ C, 61.67; H, 6.52; N, 10.27.

Found: C, 59.47; H, 6.38; N, 10.43.

MS (ESI) m/z 507 (MH⁺).

Preparation of Compound d)

A) Compound d) was prepared as follows. A solution of starting material, methyl (2S)-2-{3-[(E)-2-(4-fluorophenyl)-3-(imidazol-1-yl)-prop-1-enyl]-benzamido}-4-methylsulfonylbutanoate (0.15 g; 0.3 mmol) in MeOH (5 ml) was treated with NaOH (2N, 0.5 ml) at room temperature for 2 hours. After evaporation, the residue was purified on reverse phase silica eluting with MeOH/(NH₄)₂CO₃ (2 g/l pH 7) 40/60 and freeze dried to give the desired end product as a foam (0.11 g; 76%).

Melting Point=120–125° C.

¹H NMR (CDCl₃+CF₃COOD, 400 MHz) δ2.19–2.75 (2H, m); 3.10 (3H, s); 3.20–3.5 (2H, m); 4.96 (1H, m); 5.19 (2H, s); 6.88 (1H, s); 7.02–7.63 (11H, m)

Anal. calculated for $C_{24}H_{24}FN_3O_5S$, 0.9 $H_2O$ C, 57.45; H, 5.18; N, 8.37; S, 6.39.

Found: C, 57.90; H, 5.17; N, 8.52; S, 6.16.

MS (ESI): m/z 486 (MH⁺)

The starting material was prepared as follows.

B) To a solution of methyl (2S)-2-{3-[(E)-2-(4-fluorophenyl)-3-(imidazol-1-yl)-prop-1-enyl]-benzamido}-4-methylsulfanylbutanoate (0.468 mg, 1 mmol; prepared as described in step E for compound a) above) in CH₂Cl₂ (20 ml) was added m-chloroperbenzoic acid (0.74 g; 3 mmol). After stirring at room temperature for 2 hours, the organic layer was washed with Na₂S₂O₂ (aq), NaHCO₃ (aq) and brine and then evaporated. The residue was purified on reverse phase silica eluting a gradient of 40–50% MeOH in (NH₄)₂CO₃ buffer (2 g/l pH 7). Appropriate fractions were evaporated, extracted with CH₂Cl₂ and evaporated to give the desired starting material as a solid (0.230 mg; 46%).

Melting Point=72–75° C.

¹H, NMR (CDCl₃, 400 MHz) δ2.17–2.56 (2H, m); 2.93 (3H, s); 2.95–3.21 (2H, m); 3.82 (3H, s); 4.81–4.85 (1H, m); 4.87 (2H, s); 6.54 (1H, s); 6.67 (1H, d); 6.93–7.26 (7H, m); 7.39 (2H, d); 7.60 (1H, d).

MS (ESI) m/z 500 (MH⁺)

Anal. calculated for $C_{25}H_{26}FN_3O_5S$ C, 60.1; H, 5.25; N, 8.41; S, 6.42,

Found: C, 60.16; H, 5.62; N, 8.02; S, 6.06.

Preparation of Compound e)

A) Compound e) was prepared as follows. Starting material (2S)-2-{3-[(E)-2-(4-fluorophenyl)-3-(imidazol-1-yl)-prop-1-enyl]-benzamido}-4-butanolide (0.150 g; 0.37 mmol) in solution in MeOH (5 ml) was treated with NaOH 2N, (0.5 ml) at room temperature overnight. After evaporation of the methanol, the solution was acidified to pH 7 and purified on reverse phase silica eluting with MeOH/(NH$_4$)$_2$CO$_3$ 2 g/l pH 7, 40/60. After evaporation of the methanol and freeze drying the desired end product was obtained as a foam (0.130 g; 86%)

Melting Point=104–107° C.

$^1$H NMR (CDCl$_3$+CF$_3$COOD, 400 MHz) δ2.25–2.40 and 2.85–3.0 (2H, m); 4.4–4.5 and 4.6–4.7 (2H, m); 4.8–4.9 (1H, m); 5.19 (2H, s); 6.88 (1H, s); 7–7.6 (10H, m); 8.76 (1H, s).

Anal. calculated for C$_{23}$H$_{22}$FN$_3$O$_4$, 1.6 H$_2$O C, 62.07; H, 5.53; N, 9.44.

Found: C, 62.44; H, 5.58; N, 9.27.

MS (ESI) m/z 424 (MH$^+$)

B) The starting material was prepared using the same coupling methodology as described in step E of compound a) above but using 2-amino-4-butyrolactone (in lieu of methionine methyl ester).

Melting Point=87–91° C.

$^1$H NMR (CDCl$_3$ 400 MHz) δ2.13–2.20 and 2.91–3 (2H, m); 4.30–4.70 (3H, m); 4.87 (2H, s); 6.45 (1H, s); 6.52 (1H, s); 7.02–7.59 (11H, m).

Anal. calculated for C$_{23}$H$_{20}$HN$_3$O$_3$, 1 H$_2$O C, 65.24; H, 5.24; N, 9.92

Found: C, 65.62; H, 5.17; N, 9.90.

MS (ESI) m/z 406 (MH$^+$).

EXAMPLE 2

Preparation of a) (2)-2-{3-[2-(4-Fluorophenyl)-3-(imidazol-1-yl)-propyl]-benzamido}-4-methylsulfanylbutyric acid; and b) Isopropyl (2S)-2-{3-[2-(4-fluorophenyl)-3-(imidazol-1-yl)-propyl]-benzamido}-4-methylsulfanylbutanoate

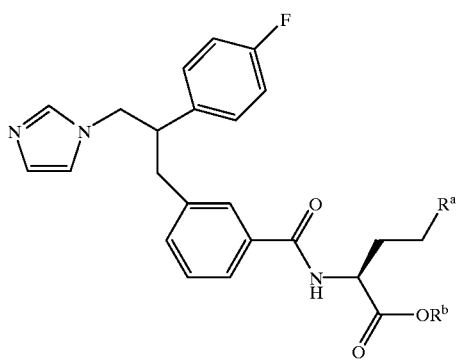

| Compound | R$^a$ | R$^b$ |
|---|---|---|
| a) | SCH$_3$ | H |
| b) | SCH$_3$ | CHMe$_2$ |

Preparation of Compound a)

A) Compound a) was synthesised from starting material methyl (2S)-2-{3-[2-(4-fluorophenyl)-3-(imidazol-1-yl)-propyl]-benzamido}-4-methylsulfanylbutanoate using analogous methodology to that described in Example 1, compound a), step A (yield 86%).

MP=98–102° C.

$^1$H NMR (CDCl$_3$+CF$_3$COOD, 400 MHz) δ2.16 (3H, s); 2.19–2.45 (2H, m); 2.68 (2H, m); 3.09 (2H, d); 3.45 (1H, m); 4.3–4.52 (2H, m); 4.97 (1H, m); 6.9–7.75 (10H, m); 8.47 (1H, s).

Anal. calculated for C$_{24}$H$_{26}$FN$_3$O$_3$S, 0.26 H$_2$O C, 62.6; H, 5.81; N, 9.13; S, 6.97.

Found: C, 62.18; H, 6.03; N, 9.18; S, 6.78.

MS (ESI) m/z 456 (MH$^+$)

B) The starting material was synthesised as follows.

To a solution of the E and Z isomers prepared in Example 1, compound a), step D (2 g; 6.2 mmol) in MeOH (70 ml) was added TFA (0.504 ml; 7 mmol) and 10% Pd/C (0.5 g). The mixture was hydrogenated for 2 hours. After filtration of the catalyst and evaporation to dryness, the residue was triturated in ether to give 3-(2-(4-fluorophenyl)-3-(imidazol-1-yl)-propyl)benzoic acid as a white solid (2 g; 99%).

MP: 125–130° C.

$^1$H NMR (CDCl$_3$+CF$_3$COOD, 400 MHz) δ3.13 (2H, m; 3.40 (2H, m); 4.38 and 4.55 (2H, m); 6.82 (1H, s); 6.90–7.15 (4H, m); 7.25–7.40 (3H, m); 7.80 (1H, s); 7.94 (1H, d); 8.49 (1H, s)

MS (ESI) m/z 325 (MH$^+$)

C) The desired starting material was synthesised from the product of step B using the analogous methodology to that described in Example 1, compound a), step A and was obtained as an oil (yield 54%).

$^1$H NMR (CDCl$_3$, 400 MHz) δ2.10–2.20 and 2.20–2.40 (2H, m); 2.11 (3H, s); 2.58 (2H, m); 3.00 (2H, m); 3.20–3.35 (1H, m); 3.80 (3H, s); 4.05–4.25 (2H, m); 4.93 (1H, m); 6.6 (1H, s); 6.95 (6H, m); 7.1–7.35 (2H, m); 7.49–7.60 (2H, m).

Anal. calculated for C$_{25}$H$_{28}$FN$_3$O$_3$S C, 63.9; H, 6.01; N, 8.95; S, 6.83.

Found: C, 63.69; H, 6.43; N, 8.99; S, 6.57.

MS (ESI) m/z 470 (MH$^+$).

Preparation of Compound b)

A) The desired end product was synthesised from the product prepared in this Example, compound a), step B) using analogous methodology to that described in Example 1, compound b), step A (yield=50%).

$^1$H NMR (CDCl$_3$, 400 MHz) δ1.28 (6H, m); 2.06–2.35 (2H, m); 2.11 (3H, s); 2.60 (2H, m); 3.0 (2H, m); 3.28 (1H, m); 4.05–4.21 (2H, m); 4.82 (1H, m); 5.12 (1H, m); 6.66 (1H, s); 6.84 (1H, s); 6.96 (5H, m); 7.1–7.35 (3H, m); 7.50 (1H, d); 7.59 (1H, d).

Anal. calculated for C$_{27}$H$_{32}$FN$_3$O$_3$S C, 65.2; H, 6.48; N, 8.44; S, 64.4.

Found: C, 65.99; H, 7.08; N, 8.61; S, 6.39.

MS (ESI) m/z 498 (MH$^+$).

EXAMPLE 3

Preparation of (2S)-2-{3-[(Z)-2-(4-fluorophenyl)-3-(imidazol-1-yl)-prop-1-enyl]-benzamido}-4-methylsulfanylbutyric acid

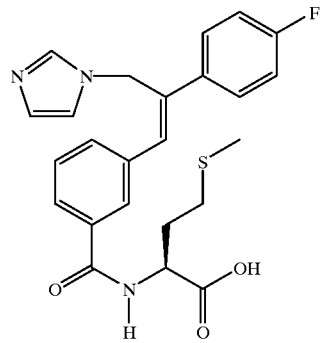

A) The desired end product was prepared from starting material methyl (2S)-2-{3-[( Z)-2-(4-fluorophenyl)-3-(imidazol-1-yl)-prop-1-enyl]-benzamido}-4-methylsulfanylbutanoate using the analogous methodology to that described in step A of Example 1, compound a), (yield=65%).

MP=98–100° C.

$^1$H NMR (CDCl$_3$+CF$_3$COOD, 400 MHz) δ2.28 (3H, s); 2.15–2.45 (2H, m); 2.6–2.9 (2H, m); 5.02 (1H, m); 5.37 (2H, s); 7–7.76 (11H, m); 8.53 (1H, s).

Anal. calculated for C$_{24}$H$_{24}$FN$_3$O$_3$S, 0.2 H$_2$O C, 63.07; H, 5.35; N, 9.19; S, 7.00.

Found: C, 63.35; H, 5.84; N, 8.80; S, 7.02.

MS (ESI) m/z 454 (MH$^+$).

B) The starting material was prepared from 3-((Z)-2-(4-fluorophenyl)-3-(imidazol-1-yl)-prop-1-enyl)benzoic acid (which is the Z isomer prepared in step D of Example 1, compound a)) using analogous methodology to that described in step A of Example 1, compound a) (yield: 50%).

MP=106–110° C.

$^1$H NMR (CDCl$_3$, 400 MHz) δ2.12 (3H, s); 2.10–2.4 (2H, m); 2.59 (2H, m); 3.81 (3H, s); 4.95 (1H, m); 5.06 (2H, s); 6.82–7.15 (6H, m); 7.35–7.50 (4H, m); 7.74 (2H, m).

Anal. calculated for C$_{25}$H$_{26}$FN$_3$S C, 64.2; H, 5.61; N, 8.99; S, 6.86.

Found: C, 62.84; H, 5.84; N, 8.70; S, 6.68.

MS (ESI) m/z 468 (MH$^+$).

EXAMPLE 4

Preparation of a) (2)-2-{3-[(E)-2-(4-Fluorophenyl)-3-(5-methylimidazol-1-yl)-prop-1-enyl]-benzamido}-4-carbamoylbutyric acid; and b) (2S)-2-{3-[(E)-2-(4-Fluorophenyl)-3-(5-methylimidazol-1-yl)-prop-1-enyl]-benzamido}-4-methylsulfanylbutyric acid

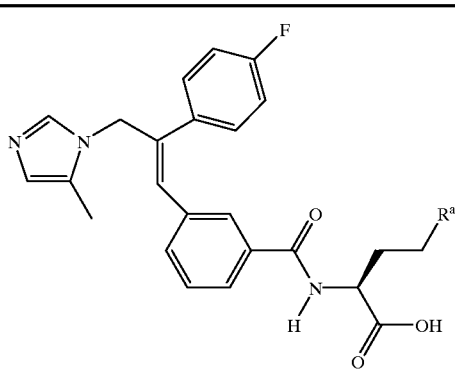

| Compound | R$^a$ |
|---|---|
| a) | CONH$_2$ |
| b) | SCH$_3$ |

Preparation of Compound a)

A) Compound a) was prepared from starting material tert-butyl (2S)-2-{3-[(E)-2-(4-Fluorophenyl)-3-(5-methylimidazol-1-yl)-prop-1-enyl]-benzamido}-4-carbamoylbutanoate using analogous methodology to that described in Example 1, for compound c), step A (yield: 76%).

$^1$H NMR (DMSOd$_6$+CF$_3$COOD, 400 MHz) δ1.8–2.15 (2H, m); 2.15–2.25 (2H, m); 2.31 (3H, s); 4.32 (1H, m); 5.32 (2H, s); 6.83 (1H, s); 7.0 (1H, d); 7.17–7.3 (5H, m); 7.41 (1H, s); 7.6–7.75 (2H, m); 8.93 (1H, s).

Anal. calculated for C$_{25}$H$_{25}$FN$_4$O$_4$, 2 H$_2$O C, 59.99; H, 5.84; N, 11.19.

Found: C, 59.91; H, 5.66; N, 11.55.

MS (ESI) m/z 465 (MH$^+$).

The starting material was prepared as follows.

B) Methyl 3-(2-(4-fluorophenyl)-3-(5-methylimidazol-1-yl)-prop-1-enyl)benzoate as a mixture of E and Z isomers was prepared using analogous methodology to that described in Example 1, compound a), step B but using 1-(4-fluorophenyl)-2-(5-methylimidazol-1-yl)-ethanone in place of 1-(4-fluorophenyl)-2-(imidazol-1-yl)-ethanone. The mixture of E and Z isomers is used in the next step without further purification.

C) The product from step B) (3.94 g; 11 mmol) in methanol (20 ml) was treated with NaOH (2N, 12 ml). Methanol was then evaporated and the solution acidified to pH 5.5. The resulting solid was triturated in MeOH, the insoluble material was filtered and dried to give 3-((E)-2-(4-fluorophenyl)-3-(5-methylimidazol-1-yl)-propenyl) benzoic acid as a white solid (0.597g; 15%).

$^1$H NMR (DMSOd$_6$+CF$_3$COOD, 400 MHz) δ2.30 (3H, s); 5.30 (2H, s); 6.85 (1H, s); 7.1–7.8 (9H, m); 8.92 (1H, s).

D) The desired starting material was prepared from the product of step C) being coupled with L-glutamine tert-butyl ester using analogous methodology to that described in Example 1, compound a), step E), (yield: 52%).

$^1$H NMR (DMSOd$_6$+CF$_3$COOD, 400 MHz) δ1.4 (9H, s); 1.8–2.15 (2H, m); 2.1–2.3 (2H, m); 2.30 (3H, s); 4.22 (1H, m); 5.32 (2H, s); 6.83 (1H, s); 7.16 (1H, d); 7 (1H, d); 7.1–7.3 (4H, m); 7.4 (1H, s); 7.6–7.75 (2H, m); 8.85 (1H, s).

Anal. calculated for C$_{29}$H$_{33}$FN$_4$O$_4$, 0.26 H$_2$O C, 66.31; H, 10.67; N, 6.43.

Found: C, 65.78; H, 10.36; N, 6.87.

MS (ESI) m/z 521 (MH$^+$)

Preparation of Compound b)

A) Compound b) was prepared from starting material methyl (2S)-2-{3-[(E)-2-(4-fluorophenyl)-3-(5-methylimidazol-1-yl)-prop-1-enyl]-benzamido}-4-methylsulfanylbutanoate using analogous methodology to that described in Example 1, compound a), step A (yield: 8%).

$^1$H NMR (DMSOd$_6$+CF$_3$COOD, 400 MHz) δ2.05 (3H, s); 2–2.1 (2H, m); 2.31 (3H, s); 2.4–2.7 (2H, m); 4.45 (1H, m); 5.32 (2H, s); 6.8 (1H, s); 7 (1H, d); 7.1–7.3 (5H, m); 7.4 (1H, s); 7.6 (1H, s); 7.7 (1H, d); 8.9 (1H, s).

Anal. calculated for C$_{25}$H$_{26}$FN$_3$O$_3$S C, 61.84; H, 5.81; N, 8.65; S, 6.60.

Found: C, 61.75; H, 6.10; N, 8.27; S, 6.38.

MS (ESI) m/z 468 (MH$^+$).

B) The starting material was prepared by coupling the product of step C, compound a) in this Example with L-methionine methyl ester using analogous methodology to that described in Example 1, compound a), step E) (yield: 67%).

$^1$H NMR (CDCl$_3$, 400 MHz) δ1.95–2.15 (2H, m); 2.05 (3H, s); 2.31 (3H, s); 2.4–2.6 (2H, m); 2.54 (3H, s); 3.64 (3H, s); 4.54 (1H, m); 5.33 (2H,s); 6.83 (1H, s); 7.03 (1H, d); 7.1–7.3 (5H, m); 7.41 (1H, s); 7.60 (1H, s); 7.68 (1H, d); 8.94 (1H, s).

Anal. calculated for C$_{26}$H$_{28}$FN$_3$O$_3$S, 1 HCl, 0.5 H$_2$O C, 59.25; H, 5.74; N, 7.07; S, 6.08.

Found: C, 59.44; H, 5.92; N, 7.76; S, 5.85.

MS (ESI) m/z 482 (MH$^+$).

EXAMPLE 5

Preparation of a) (2S)-2-{3-[(Z)-3-(imidazol-1-yl)-2-(thiazol-2-yl)-prop-1-enyl]-nzamido}-4-methylsulfanylbutyric acid; and b) (2S)-2-{3-[(Z)-3-(imidazol-1-yl)-2-(thiazol-2-yl)-prop-1-enyl]-benzamido}-4-carbamoylbutyric acid

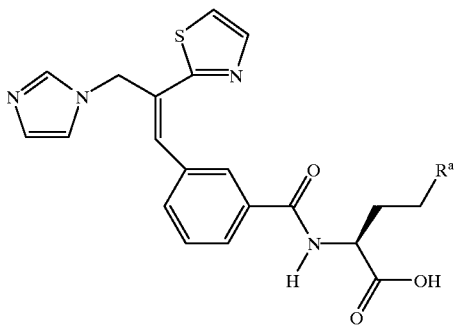

| Compound | $R^a$ |
|---|---|
| a) | $SCH_3$ |
| b) | $CONH_2$ |

Preparation of Compound a)

A) Compound a) was prepared from starting material methyl (2S)-2-{3-[(Z)-3-(imidazol-1-yl)-2-(thiazol-2-yl)-prop-1-enyl]-benzamido}-4-methylsulfanylbutyrate using analogous methodology to that described in Example 1, compound a), step A), (yield: 77%).

MP: 152–156° C.

$^1$H NMR (CDCl$_3$+CF$_3$COOD, 400 MHz) δ2.15 (3H, s); 2.16–2.4 (2H, m); 2.6–2.8 (2H, m); 4.95 (1H, m); 5.55 (2H, s); 7.26 (1H, d); 7.4–7.6 (5H, m); 7.77 (1H, d); 7.82 (1H, d); 8.08 (1H, d); 9.01 (1H, s).

Anal. calculated for C$_{21}$H$_{22}$N$_4$O$_3$S$_2$, 0.3 H$_2$O C, 56.31; H, 5.09; N, 12.51; S, 14.32.

Found: C, 56.67; H, 5.16; N, 12.62; S, 14.06.

MS (ESI) m/z 443 (MH$^+$)

The starting material was prepared as follows.

B) To a solution of 2-bromo-1-(thiazol-2-yl)-ethanone (2.5 g; 12 mmol) in CH$_3$CN (70 ml) was added imidazole (1.65 g; 24 mmol). After stirring at room temperature for 1 hour, the mixture was evaporated to dryness and partitioned between CH$_2$Cl$_2$ and water. The organics were washed with saturated NaCl and evaporated to give 2-(imidazol-1-yl)-1-(thiazol-2-yl)-ethanone as a brown solid (1.17 g; 50%).

MP: 109–112° C.

$^1$H NMR (DMSOd$_6$, 400 MHz) δ5.6 (2H, s); 6.85–8.1 (5H, m).

C) The product of step B) was reacted with 3-(methoxycarbonylbenzyl)-triphenylphosphonium bromide using methodology as described in Example 1, compound a) step B, to give methyl 3-(3-(imidazol-1-yl)-2-(thiazol-2-yl)-prop-1-enyl)benzoate as a mixture of E and Z isomers (yield: 86% E+Z isomers)

$^1$H NMR (CDCl$_3$, 400 MHz) δ3.89 and 3.93 (3H, s); 5.22 and 5.28 (2H, s); 6.7–8.15 (10H, m).

MS (ESI) m/z 326 (MH$^+$)

D) The product of step C) (2.6 g; 8 mmol) in solution in MeOH (60 ml) was treated with NaOH 2N, (8 ml; 16 mmol) at room temperature for 2 hours. After evaporation of the methanol, the residue was acidified to pH 6 with HCl 6N, to precipitate a solid which was washed with water and ether to give 3-(3-(imidazol-1-yl)-2-(thiazol-2-yl)-prop-1-enyl)benzoic acid as a mixture of E and Z isomers (2 g; 80%).

$^1$H NMR (DMSO+CF$_3$COOD, 400 MHz) δ5.49 and 5.55 (2H, s); 7.35–8.1 (9H, m); 9.2 and 9.27 (1H, s).

E) Product from step D) was reacted with L-methionine methyl ester hydrochloride using the conditions as described in Example 1, compound a), step E and the Z isomer purified on C18 HPLC to give the desired starting material (yield 57%).

$^1$H NMR (CDCl$_3$, 400 MHz) δ2–2.35 (2H, m); 2.09 (3H, s); 2.55 (2H, m); 3.79 (3H, s); 4.90 (1H, m); 5.22 (2H, s); 6.71 (1H, s); 6.84 (1H, d); 7–7.85 (9H, m).

Anal. calculated for C$_{22}$H$_{24}$N$_4$O$_3$S$_2$ C, 57.9; H, 5.30; N, 12.3; S, 14.0.

Found: C, 57.47; H, 5.71; N, 12.12; S, 13.5.

MS (ESI) m/z 457 (MH$^+$)

Preparation of Compound b)

A) Compound b) was obtained from starting material tert-butyl (2S)-2-{3-[(Z)-3-(imidazol-1-yl)-2-(thiazol-2-yl)-prop-1-enyl]-benzamido}-4-carbamoylbutyrate using methodology as described in Example 1, compound c), step A (yield: 91%).

MP: 110–115° C.

$^1$H NMR (DMSOd$_6$+CF$_3$COOD, 400 MHz) δ1.8–2.2 (2H, m); 2.22 (2H, m); 4.35 (1H, m); 5.50 (2H, s); 7.30–8 (9H, m); 8.8 (1H, d); 9.27 (1H, s).

Anal. calculated for C$_{21}$H$_{21}$N$_5$O$_4$S, 1.5 H$_2$O C, 54.07; H, 5.19; N, 15.01; S, 6.87.

Found: C, 54.11; H, 5.43; N, 16.38; S, 6.80.

MS (ESI) m/z 440 (MH$^+$).

B) The starting material was prepared by reaction of 3-(3-(imidazol-1-yl)-2-(thiazol-2-yl)-prop-1-enyl)benzoic acid (see compound a), step D in this Example) with L-glutamine tert-butyl ester using similar methodology as described for Example 1, compound c), step B.

MP: 70–72° C.

$^1$H NMR (CDCl$_3$, 400 MHz) δ1.48 (9H, s); 2–2.45 (4H, m); 4.60 (1H, m); 5.22 (2H, s); 6.76 (1H, s); 7–7.80 (9H, m).

Anal. calculated for C$_{25}$H$_{29}$N$_5$O$_4$S C, 60.6; H, 5.90; N, 14.1; S, 6.47.

Found: C, 60.35; H, 6.16; N, 13.96; S, 6.11.

MS (ESI) m/z 496 (MH$^+$)

EXAMPLE 6

Preparation of (2S)-2-{4-[(E)-3-(imidazol-1-yl)-3-methyl-2-phenyl-prop-1-enyl]-benzamido}-4-methylsulfanylbutyric acid

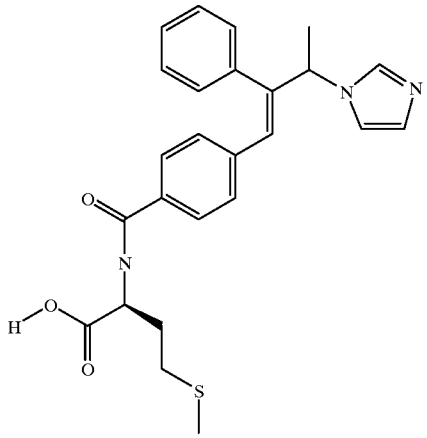

A) A solution of starting material methyl (2S)-2-{4-[(E)-3-(imidazol-1-yl)-3-methyl-2-phenyl-prop-1-enyl]-benzamido}-4-methylsulfanylbutanoate (0.15 g, 0.32mmol) in MeOH (1 ml) was treated with 1M NaOH (0.5 ml, 0.5 mmol), the mixture stirred at room temperature for 18 hrs. The residue obtained by evaporation of the mixture dissolved in water (5 ml) and treated with 1M HCl (0.5 ml/). The oil obtained was extracted with EtOAc and evaporated to give the desired end product as a solid. (0.05 g, yield=34%)

$^1$H NMR (DMSO $d_6$, 300 MHz) δ1.62(3H, d); 2.03(3H+2H, s+m); 2.50(?, m); 4.45(1H, m); 5.35(1H, q); 6.60(1H, d); 6.92(5H, m); 7.22(1H, s); 7.29(3H, m); 7.62(3H, m); 8.46(1H, d).

MS(ESP+) m/z 450 (MH+)

The starting material was prepared as follows.

B) A mixture of 2-bromopropiophenone (21.3 g, 0.1M), imidazole (20.4 g, 0.3M), triethylethylamine (30.3 g, 0.3M) and ethyl acetate (300 ml) was refluxed overnight, cooled to room temperature and treated with water. The organic phase was separated, dried over MgSO$_4$ and evaporated to give 2-(imidazol-1-yl)propiophenone as a viscous oil (12.95 g, Yield=65%)

$^1$H NMR (DMSO $d_6$, 300 MHz) δ1.63(3H, d); 6.27(1H, q); 6.87(1H, s); 7.20(1H, s); 7.54(2H, t); 7.65(1H, t); 7.74 (1H, s); 8.02(2H, d).

A sample (190 mg, 9.5×10$^{-4}$M) was dissolved in CH$_2$Cl$_2$ (4 ml) and Et$_2$O/HCl (1 ml, 9.5×10$^{-4}$M) added. The resultant gum was triturated with Et$_2$O to give 2-(imidazol-1-yl) propiophenone as its hydrochloride salt.

MP: 179–181° C.

$^1$H NMR (DMSO $d_6$, 250 MHz) δ1.8(3H, d); 6.70(1H, q); 7.53(2H, m); 7.75(2H, m); 7.89(1H, t); 8.09(2H, d); 9.37 (1H, t).

Anal calculated for $C_{12}H_{12}N_2O$, 1 HCl C, 61.1; H, 5.4; N, 11.7.

Found: C, 60.9; H, 5.5; N, 11.8.

MS(CI+,EI+,ESP+) m/z 201 (MH+)

C) To a mixture of the product from step B (2.0 g, 10 mmol), (4-cyanophenyl)triphenylphosphonium chloride (4.14 g, 10 mmol) and CH$_2$Cl$_2$ (60 ml), was added at 20° lithium bis(trimethylsilyl)amide, 1M solution in THF/cyclohexane (10 ml, 10 mmol). After stirring for 18 hrs at room temperature the resulting mixture was treated with water, extracted with CH$_2$Cl$_2$ and subjected to chromatography (a Biotage Flash 40 system fitted with a 90 g KP-Sil cartridge) eluting with CH$_2$Cl$_2$, then 1% to 4% MeOH/CH$_2$Cl$_2$ to give 4-[(E)-3-(imidazol-1-yl)-3-methyl-2-phenyl-prop-1-enyl]-benzonitrile (0.7 g, Yield=23%).

$^1$H NMR (DMSO $d_6$, 300 Mz) δ5.34(1H, q); 6.75(1H, s); 7.00(2H, d); 7.19(1H, s); 7.29(3H,m); 7.56(2H, d); 7.58(1H, s).

The absolute configuration was determined using the Nuclear Overhauser Effect

MS(ESP+) m/z 300 (MH+)

Anal calculated for $C_{20}H_{17}N_3$ C, 80.2; H, 5.7; N, 14.0.

Found: C, 79.8; H, 5.8; N, 14.0.

D) A mixture of the product from step C (0.21 g, 1.05 mmol) and concentrated hydrochloric acid was heated to 95° C. for 18 hrs,the solution evaporated, the residue dissolved in MeOH, treated with concentrated aqueous ammonia solution (S.G. 0.880), evaporated to dryness and triturated with water to give 4-[(E)-3-(imidazol-1-yl)-3-methyl-2-phenyl-prop-1-enyl]-benzoic acid (0.115 g), Yield=51%).

$^1$H NMR (DMSO $d_6$, 300 MHz) δ1.58(3H, d); 5.33(1H, q); 6.55(1H, s); 6.88(5H, m); 7.18(1H, s); 7.27(3H, m); 7.60(3H, d+s)

MS(ESP+) m/z 319 (MH+).

E) A mixture of product from step D (0.53 g, 1.67 mmol), EDC (0.32 g, 1.67 mmol) and HOBT(0.23 g, 1.67 mmol) was stirred in DMF (30 ml) until solution. This was then treated with L-methionine methyl ester hydrochloride (0.33 g, 1.67 mmol) and N-methylmorpholine (0.37 ml, 3.34 mmol), stirred for 18 hrs at room temperature and then treated with saturated aqueous NaHCO$_3$. The organic phase was evaporated to give the desired starting material (0.15 g, Yield=19.5%).

$^1$H NMR (DMSO $d_6$, 300 MHz) δ1.60(3H, d); 2.02(5H, s+m); 2.5(?, m);3.60(3H, s); 4.49(1H, q); 5.33(1H, q); 6.57(1H, d); 6.90(4H, m); 7.29(1H, s); 7.28(3H, m); 7.57 (3H, m); 8.58(1H, d).

MS(ESP+) m/z 464.1 (MH+).

EXAMPLE 7

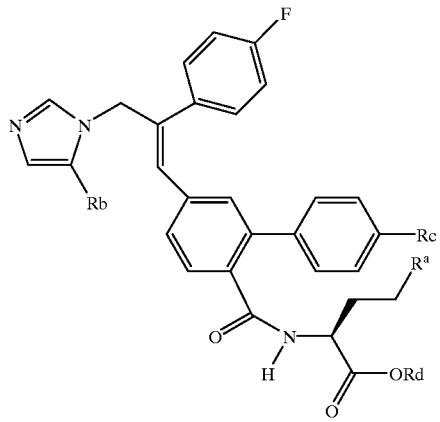

| Compound | $R^a$ | Rb | Rc | Rd | Yield |
|---|---|---|---|---|---|
| a) | $SCH_3$ | $CH_3$ | H | H | 30% |
| b) | $CONH_2$ | $CH_3$ | H | H | 50% |
| c) | $SCH_3$ | H | H | H | 61% |
| d) | $SCH_3$ | H | H | $CH_3$ | 32% |
| e) | $SCH_3$ | H | F | H | 35% |
| f) | $SCH_3$ | H | F | $CH_3$ | 68% |
| g) | $SCH_3$ | H | F | tButyl | 62% |
| h) | $SO_2CH_3$ | H | F | H | 70% |
| i) | $SO_2CH_3$ | H | F | $CH_3$ | 66% |
| j) | $SO_2CH_3$ | H | F | tButyl | 72% |
| k) | $SOCH_3$ | H | F | H | 74% |
| l) | $SOCH_3$ | H | F | $CH_3$ | 35% |
| m) | $SCH_3$ | H | F | N-methylpiperidin-4-yl | 70% |

Preparation of Compound a)

A) Compound a) was prepared from starting material methyl (2S)-2-{4-[(E)-2-(4-Fluorophenyl)-3-(5-methylimidazol-1-yl)-prop-1-enyl]-2-phenylbenzamido}-4-methylsulfanylbutyrate using the methodology as described in Example 1, compound a), step A. Yield=30%.

MP:116.5–117° C.

$^1$H NMR (CDCl$_3$, 400 MHz) δ1.7–2.2 (4H, m); 2.0 (3H, s); 2.12 (3H, s); 4.55 (1H, m); 4.78 (2H, s); 6.15 (1H, s); 6.40 (1H, s);6.8 (1H, s); 6.85–7.85 (14H, m).

Anal. calculated for $C_{31}H_{30}FN_3O_3S$, 0.9 $H_2O$ C, 66.50; H, 5.71; N, 7.51; S, 5.73.

Found: C, 66.84; H, 5.68; N, 7.54; S, 5.34.

MS (ESI) m/z: 544 (MH$^+$)

The starting material was prepared as follows.

B) To a solution of methyl 2-hydroxy-4-methylbenzoate (10 g; 60.2 mmol) in pyridine (150 ml) was added, under argon atmosphere, at 0° C., triflic anhydride (11.14 ml; 66.2 mmol). The mixture was stirred at room temperature for 1 hour. After evaporation of the pyridine, the residue was acidified to pH 3.5 with HCl 2N, and extracted with ether. The organic phase was evaporated and the residue purified by flash chromatography eluting with a gradient of 0–4% AcOEt/Petroleum ether to give methyl 2-trifluoromethylsulfonyloxy-4-methylbenzoate as an oil (43.8 g; 84%).

$^1$H NMR (CDCl$_3$, 400 MHz) δ2.45 (3H, s); 3.94 (3H, s); 7.09 (1H, s); 7.26 (1 H, s); 7.98 (1H, d).

C) To a suspension of product from step B (14 g; 47 mmol), 2M $Na_2CO_3$ (61.1 ml; 122.2 mmol) phenylboronic acid (6.3 g; 51.7 mmole) and LiCl (3.98 g; 94 mmol) in toluene (400 ml), was added, under argon atmosphere, a solution of tetrakis(triphenylphosphine)palladium (1.01 ml; 1.88 mmol) in THF (150 ml). The mixture was refluxed overnight, washed with 2N, NaOH and saturated NaCl. The organic phase was evaporated and the residue purified by flash chromatography (AcOEt/Petroleum ether: 95/5) to give methyl 4-methyl-2-phenylbenzoate as an oil (10.44 g; 98%).

$^1$H NMR (CDCl$_3$, 400 MHz) δ2.41 (3H, s); 3.61 (3H, s); 7.1–7.4 (7H, m); 7.76 (1H, d).

MS (ECI) m/z: 226 (M$^+$)

D) A solution of product from step C, (9.5 g; 42 mmol), N-bromosuccinimide (NBS) (8.22 g; 46.2 mmol), 2,2'-azobis(2'-methylpropionitrile) (25 mg; 0.15 mmol) and benzoylperoxide (25 mg; 0.1 mmol) in CCl$_4$ (100 ml) was heated at reflux for 5 hours. The solid was filtered and the filtrate evaporated to give methyl 4-bromomethyl-2-phenylbenzoate as an oil (9.43 g; 74%) which was used in the next step without further purification.

$^1$H NMR (CDCl$_3$, 400 MHz) δ3.63 (3H, s); 4.51 (2H, s); 7.1–7.5 (7H, m); 7.80 (1H, d).

E) A solution of product from step D) (9.43 g; 31 mmol) and triphenylphosphine (10.07 mg; 38 mmol) in toluene (100 ml) was refluxed for 1 hour 30 min. The resulting precipitate was filtered, and washed with ether to give 4-methyloxycarbonyl-3-phenyl-benzyltriphenylphosphonium bromide as a white solid (15.85 g; 90%).

$^1$H NMR (CDCl$_3$, 400 MHz) δ3.60 (3H, s); 5.68 (2H, d); 6.93 (2H, m); 7.2–7.9 (21H, m).

F) Product from step E was reacted with 1-(4-fluorophenyl)-2-(5-methylimidazol-1-yl)-ethanone using methodology as described in Example 4, compound a), step B and purified by flash chromatography eluting with CH$_2$Cl$_2$/EtOH (93/7) to give methyl 4-[2-(4-fluorophenyl)-3-(5-methylimidazol-1-yl)-prop-1-enyl]-2-phenyl-benzoate as an oil. Yield=76%.

$^1$H NMR (CDCl$_3$, 400 MHz) δ2.18 (3H, s); 3.58 (3H, s); 4.76 (2H, s); 6.23 (1H, s); 6.8–7.65 (14H, m).

G) Product from step F (1.54 g; 3.6 mmol) was heated at reflux in methanol (20 ml) and NaOH 2N, (4.5 ml) for 4 hours. Methanol was then evaporated and the solution acidified to pH 6.5. The resulting solid was filtered and dried to give 4-[2-(4-fluorophenyl)-3-(5-methylimidazol-1-yl)-prop-1-enyl]-2-phenyl-benzoic acid as a yellow powder (1.4 g; 94%).

$^1$H NMR (DMSO d$_6$+CDCl$_3$, 400 MHz) δ2.52 (3H, s); 5.32 (2H, s); 6.8–7.56 (14H, m); 8.94 (1H, s).

H) Product from step G was reacted with L-methionine methyl ester using methodology as described in Example 1, compound a), step E to give the desired starting material. Yield=57%.

MP:71–73° C.

$^1$H NMR (DMSO d$_6$, 400 MHz) δ1.7–2.1 (2H, m); 2.0 (3H, s); 2.15 (3H, s); 2.1–2.3 (2H, m); 3.32 (3H, s); 4.32 (1H, m); 4.98 (2H, s); 6.50 (1H, s); 6.88 (1H, s); 6.85–7.45 (13H, m); 8.6 (1H, d).

Anal. calculated for $C_{32}H_{32}FN_3O_3S$, 0.8 $H_2O$ C, 67.18; H, 5.92; N, 7.34; S, 5.60.

Found: C, 67.5; H, 16.06; N, 7.04; S, 5.47.

MS (ESI) m/z: 558 (MH$^+$)

Preparation of Compound b)

A) Compound b) was synthesised from the starting material tert-butyl (2S)-2-{4-[(E)-2-(4-fluorophenyl)-3-(5-methylimidazol-1-yl)-prop-1-enyl]-2-phenylbenzamido}-4-carbamoylbutyrate using methodology as described in Example 1, compound c), step A. Yield=50%.

MP:140–143° C.

$^1$H NMR (DMSO d$_6$+CF$_3$COOD, 400 MHz) δ1.7–2.15 (2H, m); 2.15–2.30 (2H, m); 2.31 (3H, s); 4.15 (1H, m), 5.32 (2H,s); 6.8–7.5 (15H,m); 8.6 (1H,d); 8.9 (2H,s).

Anal. calculated for $C_{31}H_{29}FN_4O_4$, 1.8 $H_2O$ C, 64.98; H, 5.73; N, 9.78.

Found: C, 64.96; H, 5.49; N, 9.71.

MS (ESI) m/z: 541 (MH$^+$)

B) The desired starting material was synthesised by reacting the product of step G, compound a) in this Example with L-glutamine tert-butyl ester using methodology as described in Example 1, compound c), step B. Yield=35%.

MP:96.5–97.5° C.

$^1$H NMR (CDCl$_3$, 400 MHz) δ1.37 (9H, s); 1.90–2.10 (2H, m); 2.15–2.20 (2H, m); 2.19 (3H,s); 4.39 (1H, m); 4.77 (2H, s); 5.25 (1H, s); 6.03 (1H, d); 6.24 (1H, s); 6.30 (1H, s); 6.80–7.45 (15H, m).

Anal. calculated for $C_{35}H_{37}FN_4O_4$, 0.7 $H_2O$ C, 68.99; H, 6.35; N, 9.19.

Found: C, 69.15; H, 16.80; N9.12.

MS (ESI) m/z: 597 (MH$^+$)

Preparation of Compound c)

Compound c) was prepared from compound d) using similar methodology to that described in Example 1, compound a), step A)

$^1$H NMR (DMSO+CF$_3$COOD, 400 MHz) δ1.8–1.87 (2H, m); 1.98 (3H, s); 2.18–2.26 (2H, m); 4.25–4.29 (1H, m); 5.34 (2H, s); 6.94–7.30 (13H, m); 7.65 (1H, s); 7.74 (1H, s); 8.5 (1H, d); 9.08 (1H, s).

Anal calcd for $C_{30}H_{28}FN_3O_3S$ C, 68.03; H, 5.33; N, 7.93; S, 6.05.

Found: C, 66.87; H, 5.48; N, 8.09; S, 5.83.

MS (ESI) m/z 530 (MH$^+$)

Preparation of Compound d)

The desired starting material was synthesised using similar methodology to that described for Example 7a, but using 1-(4-fluorophenyl)-2-(imidazol-1-yl)-ethanone in place of 1-(4-fluorophenyl)-2-(5-methylimidazol-1-yl)-ethanone $^1$H NMR (CDCl$_3$, 400 MHz) δ1.65–1.98 (2H, m); 2 (3H, s); 2.02–2.06 (2H, t); 3.65 (3H, s); 4.60–4.65 (1H, m); 4.87 (2H, s); 5.80–5.82 (1H, d); 6.52 (1H, s); 6.90–7.06 (8H, m); 7.15–7.17 (2H, m); 7.33–7.38 (3H, m); 7.42 (1H, s); 7.46–7.48 (1H, d).

The corresponding hydrochloride salt was prepared by treatment of the compound in solution in dichloromethane (2 ml) with a 3.8 N HCl solution in ether, diluting with ether (100 ml) and filtering of the resulting precipitate.

Anal. Calcd for $C_{31}H_{30}FN_3O_3S$, 1 HCl, 0.4 $H_2O$ C, 63.40; H, 5.46; N, 7.15; S, 5.46.

Found: C, 63.07; H, 5.48; N, 7.30; S, 5.32.

MS (ESI) m/z 544 (MH$^+$)

Preparation of Compound e)

Compound e) was prepared from compound f) using similar methodology to that described in Example 1, compound a), step A $^1$H NMR (DMSOd$_6$+CF$_3$COOD, 400 MHz) δ1.76–1.87 (2H, m); 1.97 (3H, s); 2.15–2.26 (2H, m); 4.2–4.24 (1H, m); 5.05 (2H, s); 6.69 (1H, s); 6.85 (1H, s); 6.90 (1H, s); 6.97–7 (1H, d)

Anal calcd for $C_{30}H_{27}F_2N_3O_3S$, $H_2O$ C, 63.70; H, 5.17; N, 7.43; S, 5.67.

Found: C, 63.90; H, 4.84; N, 7.34; S, 5.19.

MS (ESI) m/z 548 (MH$^+$).

Preparation of Compound f)

The desired starting material was synthesised using similar methodology to that described for compound d) but using 4-methoxycarbonyl-3-(4-fluorophenyl)-benzyltriphenylphosphonium bromide in place of 4-methoxycarbonyl-3-phenylbenzyltriphenylphosphonium bromide.

$^1$H NMR (CDCl$_3$, 400 MHz) δ1.88–2.09 (1H, m); 2.12 (3H, s); 2.25–2.28 (2H, t); 3.78 (3H, s); 4.75–4.8 (1H, m); 4.98 (2H, s); 6.01–6.03 (1H, d); 6.62 (1H, s); 6.98–7.26 (12 H, m); 7.52–7.55 (2H, m).

Anal calcd for $C_{21}H_{29}F_2N_3O_3S$, 0.2 $H_2O$, 1 HCl C, 61.88; H, 5.09; N, 6.98; S, 5.33.

Found: C, 61.50; H, 5.04; N, 7.06; S, 5.23.

MS (ESI) m/z 561 (MH$^+$).

Preparation of Compound g)

Compound g) was synthesised using similar methodology to that used to prepare compound f) but using the L-methionine t-butyl ester.

$^1$H NMR (CDCl$_3$, 400 MHz) δ1.40 (9H, s); 1.7–2.2 (4H, m); 2.03 (3H, s); 4.50 (1H, m); 4.87 (2H, s); 5.93 (1H, d); 6.51 (1H, s); 6.8–7.6 (14 H, m).

Anal calcd for $C_{34}H_{35}F_2N_3O_5S$, 0.18 $H_2O$ C, 67.28; H, 5.87; N, 6.92; S, 5.28.

Found: C, 67.14; H, 5.94; N, 6.71; S, 5.00.

MS (ESI) m/z 604 (MH$^+$)

Preparation of Compound h)

Compound h) was prepared from compound i) using similar methodology to that described in Example 1, compound a) step A $^1$H NMR (DMSOd$_6$+CF$_3$COOD, 400 MHz) δ1.9–2.3 (2H, m); 2.8–3.2 (2H, m); 2.94 (3H, s); 4.28–4.32 (1H, m); 5.35 (2H, s); 6.9–7.4 (12H, m); 7.65 (1H, s); 7.74 (1H, s); 8.7–8.8 (1H, d); 9.09 (1H, s).

Anal calcld for $C_{30}H_{27}F_2N_3O_5S$, 1.73 $H_2O$ C, 58.99; H, 5.03; N, 6.88; S, 5.25.

Found: C, 59.32; H, 5.10; N, 7.14; S, 5.16.

MS (ESI) m/z 580 (MH$^+$)

Preparation of Compound i)

Compound i) was synthesised using similar methodology to that described for compound d) but using the L-methionine sulfone methyl ester.

$^1$HNMR (CDCl$_3$, 400 MHz) δ1.94–2.05 (1H); 2.15–2.3 (1H, m); 2.6–2.9 (2H, m); 2.78 (3H, s); 3.62 (3H, s); 4.5–4.6 (1H, m); 4.8 (2H, s); 5.9–6 (1H, d); 6.43 (1H, s); 6.8–7.1 (12 H, m); 7.30–7.4 (2H, m).

Anal calcd for $C_{31}H_{29}F_2N_3O_5S$, 1.4 HCl C, 57.75; H, 4.75; N, 6.52; S, 4.97; Cl, 7.70.

Found: C, 57.94; H, 5.17; N, 6.41; S, 4.76; Cl, 8.07.

MS (ESI) m/z 594 (MH$^+$)

Preparation of Compound j)

Compound j) was synthesised using similar methodology to that used to prepared compound i) but using the L-methionine sulfone-tert-butyl ester.

$^1$H NMR (CDCl$_3$, 400 MHz) δ1.40 (9H, s); 1.9–2.1 (1H, m); 2.2–2.4 (1H, M); 2.6–2.9 (2H, m); 2.84(3H, s); 4.5 (1H, m); 4.9 (2H, s); 6 (1H, d); 6.5 (1H, s); 6.85–7.45 (14H, m).

Anal calcd for $C_{34}H_{35}F_2N_3O_5S$, 0.6 $H_2O$ C, 63.16; H, 5.64; N, 6.50; S, 4.96.

Found: C, 62.88; H, 5.67; N, 6.46; S, 4.57.

MS (ESI) m/z 636 (MH$^+$)

Preparation of Compound k)

Compound k) was prepared from compound 1) using analogous methodology to that described in Example 1, compound a), step A.

$^1$H NMR (DMSOd$_6$+CF$_3$COOD) δ1.8–2.2 (2H, m); 2.4–2.7 (2H, m); 2.5 (3H, m); 4.25 (1H, m); 5.35 (2H, s); 6.9–7.35 (12H, m); 7.65–7.8 (2H, m); 8.65 (1H, d); 9.08 (1H, s).

Anal calcd for $C_{30}H_{27}F_2N_3O_4S$, 2.15 $H_2O$ C, 59.82; H, 5.24; N, 6.98; S, 5.32.

Found: C, 60.18; H, 5.04; N, 7.33; S, 5.16.

MS (ESI) m/z 564 (MH$^+$)

Preparation of Compound l)

Compound l) was synthesised using similar methodology to that described for compound d) but using the L-methionine sulfoxide methyl ester.

¹H NMR (DMSOd₆+CF₃COOD) δ1.8–2.15 (2H, m); 2.3–2.7 (2H, m); 2.50 (3H, s); 3.64 (3H,s); 4.35 (1H, m); 5.35 (2H, s); 6.9–7.35 (12H, m); 7.6–7.8 (2H, m); 9.1 (1H, s).

Anal calcd for $C_{31}H_{29}F_2N_3O_4S$, 0.70 $H_2O$, 1.2 HCl C, 58.73; H, 5.02; N, 6.63; S, 5.06; Cl, 6.71.

Found: C, 58.82; H, 5.41; N, 6.68; S, 4.66; Cl, 6.53.

MS (ESI) m/z 578 (MH⁺)

Preparation of Compound m)

Compound (m) was synthesised using similar methodology to that used to prepare compound d) but using the L-methionine 4-(N-methylpiperidine)ester.

¹H NMR (CDCl₃, 400 MHZ) δ1.6–2.1 (6H, m); 2.01 (3H, s); 2.1–2.35 (2H, m); 2.26 (3H, s); 2.6 (2H, s); 4.5–4.8 (2H, m); 4.87 (2H, s); 5.9 (1H, d); 6.5 (1H, s); 6.85–7.45 (14H, m).

Anal calcd $C_{36}H_{38}F_2N_4O_3S$ C, 67.06; H, 5.94; N, 8.69; S, 4.97.

Found: C, 66.72; H, 6.21; N, 8.47; S, 4.58.

MS (ESI) m/z 645 (MH⁺).

EXAMPLE 8

Preparation of a) (2S)-2-{4-[(Z)-3-(imidazol-1-yl)-2-(thiazol-2-yl)-prop-1-enyl]-2-phenyl-benzamido}-4-methylsulfanylbutyric acid b) (2S)-2-{4-[(Z)-3-(imidazol-1-yl)-2-(thiazol-2-yl)-prop-1-enyl]-2-phenyl-benzamido}-4-carbamoylbutyric acid; and c) (2S)-2-{4-[3-(imidazol-1-yl)-2-(thiazol-2-yl)-propyl]-2-phenyl-benzamido}-4-carbamoylbutyric acid

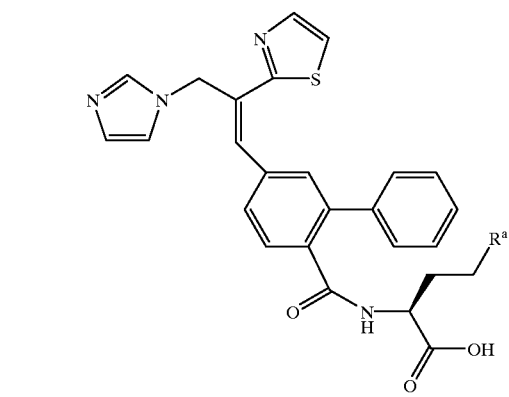

| Compound | Rᵃ |
|---|---|
| a) | SCH₃ |
| b) | CONH₂ |
| compound c) | |

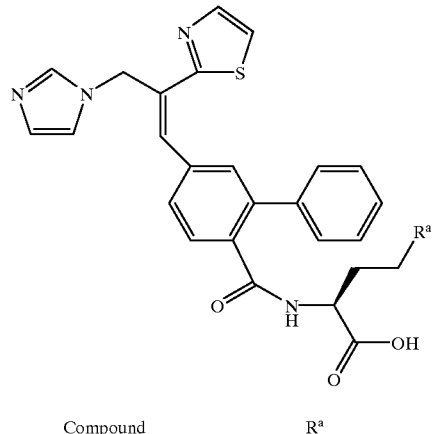

| Compound | Rᵃ |

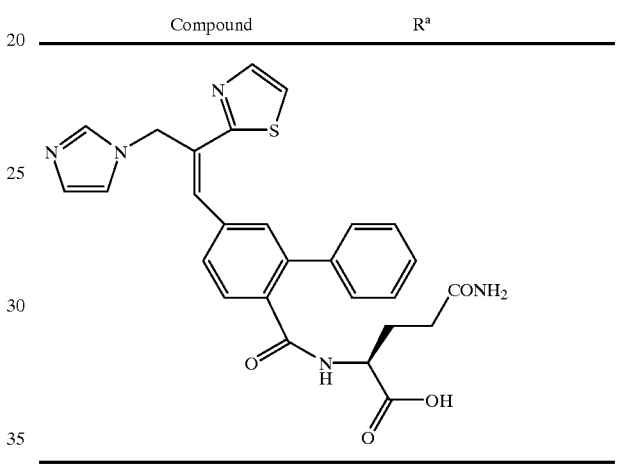

Preparation of Compound a)

A) Compound a) was obtained by deprotection of starting material methyl (2S)-2-{4-[(Z)-3-(imidazol-1-yl)-2-(thiazol-2-yl)-prop-1-enyl]-2-phenyl-benzamido}-4-methylsulfanylbutyrate using methodology as described in Example 1, compound a), step A.
Yield=92%.
MP:122–124° C.

¹H NMR (DMSO d₆+CF₃COOD) δ1.8–2.1 (2H, m); 2.0 (3H, s); 2.2–2.4 (2H, m); 4.32 (1H, m); 5.48 (2H, s); 7.3–7.55 (8H, m); 7.65–7.90 (4H, m); 8.62 (1H, d); 9.26 (1H, s).

Anal. calculated for $C_{27}H_{26}N_4O_3S_2$, 0.9 $H_2O$ C, 60.63; H, 5.24; N, 10.47; S, 11.99.

Found: C, 61.04; H, 5.24; N, 10.22; S, 11.77.

MS (ESI) m/z: 519 (MH⁺)

The starting material was obtained as follows.

B) To a mixture of 2-(imidazol-1-yl)-1-(thiazol-2-yl) ethanone (1.66 g; 8.5 mmol), 4-methyloxycarbonyl-3-phenyl-benzyl-triphenylphosphonium bromide (see Example 7, compound a), step E), (7.3 g; 12.8 mmol) and 18-crown-6 (0.1 g; 0.37 mmol) in methylene chloride (60 ml) was added at −50° C., under argon atmosphere, potassium tert-butoxide (1.56 g; 12.8 mmol). After 20 min at −50° C., the mixture was stirred at room temperature for 4 hours. The solvent was evaporated to dryness and the residue purified on HP20SS resin eluting with a gradient of 0–60% CH₃CN/(NH₄)₂CO₃ buffer (2 g/l pH 6.8) to give methyl 4-[(Z)-3-(imidazol-1-yl)-2-(thiazol-2-yl)-prop-1-enyl]-2-phenyl-benzoate (1.1 g; 72%).

¹H NMR (CDCl₃, 400 MHz) δ3.63 (3H, s); 5.21 (2H, s); 6.70 (1H, s); 7–7.4 (10H, m); 7.59 (1H, s); 7.79 (2H, m).

C) Product from step B was deprotected using methodology as described in Example 7, compound a), step G to give 4-[(Z)-3-(imidazol-1-yl)-2-(thiazol-2-yl)-prop-1-enyl]-2-phenyl-benzoic acid. Yield=65%.

$^1$H NMR (DMSO D$_6$+CF$_3$COOD) δ5.48 (2H, s); 7.2–8.1 (14H, m).

D) Product from step C was reacted with L-methionine methyl ester using methodology as described in Example 1, compound a, step E to give the desired starting material. Yield=41%.

MP:100–101° C.

$^1$H NMR (CDCl$_3$, 400 MHz) δ1.8–2.2 (4H, m); 2.01(3H, s); 3.68 (3H, s); 4.68 (1H, m); 5.44 (2H, s); 6 (1H, d); 7.2–7.5 (11H, m); 7.70–7.80 (2H, m); 8.85 (1H, s).

Anal. calculated for C$_{28}$H$_{28}$N$_4$O$_3$S$_2$, 1.31 H$_2$O C, 60.48; H, 5.55; N, 10.07; S, 11.53.

Found: C, 58.75; H, 5.55; N, 9.55; S, 10.86.

MS (ESI) m/z: 593 (MH$^+$)

Preparation of Compound b)

A) Starting material tert-butyl (2S)-2-{4-[(Z)-3-(imidazol-1-yl)-2-(thiazol-2-yl)-prop-1-enyl]-2-phenyl-benzamido}-4-carbamoylbutyrate was deprotected using methodology as described in Example 1, compound c), step A. Yield=84%.

$^1$H NMR (DMSO d$_6$+CF$_3$COOD) δ1.7–2.2 (4H, m); 4.18 (1H, m); 5.48 (2H, s); 7.3–7.9 (13H, m); 8.72 (1H, m); 9.26 (1H, s).

Anal. calculated for C$_{27}$H$_{25}$N$_5$O$_4$S, 1.5 H$_2$O C, 59.75; H, 5.20; N, 12.90; S, 5.91.

Found: C, 59.21; H, 5.05; N, 12.69; S, 5.46.

MS (ESI) m/z: 516 (MH$^+$)

B) The starting material was prepared by reacting 4-[(Z)-3-(imidazol-1-yl)-2-(thiazol-2-yl)-prop-1-enyl]-2-henyl-benzoic acid (see this Example, compound a), step C) with L-glutamine tert-butyl ester using methodology as described in Example 1, compound c) step B.

Yield=26%.

$^1$H NMR (DMSO d$_6$+CF$_3$COOD) δ1.42 (9H, s); 1.7–2.0 (2H, m); 2.12 (2H, m); 4.15 (1H, m); 5.48 (2H, s); 7.2–7.8 (13H, m); 8.72 (1H, d); 9.26 (1H, s).

Anal. calculated for C$_{31}$H$_{33}$N$_5$O$_4$S, 1.5 H$_2$O C, 62.19; H, 16.06; N, 11.70; S, 5.36.

Found: C, 60.54; H, 5.83; N, 9.71; S, 4.72.

MS (ESI) m/z: 572 (MH$^+$)

Preparation of Compound c)

A) Starting material tert-butyl (2S)-2-{4-[3-(imidazol-1-yl)-2-(thiazol-2-yl)-propyl]-2-phenyl-benzamido}-4-carbamoylbutyrate was deprotected using methodology as described in Example 1, compound c), step A to give the desired end product. Yield=95%.

$^1$H NMR (DMSO d$_6$+CF$_3$COOD, 400 MHz) δ1.7–2.25 (4H, m); 3.20 (2H, m); 4.16 (1H, m); 4.31 (1H, m); 4.68 (2H, m); 7.1–7.8 (12H, m); 8.55 (1H, d); 9.03 (1H, s).

Anal. calculated for C$_{27}$H$_{27}$N$_5$O$_4$S, 1.4 H$_2$O C, 59.74; H, 5.53; N, 12.90.

Found: C, 59.65; H, 5.31; N, 12.65.

MS (ESI) m/z: 518 (MH$^+$)

The starting material was prepared as follows.

B) A suspension of methyl 4-[(Z)-3-(imidazol-1-yl)-2-(thiazol-2-yl)-prop-1-enyl]-2-phenyl-benzoate (see this Example, compound a), step B) (1.2 g; 3 mmol) and 10% Pd/C (0.3 g) in MeOH (10 ml) was hydrogenated for 6 hours. After filtration of the catalyst and evaporation to dryness the residue was purified by flash chromatography eluting with CH$_2$Cl$_2$/EtOH (98/2) to give methyl 4-[3-(imidazol-1-yl)-2-(thiazol-2-yl)-propyl]-2-phenyl-benzoate. Yield=25%.

$^1$H NMR (CDCl$_3$, 400 MHz) δ3–3.3 (2H, m); 3.62 (3H, s); 3.7–3.82 (1H, m); 4.3–4.55 (2H, m); 5.2(1H, s); 6.7–8 (13H, m)

C) Product from step B (0.39 g; 0.96 mmol) and NaOH 2N, (1.25 ml) in MeOH (8 ml) was heated at reflux for 2 hours. After evaporation of the solvent and neutralisation at pH6, the residue was purified on reverse phase silica eluting with MeOH/(NH$_4$)$_2$CO$_3$ buffer (2 g/l, pH7) 20/80 to give 4-[3-(imidazol-1-yl)-2-(thiazol-2-yl)-propyl]-2-phenyl-benzoic acid.

$^1$H NMR (DMSO d$_6$+CF$_3$COOD) δ3.15 (2H, m); 4.25 (1H, m); 4.65 (2H, m); 7.1–7.8 (13H, m); 9.1 (1H, s).

D) Product from step C was reacted with L-glutamine tert-butyl ester using methodology as described in Example 1, compound c), step B to give the desired starting material. Yield=63%.

$^1$H NMR (CDCl$_3$, 400 MHz) δ1.39 (9H, s); 1.35–1.75 (2H, m); 2.05 (2H, m); 3–3.30 (2H, m); 3.8 (1H, m); 4.3–4.5 (2H, m); 5.28 (1H, s); 6.1 (1H, m); 6.7 (1H, s); 6.9–7.45 (10H, m); 7.52 (1H, d); 7.79(1H, m).

Anal. calculated for C$_{31}$H$_{35}$N$_5$O$_4$S, 1.1 H$_2$O C, 62.73; H, 6.32; N, 11.80.

Found: C, 63.10; H, 6.30; N, 11.53.

MS (ESI) m/z: 574 (MH$^+$)

EXAMPLE 9

Preparation of a) (2S)-2-{4-[2-(4-Fluorophenyl)-3-(5-methylimidazol-1-yl)-propyl]-2-phenyl-benzamido}-4-methylsulfanylbutyric acid; and b) (2S)-2-{4-[2-(4-Fluorophenyl)-3-(5-methylimidazol-1-yl)-propyl]-2-phenyl-benzamido}-4-carbamoylbutyric acid

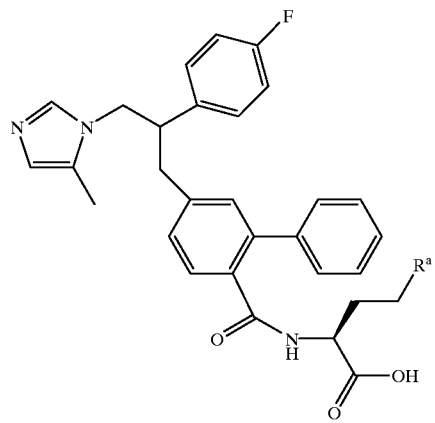

| Compound | R$^a$ |
|---|---|
| a) | SCH$_3$ |
| b) | CONH$_2$ |

Preparation of Compound a)

A) Starting material methyl (2S)-2-{4-[2-(4-Fluorophenyl)-3-(5-methylimidazol-1-yl)-propyl]-2-phenyl-benzamido}-4-methylsulfanylbutyrate was deprotected using methodology as described in Example 1, compound a), step A to give the desired end product. Yield=81%.

MP: 121–124° C.

$^1$H NMR (CDCl$_3$, 400 MHz) δ1.6–2.35 (4H, m); 1.73 and 1.78 (3H, s); 2.01 (3H, s); 2.9–3.4 (3H, m); 3.8–4.25 (2H, m); 4.55 (1H, m); 6.25 and 6.32 (1H, d); 6.6–7.8 (14H, m).

Anal. calculated for $C_{31}H_{32}FN_3O_3S$, 0.5 $H_2O$ C, 67.13; H, 6.00; N, 7.58; S, 5.78.

Found: C, 67.18; H, 6.24; N, 7.78; S, 5.54.

MS (ESI) m/z: 546 (MH$^+$)

The starting material was prepared as follows.

B) A suspension of E and Z isomers of methyl 4-[2-(4-fluorophenyl)-3-(5-methylimidazol-1-yl)-prop-2-enyl]-2-phenyl-benzoate (2 g; 4.69 mmol) and 10% Pd/C (0.55 g) in MeOH (25 ml) was hydrogenated for 22 hours. After filtration of the catalyst, the solvent was evaporated to give methyl 4-[2-(4-fluorophenyl)-3-(5-methylimidazol-1-yl)-propyl)-2-phenyl-benzoate as an oil which was used in the next step without further purification.

C) Product from step B in solution in methanol (25 ml) was treated at reflux for 2 hours with NaOH 2N (5.8 ml). After evaporation to dryness and neutralisation at pH6 with 6N HCl, the resulting solid was filtered and purified on reverse phase silica eluting with MeOH/(NH$_4$)$_2$CO$_3$ buffer (2 g/l, pH7) 40/60 to give 4-[2-(4-fluorophenyl)-3-(5-methylimidazol-1-yl)-propyl]-2-phenyl-benzoic acid.

$^1$H NMR (DMSO d$_6$+CF$_3$COOD) δ2.12 (3H, s); 3.12–3.19 (2H, m); 3.62 (1H, m); 4.32–4.45 (2H, m); 7.05–7.61 (13H, m); 8.77 (1H, s).

D) Product from step C was reacted with L-methionine methyl ester using methodology as described in Example 1, compound a), step E to give the desired starting material. Yield=26%.

$^1$H NMR (CDCl$_3$, 400 MHz) δ1.6–2.2 (10H, m); 3.03 (2H, m); 3.20 (1H, m); 3.65 (3H, s); 3.9–4.20 (2H, m); 4.64 (1H, m); 5.82 (1H, m); 6.60–7.70 (14H, m).

Anal. calculated for $C_{32}H_{34}N_3O_3S$, 0.5 $H_2O$ C, 67.58; H, 6.02; N, 7.39; S, 5.64.

Found: C, 67.55; H, 6.31; N, 7.51; S, 5.24.

MS (ESI) m/z: 560 (MH$^+$)

Preparation of Compound b)

A) The desired end product was prepared by deprotecting starting material tert-butyl (2S)-2-{4-[2-(4-fluorophenyl)-3-(5-methylimidazol-1-yl)-propyl]-2-phenyl-benzamido}-4-carbamoylbutyrate using methodology as described in Example 1, compound c), step A. Yield=81%.

MP: 132–134° C.

$^1$H NMR (DMSO d$_6$+CF$_3$COOD, 400 MHz) δ1.7–2.05 (2H, m); 2.06 (3H, s); 2.05–2.20 (2H, m); 3.1–3.3 (2H, m); 3.65 (1H, m); 4.17 (1H, m); 4.32–4.55 (2H, m); 7–7.4 (13H, m); 8.77 (1H, s).

Anal. calculated for $C_{31}H_{31}FN_4O_4$, 2.2 $H_2O$ C, 63.95; H, 6.13; N, 9.62.

Found: C, 63.54; H, 5.80; N, 9.71.

MS (ESI) m/z: 543 (MH$^+$)

B) The starting material was prepared by reacting 4-[2-(4-fluorophenyl)-3-(5-methylimidazol-1-yl)-propyl]-2-phenyl-benzoic acid (see this Example, compound a), step C) with L-glutamine tert-butyl ester using methodology as described in Example 1, compound c), step B. Yield=57%.

MP: 93–95° C.

$^1$H NMR (CDCl$_3$, 400 MHz) δ1.38 (9H, s); 1.25–1.7 (2H, m); 1.95–2.15 (5H, m); 3.03 (2H, m); 3.20 (1H, m); 3.9–4.15 (2H, m); 4.42 (1H, m); 5.27 (1H, s); 6.68 (1H, s); 6.9–7.6 (13H, m).

Anal. calculated for $C_{35}H_{39}FN_4O_4$, 1.5 $H_2O$ C, 67.18; H, 6.77; N, 8.95.

Found: C, 67.46; H, 8.67; N, 7.11.

EXAMPLE 10

Preparation of a) (2S)-2-{3-[(Z)-2-(4-Fluorophenyl)-4-(imidazol-1-yl)-but-1-enyl]-benzamido}-4-methylsulfanylbutyric acid; and b) (2S)-2-{3-[(E)-2-(4-Fluorophenyl)-4-(imidazol-1-yl)-but-1-enyl]-benzamido}-4-methylsulfanylbutyric acid

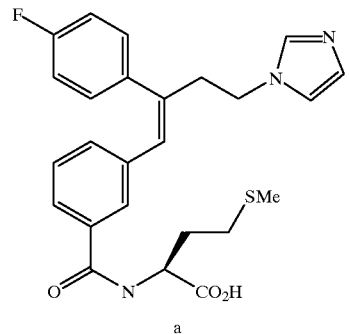

a

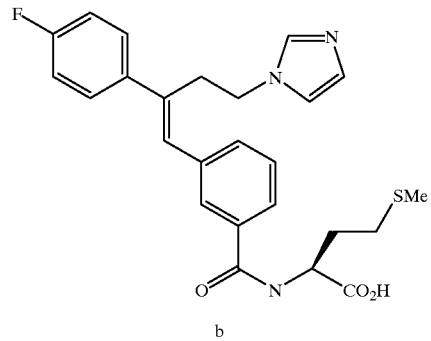

b

Preparation of Compound a)

A) Starting material methyl (2S)-2-{3-[(Z)-2-(4-Fluorophenyl)-4-(imidazol-1-yl)-but-1-enyl]-benzamido}-4-methylsulfanylbutanoate 0.52 g, (1.08 mmol) was hydrolysed and purified according to methodology as set out in step E below to give the desired end product as a white solid 0.48 g (95%).

$^1$H NMR (DMSO, 300 MHz) d2.00 (2H, m); 2.03 (3H, s); 2.56 (2H, m); 3.03 (2H, t); 4.10 (2H, t); 4.45 (1H, m); 6.50 (1H, s); 6.85 (1H, d); 7.43 (5H, m); 7.58 (2H, m); 7.59 (1H, d); 8.20 (1H, m); 8.48 (1H, d).

MS (ESP+) m/z 468 (M+H)$^+$.

Preparation of Compound b)

A) Starting material methyl (2S)-2-{3-[(E)-2-(4-fluorophenyl)-4-(imidazol-1-yl)-but-1-enyl]-benzamido}-4-methylsulfanylbutanoate (0.08 g, 0.166 mmol) was similarly hydrolysed and purified to give the desired end product 0.07 g (90%) as a white solid.

$^1$H NMR (DMSO, 300 MHz) d2.04 (3H, s); 2.08 (2H, m); 2.54 (2H, m); 3.08 (2H, t); 3.99 (2H, t); 4.53 (1H, m); 6.84 (1H, s); 6.88 (1H, s); 7.03 (1H, s); 7.22 (3H, m); 7.44 (1H, t); 7.52 (1H, s); 7.63 (2H, m); 7.76 (1H, s); 8.63 (1H, d, J 9 Hz).

MS (ESP+) m/z 468 (M+H)$^+$.

Starting materials for compounds a) and b) were prepared as follows.

B) A suspension of 4-fluoroacetophenone (8.8 ml, 72.4 mmol), paraformaldehyde (2.9 g, 94.1 mmol), dimethylamine hydrochloride (7.8 g, 96.78 mmol) conc. HCl (1 ml)

in ethanol (10 ml) was heated under reflux for 3 hrs. The solution was added to acetone (50 ml), allowed to cool and placed in the fridge overnight. The resulting white solid was filtered washed with acetone (100 ml) and dried over $P_2O_5$ under vacuum to give 1-(4-fluorophenyl)-3-(N,N-dimethylamino)propanone hydrochloride 7.82 g, (51%).

$^1$H NMR (CDCl$_3$, 300 MHz) d2.86 (6H, s); 3.53 (2H, t); 3.74 (2H, t); 7.17 (2H, m); 8.07 (2H, m)

MS (ESP+) m/z 196 (M+H)$^+$.

C) A solution of product from step B (7.80 g, 36.6 mmol) in ethanol (30 ml) and water (30 ml) containing imidazole (12.4 g, 183.0 mmol) was heated under reflux for 6 hrs. The mixture was allowed to cool and partitioned between dichloromethane (100 ml) and water (100 ml), the organic phase was washed with brine (5×100 ml) separated and dried (MgSO$_4$). Evaporation of the residue left a yellow oil. This was purified by chromatography (Biotage flash 40, 90 g, SiO$_2$ cartridge) eluting with a gradient of 0–5% methanol/dichloromethane to give 1-(4-fluorophenyl)-3-(imidazol-1-yl)propanone as a yellow oil 4.32 g (54%).

$^1$H NMR (CDCl$_3$, 300 MHz) d3.32 (2H, t); 4.33 (2H, t); 6.89 (1H, s); 6.92 (1H, s); 7.02 (2H, t); 7.45 (1H, s); 7.84 (2H, m).

MS (ESP+) m/z 219 (M+H)$^+$.

D) To a solution of product from step C (2.00 g, 9.17 mmol) in dichloromethane (25 ml) was added 3-methoxycarbonylbenzyltriphenylphosphonium bromide (4.50 g, 9.17 mmol) and potassium tert-butoxide (1.03 g, 9.17 mmol). The mixture was stirred at room temperature for 18 hrs. A further portion of the phosphonium salt (0.88 g, 1.83 mmol) and potassium tert-butoxide (0.21 g, 1.83 mmol) was added. After 16 hrs at room temperature the mixture was partitioned between brine (50 ml) and dichloromethane (50 ml). The organic phase was washed with brine (2×50 ml) and dried (MgSO$_4$). Evaporation of the solvent left an orange gum which was purified by column chromatography on SiO$_2$ (Merck 9385) eluting EtOAc/ammonia (1%) to give methyl 3-[2-(4-fluorophenyl)-4-(imidazol-1-yl)-but-1-enyl]-benzoate as Z isomer 0.57 g (18%), E isomer 0.38 g (12%) and a mixture of isomers 0.65 g (20%) as a yellow gum.

Z isomer $^1$H NMR (CDCl$_3$, 300 MHz) d2.94 (2H, t); 3.84 (3H, s); 3.94 (2H, t); 6.37 (1H, s); 6.89 (1H, s); 7.07 (7H, m); 7.40 (1H, s); 7.58 (1H, s); 7.75 (1H, d).

MS (ESP+) m/z 351 (M+H)$^+$.

E isomer $^1$H NMR (CDCl$_3$, 300 MHz)d3.10 (2H, t); 3.95 (3H, s); 3.97 (2H, t); 6.74 (1H, s); 6.80 (1H, s); 6.97 (1H, s); 7.12 (3H, t); 7.29 (1H, s); 7.55 (3H, m); 7.87 (1H, s); 7.93 (1H, d).

MS (ESP+) m/z 351 (M+H)$^+$.

E) A solution of Z isomer product from step D (0.64 g, 1.83 mmol) in MeOH (2 ml) was treated with 1N NaOH (2 ml). The resulting suspension was stirred at room temperature for 20 hrs and the acidity adjusted to pH 5 with 1N HCl. The solution was evaporated to dryness and the residue purified by chromatography isolute column (10 g, SiO$_2$) with an eluent of dichloromethane/MeOH (9:1) to give 3-[(Z)-2-(4-fluorophenyl)-4-(imidazol-1-yl)-but-1-enyl]-benzoic acid 0.56 g, (91%) as a white solid.

$^1$H NMR (DMSO, 300 MHz) d3.10 (2H, t); 3.99 (2H, t); 6.82 (1H, s); 6.88 (1H, s); 7.01 (1H, s); 7.26 (3H, m); 7.46 (2H, t); 7.62 (2H, m); 7.82 (1H, s); 7.84 (1H, s).

MS (ESP+) m/z 337 (M+H)$^+$.

The corresponding E isomer was prepared in 76% yield as a white solid from the E isomer product from step D (0.34 g, 0.971 mmol).

$^1$H NMR (DMSO, 300 MHz) d2.99 (2H, t); 3.96 (2H, t); 6.45 (1H, s); 6.87 (1H, s); 6.98 (1H, d); 7.16 (5H, m); 7.22 (1H, t); 7.43 (1H, s); 7.55 (1H, s); 7.63 (1H, d).

MS (ESP+) m/z 337 (M+H)$^+$.

F) To a mixture of E and Z isomers from step E (0.34 g, 1.01 mmol), EDC (0.19 g, 1.01 mmol) and HOBt (0.14 g, 1.01 mmol) in dichloromethane (20 ml) was added L-methionine methyl ester hydrochloride (0.20 g, 1.01 mmol) and 4-methylmorpholine (0.11 ml, 1.01 mmol). The mixture was allowed to stir at room temperature for 18 hrs, washed with brine (3×50 ml), the organic phase separated, dried over (MgSO$_4$) and the solvent evaporated to give a yellow gum. This was then purified by flash chromatography on SiO$_2$ (Merck 9385) eluting EtOAc/0.88 aqueous ammonia (1%) to give the desired starting materials as pure Z isomer 0.13 g (27%), pure E isomer 0.08 g (16%) and a mixture of isomers 0.08 g (16%).

Z isomer $^1$H NMR (CDCl$_3$, 300 MHz) d2.11 (3H, s); 2.28 (2H, m); 2.52 (2H, t); 2.97 (2H, t); 3.78 (3H, s); 3.97 (2H, t); 4.85 (1H, m); 6.37 (1H, s); 6.89 (1H, s); 7.05 (1H, s); 7.13 (5H, m); 7.42 (4H, m), 7.56 (1H, d).

MS (ESP+) m/z 482 (M+H)$^+$.

E isomer $^1$H NMR (CDCl$_3$, 300 MHz) d2.13 (3H, s); 2.31 (2H, m); 2.65 (2H, t); 3.03 (2H, t); 3.82 (3H, s); 3.94 (3H, t); 4.94 (1H, m); 6.66 (1H, s); 6.79 (1H, s); 6.97 (1H, s); 7.13 (5H, m); 7.38 (4H, m); 7.73 (1H, d).

MS (ESP+) m/z 482 (M+H)$^+$.

EXAMPLE 11

Preparation of methyl (2S)-2-{3-[(E)-2-(4-fluorophenyl)-3-(imidazol-1-yl)-prop-1-enyl]-benzamido}-2-methyl-4-methylsulfanylbutanoate

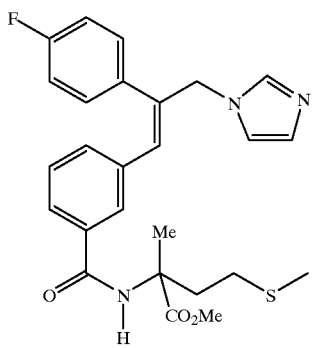

To a mixture of 3-((E)-2-(4-fluorophenyl)-3-(imidazol-1-yl)-prop-1-enyl)benzoic acid (0.50 g, 1.55 mmol; prepared as the product of step D in Example 1), EDC (0.30 g, 1.55 mmol) and HOBt (0.21 g, 1.55 mmol) in dichloromethane (20 ml) was added α-methyl methionine methyl ester (0.33 g, 1.55 mmol) and 4-methylmorpholine (0.17 ml, 1.55 mmol). The solution was stirred at room temperature for 17 hrs, washed with brine (3×40 ml) dried over (MgSO$_4$) and the solvent evaporated to leave a yellow gum. This was purified by chromatography (Biotage flash 40, 40 g SiO$_2$ cartridge) eluting a gradient of 0–1% 0.88 aqueous ammonia/EtOAc to give the desired end product as a yellow gum 0.38 g (50%).

$^1$H NMR (CDCl$_3$, 300 MHz) δ1.65 (3H, s); 2.05 (3H, s); 2.24 (2H, m); 2.49 (1H, m); 2.71 (1H, m); 4.82 (3H, s); 4.87 (2H, s); 6.55 (1H, s); 7.87 (7H, m); 7.21 (1H, t); 7.37 (1H, s); 7.50 (1H, s); 7.58 (1H, d).

MS (ESP+) m/z 482 (M+H)$^+$.

α-Methyl methionine methyl ester was made according to the methodology of A. Boumendjel and S. P. F. Millar, Tetrahedron Lett., 1994, 35, 819.

EXAMPLE 12

Preparation of (2S)-2-{4-[(E)-2-(4-Fluorophenyl)-3-(imidazol-1-yl)-prop-1-en-1-yl]benzamido}-4-methylsulfanylbutyric acid

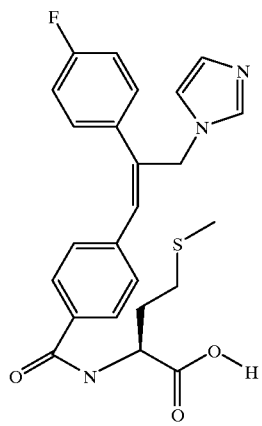

A) The title compound was prepared from methyl (2S)-2-{4-[(E)-3-(imidazol-1-yl)-2-(4-fluorophenyl-2-yl)-prop-1-enyl]benzamido}-4-methylsulfanylbutyrate using similar methodology to that described in Example 1, compound a), step A).

Yield: 61%

Melting point: 106° C.

$^1$H NMR (DMSOd$_6$+CF$_3$COOD, 400 MHz) δ2–2.15 (2H, m); 2.13 (3H, s); 2.45–2.7 (2H, m); 4.55 (1H, m); 5.54 (2H, s); 7.15–7.30 (3H, m); 7.5–7.7-6H, m); 8 (2H, d); 9.10 (1H, s)

Anal calculated for C$_{24}$H$_{24}$FN$_3$O$_3$S, H$_2$O C, 61.1; H, 5.56; N, 8.91; S, 6.80.

Found: C, 61.34; H, 5.53; N, 9.15; S, 6.54.

MS (ESI) m/z 454 (MH)$^+$

The starting material was prepared as follows:

B) Methyl 4-(2-(4-fluorophenyl)-3-(imidazol-1-yl)prop-1-en-1-yl)benzoate was prepared in a similar manner to that described in Example 1, compound a), step B, but using 4-(methoxycarbonylbenzyl)-triphenylphosphonium bromide (obtained as a E and Z mixture).

Yield 70%

C) A solution of the product from step B (E and Z isomers) (2.3 g, 6.8 mmol) in methanol (50 ml) was treated with 2N aqueous sodium hydroxide solution (7 ml, 14 mmol) for 1 hour. Methanol was then evaporated and the solution was acidified to pH 5.5 with 6N HCl. The resulting precipitate was triturated in ether and filtered to give 4-(-2-(4-fluorophenyl)-3-(imidazol-1-yl)-prop-1-en-1-yl)benzoic acid as a mixture of E and Z isomers 1.4 g (65%).

D) A mixture of E and Z isomers from step C (0.65 g, 2 mmol), L-methionine methyl ester hydrochloride (0.4 g, 2 mmol), HOBT (0.27 g, 2.2 mmol), EDC (0.42 g, 2.2 mmol) and N-methylmorpholine (0.24 ml, 2.2 mmol) in dichloromethane (20 ml) was stirred at room temperature for 1 hour, and then washed with saturated sodium hydrogencarbonate solution (aqueous). The organic phase was evaporated and the residue purified on reverse phase silica eluting a gradient of 50–60% methanol/(NH$_4$)$_2$CO$_3$ buffer (2 g/l pH 7). Appropriate fractions were evaporated, extracted with dichloromethane and evaporated to give the methyl (2S)-2-{4-[(E)-2-(4-fluorophenyl)-3-(imidazol-1-yl)-prop-1-en-1-yl]benzamido}-4-methylsulfanylbutanoate as a foam.

Melting Point=54–57° C.

$^1$H NMR (CDCl$_3$, 400 MHz) 2–2.3 (2H, m); 2.03 (3H, s); 2.5–2.6 (2H, m); 3.80 (3H, s); 4.83 (3H, m); 6.52 (1H, s); 6.8–7.1 (8H, m); 7.42 (1H, s); 7.5–7.6 (2H, m)

Anal calcd for C$_{25}$H$_{26}$FN$_3$O $_3$S, 0.35 H$_2$O C, 63.37; H, 5.68; N, 8.87; S, 6.77.

Found: C, 63.24; H, 5.70; N, 9.05; S, 6.65.

MS (ESI) m/z 468 (MH$^+$).

EXAMPLE 13

Preparation of 1-(morpholin-4-yl)prop-2-yl (2S)-2-{3-[E-2-(4-fluorophenyl)-3-(imidazol-1-yl)prop-1-en-1-yl]benzamido}-4-methylsulfanylbutyrate

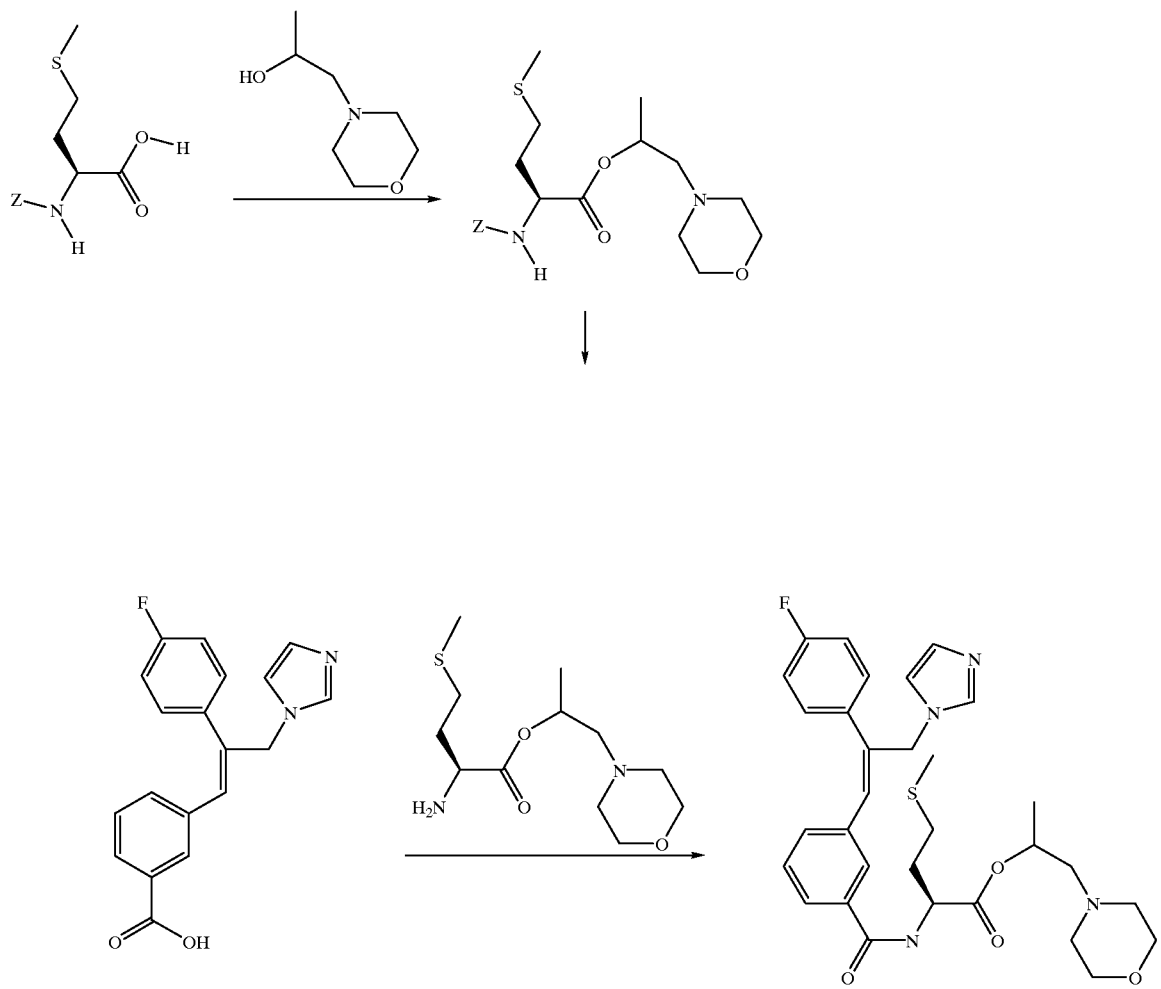

The title compound was synthesised in a similar manner to that described in Example 1, compound a), step E, but using 1-(morpholino)prop-2-yl 2-amino-4-methylsulfanylbutyrate in place of the L-methionine methyl ester.

$^1$H NMR (CDCl$_3$, 400 MHz) δ1.2–1.3 (3H, m); 2–2.7 (10H, m); 2.1 (3H, s); 3.6 (4H, s); 4.8–4.9 (3H, m); 5.1–5.3 (1H, m); 6.55–6.65 (2H, m); 6.9–7.7 (11H, m)

Anal calcd for C$_{31}$H$_{37}$FN$_4$O$_4$S, 0.96 H$_2$O C, 62.26; H, 6.56; N, 9.37; S, 5.36.

Found: C, 62.39; H, 6.73; N, 9.57; S, 5.08.

MS (ESI) m/z 581 (MH$^+$).

The starting material was prepared as follows:

A mixture of 2-(benzyloxycarbonylamino)-4-methylsulfanylbutyric acid (1.13 g; 2.76 mmol), 1-(morpholino)propan-2-ol (0.57 ml; 4 mmol), EDC (0.768 g; 4 mmol), DMAP (0.488 g; 4 mmol) in dichloromethane (5 ml) was stirred overnight at ambient temperature. After evaporation of the solvent, the residue was purified by flash chromatography eluting with dichloromethane/ethanol (97/3) to give 1-(morpholinoprop-2-yl 2-(benzyloxycarbonylamino)-4-methylsulfanylbutyrate as a foam. Yield=55%.

$^1$H NMR (CDCl$_3$, 400 MHz) δ1.2(3H, d); 1.9–2.7 (9H, m); 2.13 (3H, s); 3.6 (4H, m): 4.5 (1H, m); 5.05–5.25 (3H, m); 5.44 (1H, m); 7.3–7.4 (5H, m).

The suspension of the above compound (1 g; 2.43 mmol), HCO$_2$NH$_4$ (0.55 g; 8.72 mmol) and 10% palladium-on-carbon (0.6 g) in DMF (5 ml) and water (0.8 ml) was stirred for 2 hours. After filtration on Celite and evaporation to dryness, the residue was purified on flash chromatography eluting with dichloromethane/methanol (97/3) to give 1-(morpholino)prop-2-yl 2-amino-4-methylsulfanylbutyrate. Yield 42%.

$^1$H NMR (CDCl$_3$, 400 MHz) δ1.25 (3H, m); 1.8–2.15 (2H, m); 2.11 (3H, s); 2.3–2.7 (11H, m); 3.5–3.8 (3H, m).

MS (ESI) m/z 277 (MH$^+$)

EXAMPLE 14

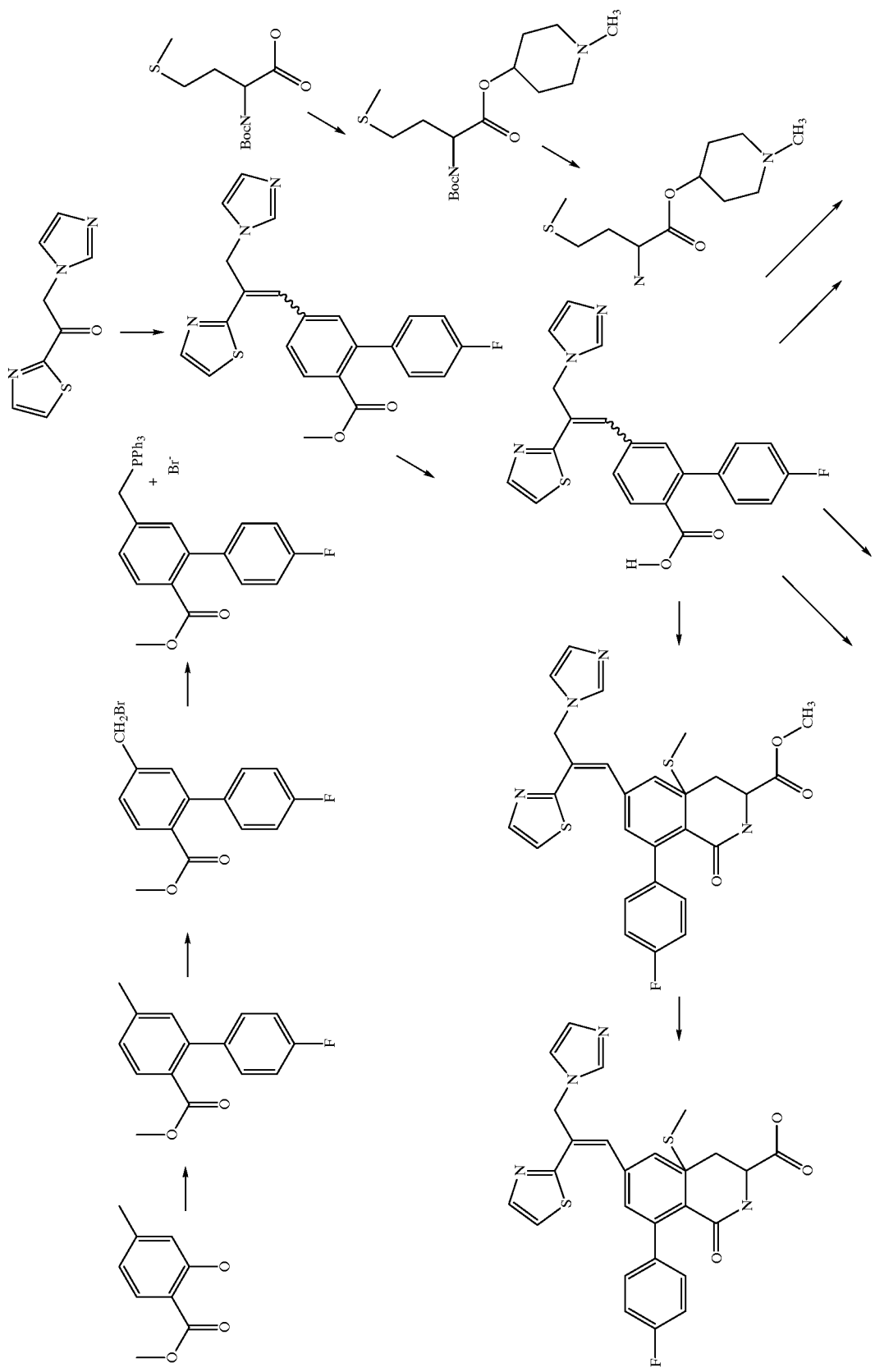

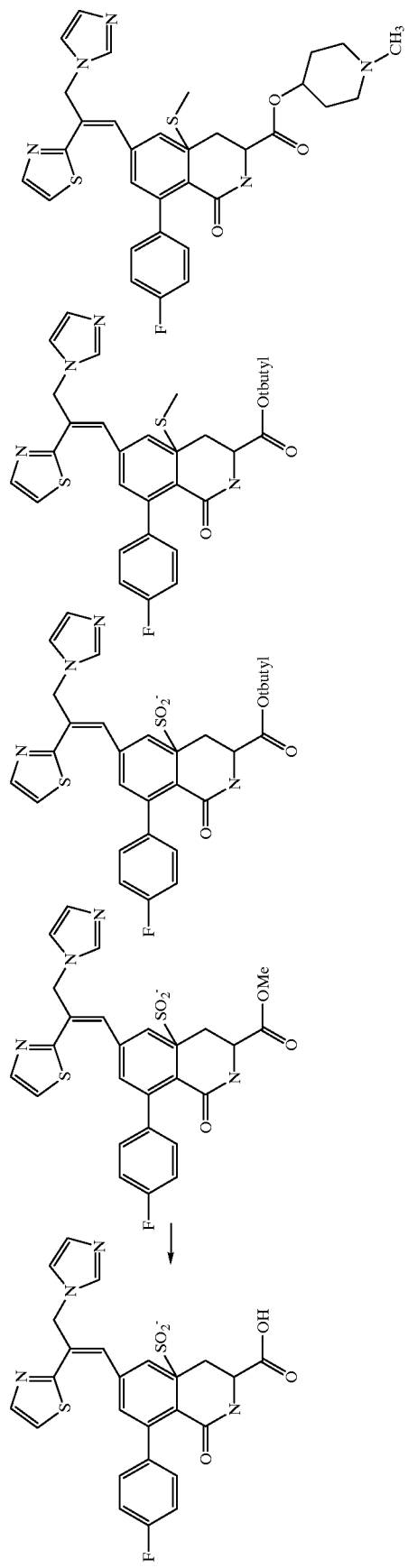

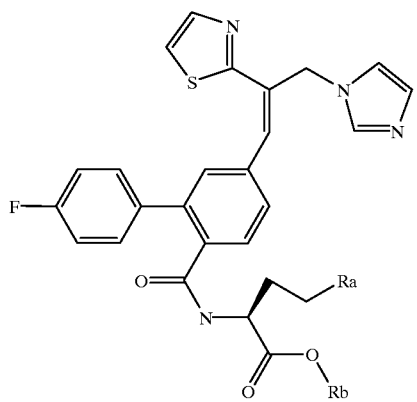

| Compound | R$^a$ | Rb | Yield |
|---|---|---|---|
| a) | SCH$_3$ | H | 34% |
| b) | SCH$_3$ | CH$_3$ | 50% |
| c) | SCH$_3$ | t butyl | 21% |
| d) | SO$_2$CH$_3$ | H | 51% |
| e) | SO$_2$CH$_3$ | CH$_3$ | 55% |
| f) | SO$_2$CH$_3$ | t butyl | 53% |
| g) | SCH$_3$ | N-methylpiperidin-4-yl | 51% |

Preparation of Compound a)

Compound a) was prepared using similar methodology to that described in example 1 for compound a) in step A). Yield 34%

$^1$HNMR (DMSOd$_6$+CF$_3$COOD, 400 MHz) δ1.8–2.3 (4H, m); 2.0 (3H, s); 4.3 (1H, m); 5.48 (2H, s); 7.1–7.9 (12H, m); 9.25 (1H, s).

Anal calcd for C$_{27}$H$_{25}$FN$_4$O$_3$S$_2$, 0.6 H$_2$O C, 59.24; H, 4.82; N, 10.23; S, 11.71.

Found: C, 55.15; H, 4.51; N, 9.68; S, 10.49.

MS (ESI) m/z 537 (MH$^+$)

The starting material was prepared as follows:

Triflic anhydride (170 ml; 1.01 mol) was added to a solution of methyl 2-hydroxy-4-methylbenzoate (153 g; 0.92 mol) in pyridine (1.5 l), at 0° C. The mixture was stirred at ambient temperature overnight. After evaporation of the pyridine, the residue was acidified to pH 3.5 with 6N HCl and extracted with ether. The organic phase was evaporated and the residue purified by flash chromatography eluting with a gradient of 0–5% ethyl acetate/petroleum ether to give methyl 2-trifluoromethylsulfonyloxy-4-methylbenzoate (245 g; 90%).

$^1$H NMR (CDCl$_3$, 400 MHz) δ: 1.55 (3H,s); 2.45 (3H, s); 3.94 (3H, s); 7.09 (1H, s); 7.26 (1H, s); 7.98 (1H, d).

Tetrakis(triphenylphosphine)palladium (9 g; 7.8 mmol) and ethanol (780 ml) was added to a suspension of methyl 4-methyl-2-trifluoromethanesulphonyloxybenzoate (58 g; 0.195 mol), 2M aqueous solution of sodium carbonate (250 ml; 0.5 mol), 4-fluorophenylboronic acid (30 g; 0.214 mol) and lithium chloride (16.5 g; 0.39 mol) in toluene (1.65 ml), under argon atmosphere. The mixture was refluxed for 4 hours, diluted with ethyl acetate (1 l), washed with aqueous sodium hydroxide solution 1N (1 l). The organic phase was evaporated and the residue purified by flash chromatography (ethyl acetate/petroleum ether: 95/5) to give methyl 2-(4-fluorophenyl)-4-methylbenzoate (46.8 g; 99%).

$^1$H NMR (CDCl$_3$, 400 MHz) δ: 2.41 (3H, s); 3.64 (3H, s); 7–7.03 (6H, m); 7.7 (1H, d).

A solution of methyl 2-(4-fluorophenyl)-4-methylbenzoate (54.18 g; 0.22 mol), N-bromosuccinimide (39.6 g; 0.22 mol), 2,2'-azobis(2'-methylproprionitrile) (0.25 g; 1.5 mmol) and benzoylperoxide (0.25 g; 1 mmol) in tetrachloromethane (550 ml) was heated at reflux for 6 hours. The solid was filtered and the filtrate evaporated to give methyl 4-bromomethyl-2-(4-fluorophenyl)benzoate as an oil (79.7 g; 79%) which was used in the next step without purification.

$^1$H NMR (CDCl$_3$, 400 MHz) δ: 3.65 (3H, s); 4.51 (2H, s); 7–7.5 (6H, m); 7.82 (1H, m)

A solution of methyl 4-bromomethyl-2-(4-fluorophenyl) benzoate (12.85 g; 0.04 mol) and triphenyl phosphine (10.53 g; 0.04 mol) in toluene (230 ml) was treated at reflux for 3 hours. The resulting solid was filtered, washed with ether and pentane and dried to give 3-(4-fluorophenyl)-4-methoxycarbonylbenzyltriphenylphosphonium bromide (12.78 g, 78%).

$^1$H NMR (CDCl$_3$, 400 MHz) δ3.62 (3H, s); 5.76 (2H, d); 6.8–7.1 (4H, m); 7.3–7.9 (18 H, m).

Potassium tert-butoxide (1.68 g; 15 mmol) was added to a mixture of thiazol-2-yl imidazol-1-ylmethylketone (1.93 g; 10 mmol), 3-(4-fluorophenyl)-4-methoxycarbonylbenzyltriphenylphosphorium bromide (8.73 g; 15 mmol) and 18-crown-6 (0.1 g; 0.3 mmol) in dichloromethane (70 ml), at −60° C. under an argon atmosphere. After stirring overnight, at room temperature, the resulting mixture was treated by a saturated aqueous solution of ammonium chloride extracted with dichloromethane and purified by flash chromatography, eluting with dichloromethane/ethanol (98/2) to give methyl 2-(4-fluorophenyl)-4-[2-(thiazol-1-yl)-3-(imidazol-1-yl)prop-1-en-1-yl]benzoate as a mixture of E and Z isomers. Yield 73%.

A solution of methyl 2-(4-fluorophenyl)-4-[2-(thiazol-2-yl)-3-(imidazol-1-yl)prop-1-en-1-yl]benzoate (E and Z isomers) (1.99 g; 5 mmol) in methanol (20 ml) was refluxed with 2N aqueous sodium hydroxide solution (5 ml; 10 mmol) for 2 hours. Methanol was then evaporated and the solution acidified to pH 5.5 with 6N HCl. The resulting precipitate was filtered, washed with water and dried to give 2-(4-fluorophenyl)-4-[2-(thiazol-2-yl)-3-(imidazol-1-yl) prop-1-en-1-yl]benzoic acid as a mixture of E and Z isomers. Yield=80%.

Preparation of Compound b)

A mixture of 2-(4-fluorophenyl)-4-[2-(thiazol-2-yl)-3-(imidazol-1-yl)prop-1-en-1-yl]benzoic acid (0.898 g, 2.21 mmol), L-methionine methyl ester hydrochloride (0.443 g, 2.21 mmol), HOBT (0.3 g, 2.21 mmol), EDC (0.425 g, 2.21 mmol) and N-methylmorpholine (0.25 ml, 2.21 mmol) in dichloromethane (15 ml) was stirred overnight at room temperature, washed with saturated sodium hydrogen carbonate (aqueous) and extracted with dichloromethane. The organic phase was evaporated and the residue purified on reverse phase silica eluting a gradient of 40–50% methanol/(NH$_4$)$_2$CO$_3$ buffer (2 g/l pH 7). Appropriate fractions were evaporated and extracted with dichloromethane and evaporated to give methyl (2S)-2-{4-[(Z)-2-(thiazol-2-yl)-3-(imidazol-1-yl)prop-1-enyl)]-2-(4-fluorophenyl) benzamido}-4-methylsulonylbutyrate as a foam (yield 50%). The corresponding hydrochloride salt was prepared by treatment of the compound in solution in dichloromethane (2 ml) with a 3.8 N HCl solution in ether, dilution with ether (100 ml) and filtration of the resulting precipitate.

$^1$H NMR (CDCl$_3$, 400 MHz) δ1.75–2.1 (2H, m); 2.0 (3H, s); 2.15–2.25 (2H, m); 3.68 (3H, s); 4.7 (1H, m); 5.20 (2H, m); 6.02 (1H, d); 6.7 (1H, s); 7–7.3 (9H, m); 7.6 (2H, m); 7.80 (1H, d).

Anal calcd C$_{28}$H$_{27}$FN$_4$O$_3$S$_2$, 0.30 H$_2$O, 1 HCl C, 56.7; H, 4.81; N, 9.54; S, 10.92; Cl, 6.04.

Found: C, 56.54; H, 4.96; N, 9.43; S, 10.75; Cl, 6.08.

MS (ESI) m/z 551 (MH+).

Preparation of Compound c)

Compound c) was prepared using similar methodology to that used to prepare compound b) but using the L-methionine-t-butyl ester. The E and Z isomers were separated on reverse phase silica eluting with a gradient of 40–50% methanol/$(NH_4)CO_3$ buffer (2 g/l pH7) as in the isolation of compound b). Yield 21%.

$^1$H NMR (CDCl$_3$, 400 MHz) δ1.45 (9H, s); 1.7–2.05 (2H, m); 2.04 (3H, s); 2.2–2.3 (2H, m); 4.4–4.5 (1H, m); 5.18 (2H, s); 6–6.1 (1H, m); 6.72 (1H, s); 7–7.7 (11H, m); 7.85 (1H, d)

Anal calcd for $C_{31}H_{33}FN_4O_3S_2$, 0.4 H$_2$O C, 62.06; H, 5.68; N, 9.35; S, 10.69.

Found: C, 61.58; H, 6.47; N, 8.78; S, 9.79.

MS (ESI) m/z 593 (MH+).

Preparation of Compound d)

Compound d) was prepared using similar methodology to that described in example 1, compound a), step 1. The E and Z isomers were separated on reverse phase silica eluting with a gradient of 40–50% methanol/$(NH_4)CO_3$ buffer (2 g/l pH7) as in the isolation of compound b). Yield 51%.

$^1$H NMR (DMSOd$_6$+CF$_3$COOD, 400 MHz) δ1.9–2.2 (2H, m); 2.8–3.2 (2H, m); 2.96 (3H, s); 4.34 (1H, m); 5.48 (2H, s); 7.1–7.9 (12H, m); 8.79 (1H, d); 9.26 (1H, s).

Anal calcd for $C_{27}H_{25}FN_4O_5S_2$, 2 H$_2$O C, 53.63; H, 4.83; N, 9.27; S, 10.61.

Found: C, 50.97; H, 4.66; N, 9.41; S, 10.12.

MS (ESI) m/z 569 (MH+).

Preparation of Compound e)

Compound e) was prepared using similar methodology to that described for compound b) but using the L-methionine sulfone methyl ester (NH$_2$CH(CH$_2$CH$_2$SO$_2$Me)COOMe). The E and Z isomers were separated on reverse phase silica eluting with a gradient of 40–50% methanol/$(NH_4)CO_3$ buffer (2 g/l pH7) as in the isolation of compound b). Yield 55%.

$^1$H NMR (DMSOd$_6$+CF$_3$COOD, 400 MHz) δ1.8–2.3 (2H, m); 2.8–3.2 (2H, m); 2.96 (3H, s); 3.67 (3H, s); 4.35 (1H, m); 5.49 (2H, s); 7.1–7.95 (12 H, m); 9.26 (1H, s).

Anal calcd for $C_{28}H_{27}FN_4O_5S_2$, 0.8 H$_2$O, 1 HCl C, 53.08; H, 4.71; N, 8.84; S, 10.12; Cl, 5.57.

Found: C, 53.38; H, 4.94; N, 8.58; S, 10.15; Cl, 5.57.

MS (ESI) m/z 583 (MH+).

Preparation of Compound f)

Compound f) was prepared using similar methodology to that described for compound b) but using L-methionine sulfone t-butyl ester (NH$_2$CH(CH$_2$CH$_2$SO$_2$Me)COOC(Me)$_3$) instead of L-methionine methyl ester hydrochloride to give tert-butyl (2S)-2-{4-[(Z)-2-(thiazol-2-yl)-3-(imidazol-1-yl)prop-1-enyl)]-2-(4-fluorophenyl)benzamido}-4-methylsulfonylbutyrate. The E and Z isomers were separated on reverse phase silica eluting with a gradient of 40–50% methanol/$(NH_4)CO_3$ buffer (2 g/l pH7) as in the isolation of compound b). Yield 53%.

$^1$H NMR (CDCl3, 400 MHz) δ1.25 (9H, s); 1.8–2.1 (2H, m); 2.25–2.4 (2H, m); 2.88 (3H, s); 4.5 (1H, m); 5.21 (2H, s); 6.1 (1H, d); 6.7 (1H, s); 7–7.3 (9H, m); 7.58 (2H, m); 7.81 (1H, m).

Anal calcd for $C_{31}H_{33}FN_4O_5S_2$, 0.5 H$_2$O C, 58.75; H, 5.41; N, 8.84; S, 10.12.

Found: C, 59.05; H, 5.61; N, 8.45; S, 9.53.

MS (ESI) m/z 625 (MH+).

Preparation of Compound g)

Compound g) was prepared using similar methodology to that described for compound b) but using the L-methionine (N-methylpiperidin-4-yl)ester. The E and Z isomers were separated on reverse phase silica eluting with a gradient of 40–50% methanol/$(NH_4)CO_3$ buffer (2 g/l pH7) as in the isolation of compound b). Yield 51%.

$^1$H NMR (CDCl$_3$, 400 MHz) δ1.6–2.1 (4H, m); 2.02 (3H, s); 2.1–2.35 (8H, m); 2.27 (3H, s); 2.6 (2H, m); 4.62 (1H, m); 4.78 (1H, m); 5.21 (2H, s); 6.05 (1H, d); 6.7 (1H, s); 7–7.3 (9H, m); 7.6 (2H, m); 7.8 (1H, m).

Anal calcd for $C_{33}H_{36}FN_5O_3S_2$, 0.5 H$_2$O, 2.05 HCl C, 55.24; H, 5.49; N, 9.76; S, 8.94; Cl, 10.13.

Found: C, 55.34; H, 5.66; N, 9.72; S, 8.67; Cl, 10.38.

MS (ESI) m/z 634 (MH+).

Synthesis of L-methionine 4-(N-methylpiperidin-4-yl)ester

A solution of tert-butoxycarbonyl-L-methionine (5 g; 20 mmol), 4-hydroxy-1-methylpiperidine (3.3 g; 20 mmol); DMAP (2.44 g; 20 mmol) and EDC (4.6 g; 2.4 mmol) in dichloromethane (200 ml) was stirred at ambient temperature overnight. The mixture was extracted with dichloromethane. The organic phase was evaporated and purified by flash chromatography, eluting with dichloromethane/ethanol (97/3) to give 1-methylpiperidin-4-yl 2-tert-butoxycarbonylamino-4-methylsulfanylbutyrate. Yield 56%.

$^1$H NMR (CDCl$_3$, 400 MHz) δ1.45 (9H, s); 1.6–2.2 (6H, m); 2.10 (3H, s); 2.2–2.4 (2H, m); 2.25 (3H, s); 2.4–2.75 (4H, m); 4.38 (1H, m); 4.85 (1H, m); 5.12 (1H, m).

A solution of the 1-methylpiperidin-4-yl 2-tert-butoxycarbonylamino-4-methylsulfanylbutyrate (3.8 g; 11 mmol) in dichloromethane (5 ml) and TFA (10 ml) was stirred at ambient temperature for 2 hours. After evaporation to dryness, the residue was redissolved in dichloromethane and treated with a solution of 3.8 M HCl in ether (6 ml) at 0° C. The resulting precipitate was triturated with ether and filtrated to give L-methionine 4-(N-methylpiperidin-4-yl) ester.

$^1$H NMR (DMSOd$_6$+CF$_3$COOD, 400 MHz) δ1.8–2.2 (6H, m); 2.05 (3H, s); 2.45–2.9 (2H, m); 2.75 (3H, s); 3.25–3.5 (4H, m); 4.15 (1H, m); 4.9–5.1 (1H, m).

A solution of the 1-methylpiperidin-4-yl 2-tert-butoxycarbonylamino-4-methylsulfanylbutyrate (3.8 g; 11 mmol) in dichloromethane (5 ml) and TFA (10 ml) was stirred at ambient temperature for 2 hours. After evaporation to dryness, the residue was redissolved in dichloromethane and treated with a solution of 3.8 M HCl in ether (6 ml) at 0° C. The resulting precipitate was triturated with ether and filtrated to give L-methionine 4-(N-methylpiperidin-4-yl) ester.

$^1$H NMR (DMSOd$_6$+CF$_3$COOD, 400 MHz) δ1.8–2.2 (6H, m); 2.05 (3H, s); 2.45–2.9 (2H, m); 2.75 (3H, s); 3.25–3.5 (4H, m); 4.15 (1H, m); 4.9–5.1 (1H, m).

EXAMPLE 15

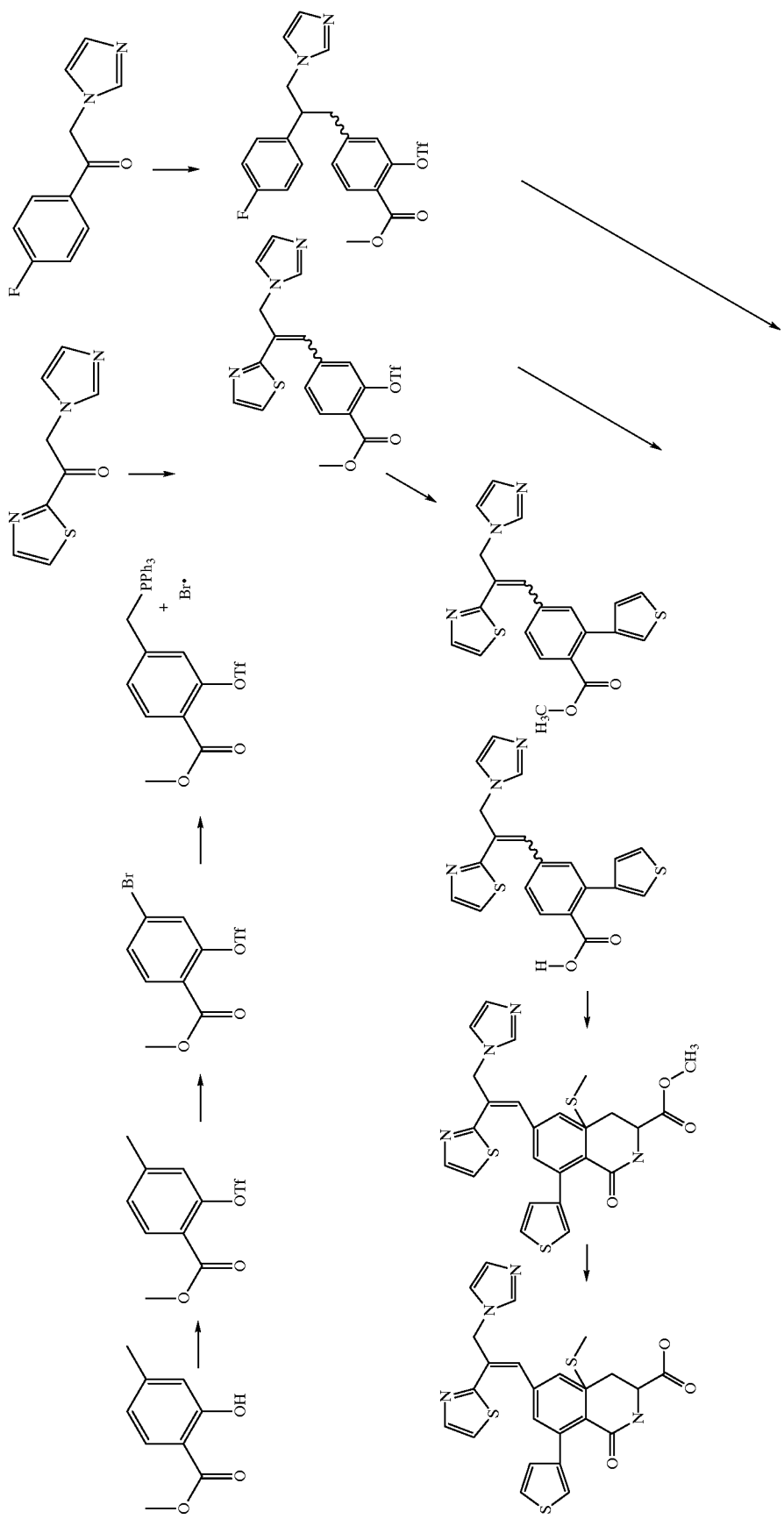

-continued
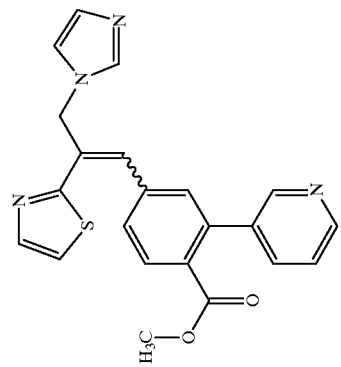
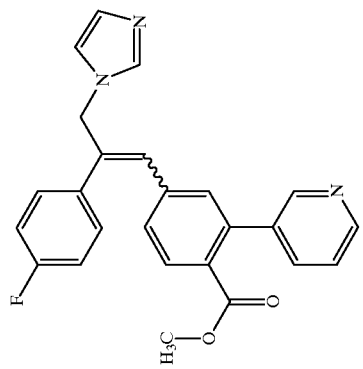
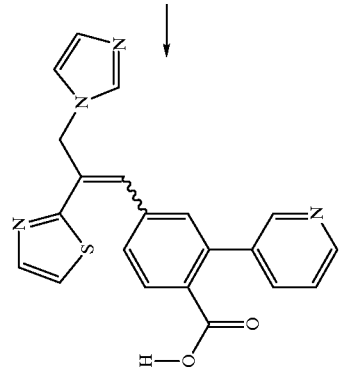
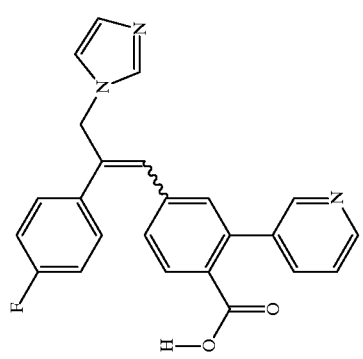
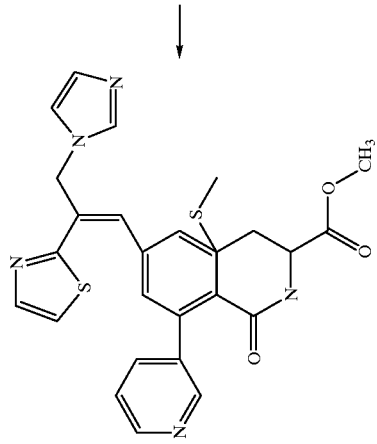
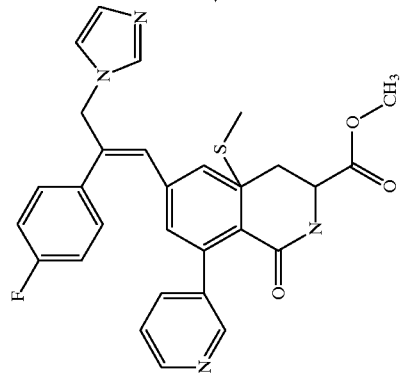

Preparation of (2S)-2-{4-[(Z)-2-(thiazol-2-yl)-3-(imidazol-4-yl)prop-1-en-1-yl]-2-(thien-3-yl)benzamido}-4-methylsulfanylbutyric acid The title compound was prepared using similar methodology to that described in example 1, compound a), step A). Yield 27%

¹H NMR (DMSOd₆+CF₃COOD, 400 MHz) δ1.9–2.1 (2H, m); 2.03 (3H, s); 2.3–2.6 (2H, m); 4.40 (1H, m); 5.45-2H, s); 7.1–7.9 (11H, m); 9.25 (1H, s).

Anal calcd for $C_{25}H_{24}N_4O_3S_3$, 1.5 $H_2O$ C, 54.43; H, 4.93; S, 17.44.

Found: C, 54.25; H, 4.72; S, 17.23.

MS (ESI) m/z 525 (MH⁺).

The starting material was prepared as follows:

Triflic anhydride (88 ml; 0.519 mol) was added at 0° C. to a solution of methyl 2-hydroxy-4-methylbenzoate (78.4 g; 0.47 mol) in pyridine (800 ml). The mixture was stirred at ambient temperature overnight. After evaporation of the pyridine, the residue was acidified to pH 3.5 with 6N HCl and extracted with ether. The organic phase was evaporated and the residue purified by flash chromatography eluting with a gradient of 0–5% ethyl acetate/petroleum ether to give. Yield=79%.

¹H NMR (CDCl₃, 400 MHz) δ2.45 (3H, s); 3.94 (3H, s); 7.1 (1H, s); 7.27 (1H, s); 7.98 (1H, d).

A solution of methyl 4-methyl-2-trifluoromethylsulfonyloxybenzoate (23.79 g; 7.9 mmol), N-bromosuccinimide (14.19 g; 7.9 mmol), 2,2-azobis (2'-methylproprionitrile) (0.5 g; 3 mmol) and benzoylperoxide (0.5 g; 2 mmol) in tetrachloromethane (250 ml) was heated at reflux for 6 hours. The solid was filtered and the filtrate evaporated to dryness to give methyl 4-bromomethyl-2-trifluoromethylsulfonyloxybenzoate. Yield=55%.

¹H NMR (CDCl₃, 400 MHz) δ3.98 (3H, s); 4.45 (2H, s); 7.2–8.1 (3H, m).

A solution of methyl 4-bromomethyl-2-trifluoromethylsulfonyloxybenzoate (23.12 g; 61 mmol) and triphenylphosphine (16 g; 61 mmol) in toluene (240 ml) was refluxed for 5 hours. The resulting solid was filtered and washed with ether to give 3-trifluoromethylsulfonyloxy-4-methoxycarbonylbenzyl triphenylphosphonium bromide. Yield=100%.

¹HNMR (CDCl₃, 400 MHz) δ3.91 (3H, s); 6 (2H, d); 7–7.9 (18H, m).

Methyl 2-(trifluoromethylsulfonyloxy)-4-[2-(thiazol-2-yl)-3-(imidazol-1-yl)prop-1-en-1-yl]benzoate was prepared using similar methodology to the synthesis of methyl 2-(4-fluorophenyl)-4-[2-(thiazol-2-yl)-3-(imidazol 1-yl)prop-1-en-1-yl]benzoate described in example 14 (yield 86%)

¹H NMR (CDCl₃, 400 MHz) δ3.95 (3H, s); 5.2 (2H, s); 6.55 (1H, s); 6.9–8.05 (8H, m).

To a suspension of product methyl 2-(trifluoromethylsulfonyloxy)-4-[2-(thiazol-2-yl)-3-(imidazol-1-yl)prop-1-en-1-yl]benzoate (1.42 g; 3 mmol), 2M aqueous sodium carbonate solution (4.2 ml), thiophene-3-boronic acid (0.42 g; 3.3 mmol) and lithium chloride (0.254 g; 6 mmol) in toluene (140 ml) was added, under argon atmosphere, tetrakis(triphenylphosphine)palladium (0.14 g; 0.12 mmol). The mixture was refluxed overnight, washed with 2N, aqueous sodium hydroxide solution and saturated aqueous sodium chloride solution. The organic phase was evaporated and the residue purified by flash chromatography dichloromethane/ethanol (98/2) to give methyl 2-(thien-3-yl)-4-[2-(thiazol-2-yl)-3-(imidazol-1-yl)prop-1-en-1-yl]benzoate as a mixture of E and Z isomers. Yield: 51%.

A solution of methyl 2-(thien-3-yl)-4-[2-(thiazol-2-yl)-3-(imidazol-1-yl)prop-1-en-1-yl]benzoate (0.62 g; 1.52 mmol) and aqueous sodium hydroxide solution 2N (1.53 ml; 3.04 mmol) in methanol was refluxed for 4 hours. After evaporation of the methanol, the residue was acidified to pH 5.5 with 2N HCl, extracted with dichloromethane to give after evaporation of the organic phase compound 2-(thienyl-3-yl)-4-[2-(thiazol-2-yl)-3-(imidazol-1-yl)prop-1-en-1-yl] benzoic acid as a mixture of E and Z isomers. Yield: 74%.

Preparation of methyl (2S)-2-{4-[(Z)-2-(thiazol-2-yl)-3-(imidazol-1-yl)prop-1-en-1-yl]-2-(thien-3-yl)benzamido}-4-methylsulfanylbutyrate The title compound was prepared using similar methodology to that described in example 14 (yield 33%).

¹H NMR (CDCl₃, 400 MHz) δ1.8–2.3 (4H, m); 2.04 (3H, s); 3.71 (3H, s); 4.71 (1H, m); 5.20 (2H, s); 6.1 (1H, d); 6.69 (1H, s); 7–7.9 (11H, m)

Anal calcd for $C_{26}H_{26}N_4O_3S_3$, HCl C, 54.29; H, 4.73; N, 9.74; S, 16.72.

Found: C, 54.24; H, 4.81; N, 9.82; S, 16.71.

MS (ESI) m/z 539 (MH⁺)

Preparation of methyl (S)-2-{4-{(Z)-2-(thiazol-2-yl)-3-(imidazol-1-yl)prop-1-en-1-yl]-2-(pyridin-3-yl)benzamido}-4-methylsulfanylbutyrate The title compound was prepared using similar methodology to that described for the previous compound but replacing thiophene-3-boronic acid with diethyl 3-pyridylborane. Yield: 40%.

¹H NMR (CDCl₃, 400 MHz) δ1.8–2.15 (2H, m); 2 (3H, s); 2.26–2.28 (2H, m); 3.71 (3H, s);4.65–4.68(1H,m); 5.22 (2H, s); 6.20–6.25 (1H, d); 6.69 (1H, s); 7–7.4 (6H, m); 7.55–7.7 (3H, m); 7.82–7.83 (1H, d); 8.52–8.53 (1H, d); 8.55–8.65 (1H, m)

Anal calcd for $C_{27}H_{27}N_5O_3S_2$, 0.3 $H_2O$ C, 60.16; H, 5.16; N, 12.99; S, 11.90.

Found: C, 59.74; H, 5.25; N, 12.95; S, 11.91.

MS (ESI) m/z 534 (MH⁺)

Preparation of methyl (2S)-2-{4-[(E)-2-(4-fluorophenyl)-3-(imidazol-1-yl)prop-1-en-1-yl]-2-(pyrid-3-yl)benzamido}-4-methylsulfanylbutyrate The title compound was prepared using similar methodology to that described for the previous compound but substituting thiazol-2-ylimidazol-1-ylmethyl ketone with 4-fluorophenyl (imidazol-1-ylmethyl)ketone. Yield=18%

¹H NMR (DMSO, 400 MHz) δ1.79–1.88 (2H, m); 1.98 (3H, s); 2.21–2.32 (2H, m); 3.32 (3H, s); 4.3–4.35 (1H, m); 5.06 (2H, s); 6.7 (1H, s); 6.85 (1H, s); 6.95 (1H, s); 7.05 (1H, d); 7.11 (1H, s); 7.17–7.19 (4H, m); 7.30–7.34 (2H, m); 7.50–7.53 (2H, m); 8.26–8.27 (d, 1H); 8.44–8.47 (1H, m); 8.72–8.74 (1H, d).

Anal calcd for $C_{30}H_{29}FN_4O_3S$, 0.6 $H_2O$, 1.6 HCl C, 58.71; H, 5.22; N, 9.13; S, 5.22; Cl, 9.24.

Found: C, 58.83; H, 5.28; N, 8.99; S, 4.99; Cl, 9.17.

MS (ESI) m/z 544 (MH⁺)

EXAMPLE 16

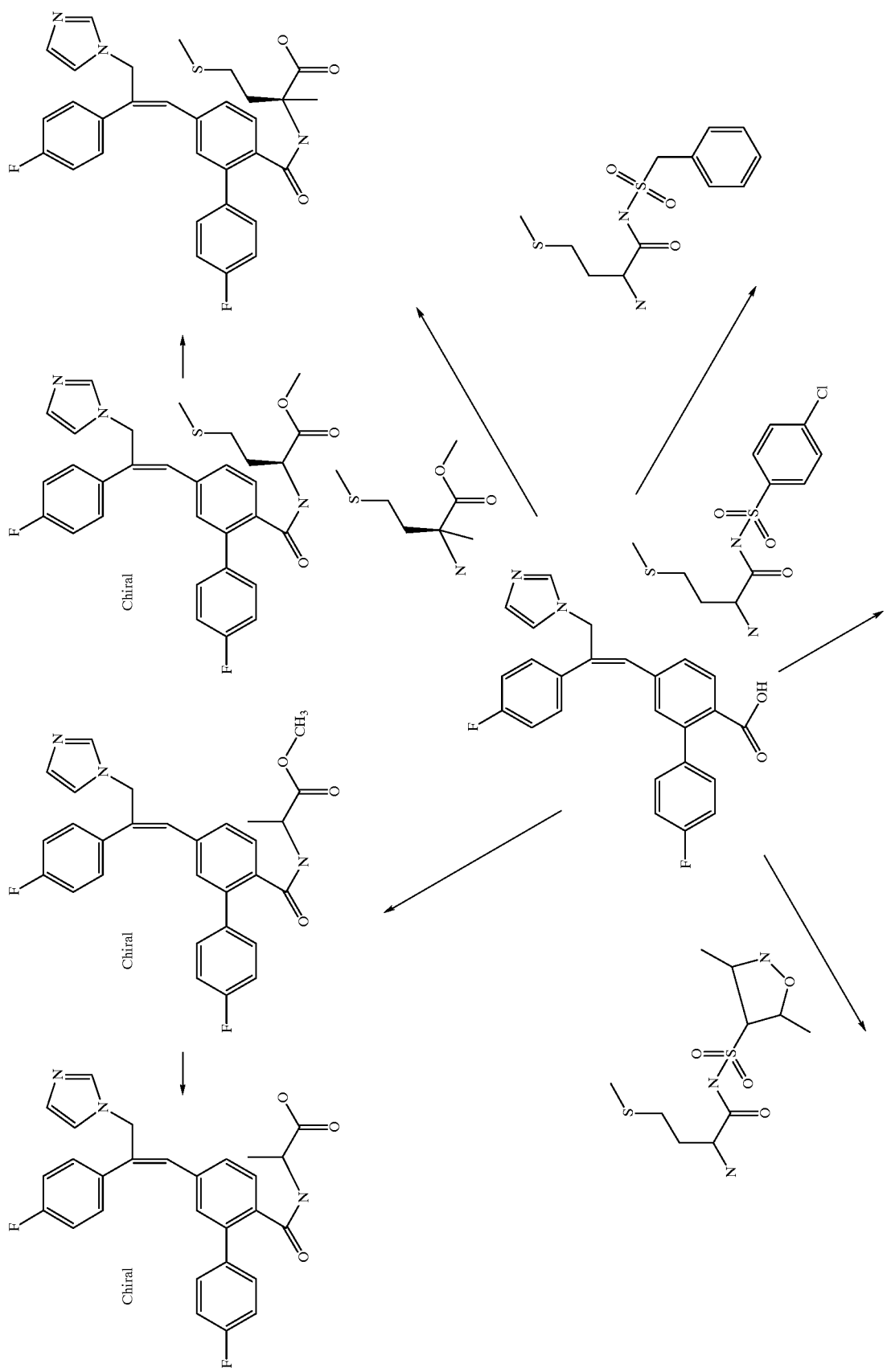

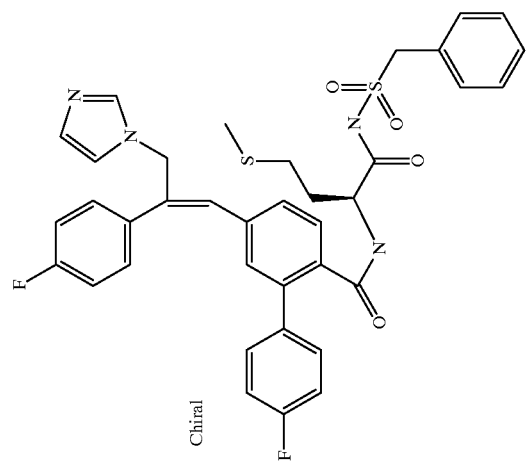
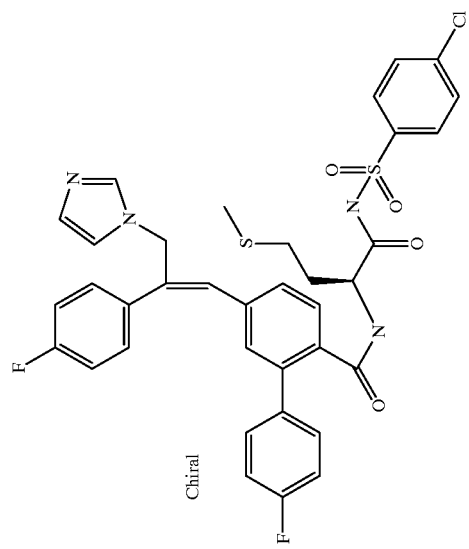
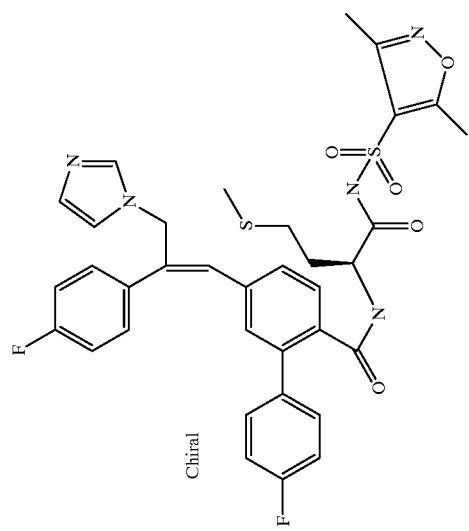

Preparation of N-(3,5-dimethylisoxazol-4-ylsulfonyl)(2S)-2-{4-[(E)-2-(4-fluorophenyl)-3-(imidazol-1-yl)prop-1-en-1-yl]-2-(4-fluorophenyl)benzamido}-4-methylsulfanylbutyramide The title compound was prepared in a similar mamer to that described in Example 1 compound a); step E but substituting N-(3,5-dimethylisoxazol-4-ylsulfonyl)(2S)-2-amino-4-methylsulfanylbutyramide in place of the L-methionine methyl ester. Yield=35%.

$^1$H NMR (DMSOd$_6$+CF$_3$COOD, 400 MHz) δ1.71–1.9 (2H, m); 1.98 (3H, s); 2.15–2.20 (2H, m); 2.34 (3H, s); 2.64 (3H. s); 4.2–4.3 (1H, m); 5.34 (2H, s); 6.93–7.3 (12H, m); 7.65 (1H, s); 7.73 (1H, s); 8.6 (1H, d); 9.08 (1H, s).

Anal calcd for $C_{35}H_{33}F_2H_5O_5S_2$, $H_2O$ C, 58.08; H, 4.87; N, 9.68; S, 8.86.

Found: C, 57.82; H, 4.75; N, 9.80; S, 8.31.

MS (ESI) m/z 706 (MH$^+$)

3,5-Dimethylisoxazol-4-ylsulfanyl (2S)-2-amino-4-methylsulfanylbutyramide was prepared as follows:

A) 3,5-Dimethylisoxazol-4-ylsulfonyl (2S)-2-tert-butoxycarbonylamino-4-methylsulfanylbutyramide was prepared in a similar manner to that described for Example 20, compound f) step B) but substituting 3,5-dimethylisoxazol-4-ylsulfonamide for trifluoromethane sulfonamide.

Yield=100%

$^1$H NMR (DMSO-D6, 300 MHz) d 1.3 (9H, s); 1.70 (2H, m); 2.0(3H, s); 2.35 (5H, m); 2.60 (3H, s); 3.95 (1H, m); 7.15 (1H, d)

MS (ES$^-$) m/z 406 (M–H)$^-$

B) The starting material prepared in step A) (20.3 g, 0.05 mole) was stirred in 2.7M HCl/EtOAc (80 ml) for 18 hours, twice. White solid which came out of solution as collected by filtration and washed with diethylether (11.3 g, 65%)

$^1$H NMR (DMSO-D6, 300 MHz) d 2.0 (5H, m); 2.35 (3H, s); 2.40 (2H, m); 2.65 (3H, s); 3.9 (1H, m); 8.4 (3H, bs)

MS (ES$^-$) m/z 306 (M–H)$^-$

Preparation of N-(4-chlorophenylsulfonyl)(2S)-2-{4-[(E)-2-(4-fluorophenyl-3-(imidazol-1-yl)prop-1-en-1-yl]-2-(4-fluorophenyl)benzamido}-4-methylsulfanylbutyramide The title compound was prepared in a similar manner to that described in Example 1 compound a); step E but substituting N-(4-chlorophenylsulfonyl)(2S)-2-amino-4-methylsulfanylbutyramide in place of L-Methionine methyl-ester. Yield=58%

$^1$H NMR (CDCl$_3$+CD$_3$COOD, 400 MHz) δ1.6–2 (2H, m); 1.94 (3H, s); 2.7–2.85 (2H, m); 4.5–4.6 (1H, m); 5 (2H, s); 6.61 (1H, s); 6.8–8.2 (18H, m).

Anal calcd for $C_{36}H_{31}ClF_2N_4O_4S_2$ C, 59.95; H, 4.33; N, 7.77; S, 8.89.

Found: C, 60.13; H, 5.06; N, 8.05; S, 7.84.

MS (ESI) m/z 723 (MH$^+$)

The starting material was prepared as follows:

N-(4-chlorophenylsulfonyl) (2S)-2-tert-butoxycarbonylamnino-4-methylsulfanylbutyramide was prepared using a similar method to that used to prepare N-(benzylsulfonyl)(2S)-2-tertbutoxycarbonylamino-4-methylsulfanylbutyramide $^1$H NMR (DMSOd$_6$) δ: 1.38 (s, 9H); 1.71–1.85 (m, 2H); 2.06 (s, 3H); 2.39 (t, 2H); 3.97–4.10 (m, 1H); 7.15 (d, 1H); 7.72–7.78 (m, 2H); 7.93–8.01 (m, 2H); 12.38 (bs, 1H)

N-(4-chlorophenylsulfonyl) (2S)-2-amino-4-methylsulfanylbutyramide was prepared as the hydrochloride salt using a similar method to that described to prepare used to prepare N-(benzylsulfonyl) (2S)-2-amino-4-methylsulfanylbutyramide $^1$H NMR (DMSOd$_6$) δ: 1.95–2.07 (m, 2H), 2.02 (s, 3H), 2.25–2.50 (m, 2H), 3.88–4.00 (m, 1H), 7.70–7.76 (m, 2H), 7.95–8.00 (m, 2H), 8.39 (bs, 3H).

Preparation of (2)-2-{4-[(E)-2-(4-fluorophenyl)-3-(imidazol-1-yl)prop-1-en-1-yl]-2-(4-fluorophenyl)benzamido}-2-methyl-4-methylsulfanylbutyric acid The title compound was prepared using a similar methodology to that described in Example 1 compound a), step A. Yield=58%.

$^1$H NMR (DMSOd$_6$+CF$_3$COOD, 400 MHz) δ1.3 (3H, s); 1.9–2.4 (4H, m); 1.99 (3H, s); 5.34 (2H,s); 6.9–7.3 (12H, m); 7.65 (1H, s); 7.74 (1H, s); 8.32 (1H, s); 9.08 (1H, s).

Anal calcd for $C_{31}H_{29}F_2N_2O_3S$, 2.35 $H_2O$ C, 61.65; H, 5.62; N, 6.96; S, 5.31.

Found: C, 61.29; H, 5.46; N, 7.46; S, 4.98.

MS (ESI) m/z 562 (MH$^+$).

Preparation of methyl (2)-2-{4-[(E)-2-[4-fluorophenyl)-3-(imidazol-1-yl)prop-1-en-1-yl]-2-(4-fluorophenyl)benzamido]-2-methyl-4-methylsulfanylbutyrate The title compound was prepared using a similar method to that described in Example 1, compound a), step E but using α-methyl-L-methionine methyl ester.

Yield=48%

$^1$H NMR (DMSOd$_6$, 400 MHz) δ1.28 (3H, s); 1.9–2.1 (5H, m); 2.2–2.4 (2H, m); 3.55 (3H, s); 5.34 (2H, s); 6.9–7.3 (12 H, m); 7.64 (1H, s); 7.73 (1H, s); 8.51 (1H, s); 9.08 (1H, s).

Anal calcd for $C_{32}H_{31}F_2N_3O_3S$, 0.5 $H_2O$, 1.2 HCl C, 61.16; H, 5.32; N, 6.69; S, 5.10; Cl, 6.77.

Found: C, 61.59; H, 5.55; N, 6.55; S, 4.65; Cl, 6.81.

MS (ESI) m/z 576 (MH$^+$)

Preparation of N-(benzylsulfonyl)(2S)-2-{4-[(E)-2-(4-fluorophenyl)-3-(imidazol-1-yl)prop-1-en-1-yl]-2-(4-fluorophenyl)benzamido}-4-methylsulfanylbutyramide The title compound was prepared in a similar manner to that described in Example 1 compound A, step E but using N-(benzylsulfonyl) (2S)-2-amino4-methylsulfanylbutyramide. Yield=37%.

$^1$H NMR (CDCl$_3$+CD$_3$COOD, 400 MHz) δ1.6–2.2 (4H, m); 1.98 (3H, s); 4.5–4.65 (3H, m); 5 (2H, s); 6.63 (1H, s); 6.9–7.4 (18H, m); 8.2 (1H, s).

Anal calcd for C$_{37}$H$_{34}$F$_2$N$_4$O$_4$S$_2$, 0.2 AcOEt C, 63.19; H, 4.99; N, 7.80; S, 8.93.

Found: C, 63.19; H, 5.08; N, 7.45; S, 8.58.

MS (ESI) m/z 721 (MH$^+$)

N-(Benzylsulfonyl) (2S)-2-amino-4-methylsulfanylbutyramide was prepared as follows:

4-Dimethylaminopyridine (4.76 g) and then 1-(3-dimethylaminopropyl)-3-ethylcarbodiimide HCl (5.60 g) were added to a stirred suspension of L-BOC-methionine (4.85 g) and a-toluenesulfonamide (4.00 g) in DMF (30 ml). The reaction mixture was stirred at ambient temperature for 16 h. The DMF was removed under reduced pressure and the residue taken up into ethyl acetate (50 ml). The solution was washed with 1M citric acid (2×50 ml) and brine (50 ml). The aqueous washings were re-extracted with ethyl acetate (2×40 ml). The combined ethyl acetate extracts were dried and the solvent removed under reduced pressure to give N-(benzylsulfonyl) (2S)-2-amino-4-methylsulfanylbutyramide as a light yellow foam, (9.2 g).

$^1$H NMR (CDCl$_3$) δ: 1.42 (s, 9H); 1.84–1.97 (m, 1H); 2.04 (s, 3H); 2.04–2.19 (m, 1H); 2.56 (t, 2H); 4.18–4.32 (m, 1H); 4.66 (s, 2H); 5.10 (d, 1H); 7.34–7.45 (m, 5H).

A 4.4M solution of HCl in ethyl acetate (20 ml) was added to a stirred solution of N-(benzylsulfonyl) (2S)-2-amino-4-methylsulfanylbutyramide (9.2 g) in ethyl acetate (10 ml) at ambient temperature. After 2 hours, ether (30 ml) was added and the solid isolated by filtration, washing with ether (2×30 ml), to yield N-(benzylsulfonyl)(2S)-2-amino-4-methylsulfanylbutyramide HCl (6.2 g) as a white solid.

$^1$H NMR (DMSOd$_6$) δ: 2.05–2.15 (m, 2H); 2.15 (s,3H); 2.56–2.67 (m, 2H); 3.94–4.05 (m, 1H); 4.86 (s, 2H); 7.47–7.55 (m, 5H); 8.73 (bs, 3H).

Preparation of (2S)-2-{4-{(E)-2-(4-fluorophenyl)-3-(imidazol-1-yl)prop-1-en-1-yl]-2-(4-fluorophenyl)benzamido}propanoic acid The title compound was prepared using similar methodology to that described in Example 1 compound a, step A. Yield=48%.

$^1$H NMR (DMSO+CF$_3$COOD, 400 MHz) δ1.20 (3H, d); 4.20 (1H, m); 5.35 (2H, s); 6.9–7.3 (15H, m); 7.7 (2H, d); 9.08 (1H, s).

Anal calcd for C$_{28}$H$_{23}$F$_2$N$_3$O$_3$, 1.05 H$_2$O C, 66.4; H, 5.0; N, 8.30.

Found: C, 66.11; H, 4.80; N, 8.17.

MS (ESI) m/z 488 (MH$^+$)

Preparation of methyl (2S)-2-{4-[(E)-2-(4-fluorophenyl)-3-(imidazol-1-yl)prop-1-en-1-yl]-2-(4-fluorophenyl)benzamido}propanoate The title compound was prepared using similar methodology to that described in Example 1 compound A, step E but substituting alanine methyl ester. Yield=46%.

$^1$H NMR (DMSOd$_6$+CF$_3$COOD, 400 MHz) δ1.20 (3H, d); 3.60 (3H, s); 4.26 (1H, m); 5.35 (2H, s); 6.9–7.3 (12H, m); 7.65 (2H, d); 9.09 (1H, s).

Anal calcd for C$_{29}$H$_{25}$F$_2$N$_3$O$_3$, 1.6 H$_2$O, 1 HCl C, 61.26; H, 5.21; N, 7.32; Cl, 6.23.

Found: C, 61.10; H, 4.99; N, 7.32; Cl, 6.43.

MS (ESI) m/z 502 (MH$^+$).

EXAMPLE 17

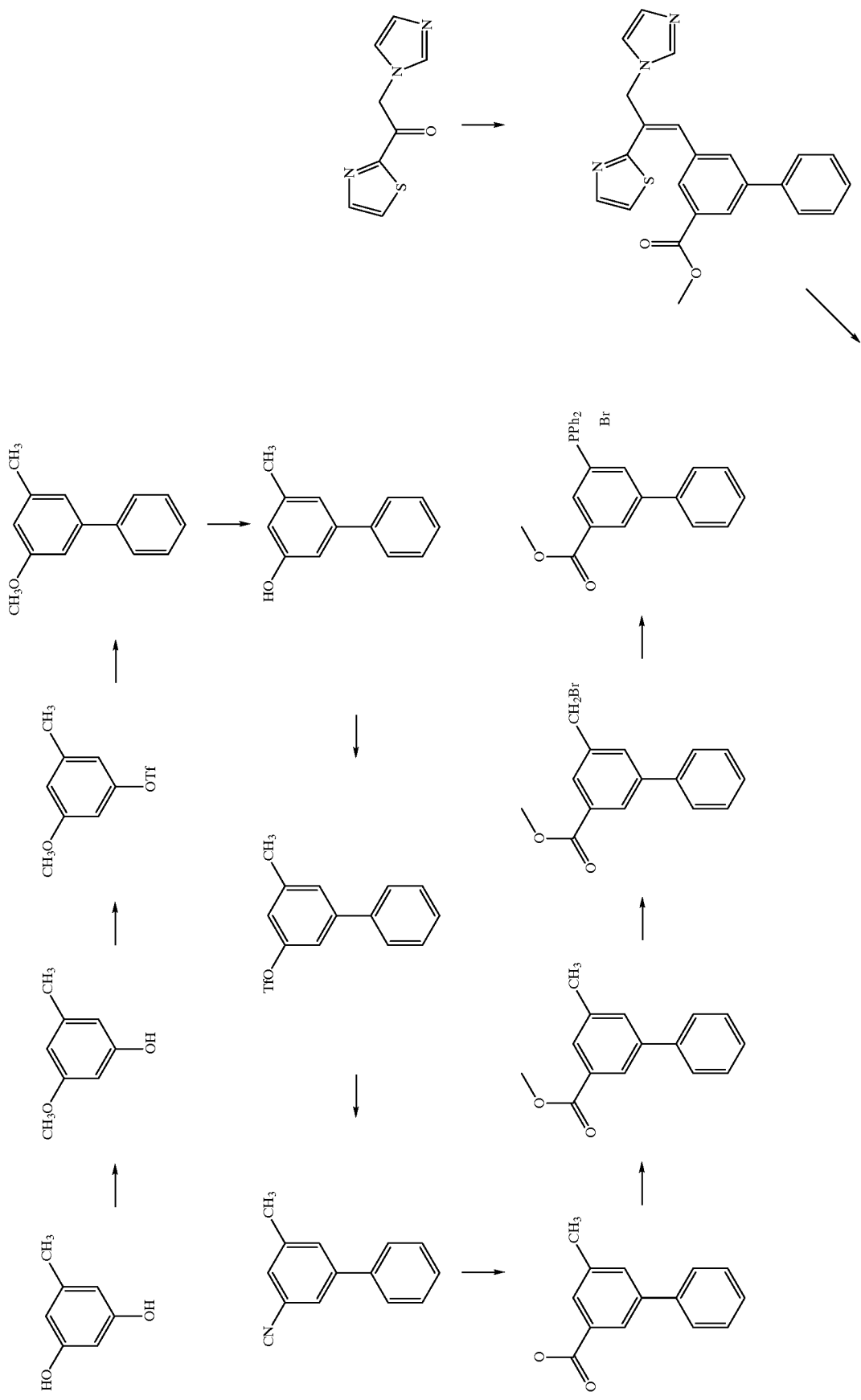

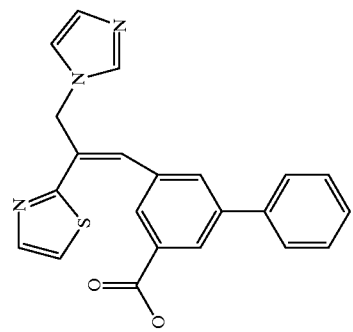
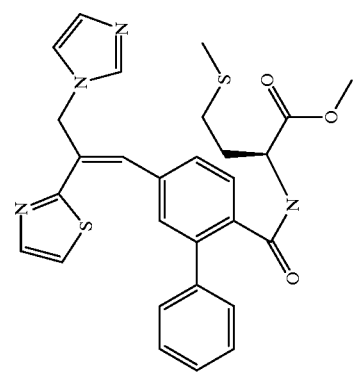
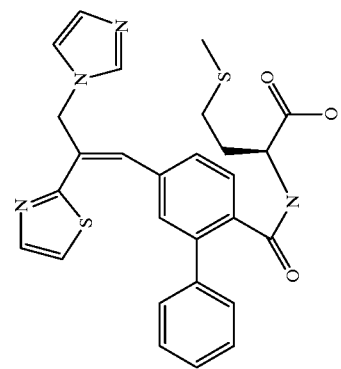

Preparation of (2S)-2-{5-[(Z)-2-(thiazol-2-yl)-3-(imidazol-yl)prop-1-en-1-yl]-3-henylbenzamido}-4-methylsulfanylbutyric acid The title compound was prepared using similar methodology to that described in example 1, compound a), step A. Yield=66%.

$^1$H NMR (CDCl$_3$, 400 MHz) δ2.10 (3H,s), 2.09–2.31 (2H, m); 2.55–2.6 (2H, m); 3.80 (3H, s); 4.90–4.95 (1H, m); 5.25 (2H, s); 6.76 (1H, s); 6.88–6.90 (1H, d); 7.05–7.09 (2H, m); 7.25–7.56 (8H, m); 7.62 (1H, s); 7.82–7.83 (1H, d); 8.00 (1H, s).

Anal calcd for C$_{27}$H$_{26}$N$_4$O$_3$S$_2$ C, 60.53; H, 5.25; N, 10.45; S, 11.97.

Found: C, 60.56; H, 5.25; N, 11.17; S, 11.73.

The starting material was prerpared as follows:

Dimethyl sulfate (39 ml; 0.41 mol) was added to a solution of orcinol (64 g; 0.45 mol) in 10% aqueous sodium hydroxide solution (360 ml). The mixture was refluxed for 1½ hours and extracted with ether. The organic phase was evaporated and purified by flash chromatography eluting with dichloromethane/ethanol (98/2) to give 3-methoxy-5-methylphenol. Yield=43%.

$^1$H NMR (CDCl$_3$, 400 MHz) δ2.27 (3H, s); 3.76 (3H, s); 4.78 (1H, s); 6.2–6.35 (3H, m).

A solution of 3-methoxy-5-methylphenol (28.15 g; 0.203 mol) and triflic anhydride (34.5 ml; 0.203 mol) in pyridine (100 ml) was stirred at ambient temperature for 3 hours. The mixture was acidified with 12N HCl and extracted with ether to give 3-trifluoromethanesulfonyloxy-5-methoxytoluene as a foam. Yield=89%.

$^1$H NMR (CDCl$_3$, 400 MHZ) δ2.36 (3H, s); 3.82 (3H, s); 6.60–6.74 (3H, m).

3-methoxy-5-phenyltoluene was prepared from the product of the above reaction using similar methodology to that described in Example 7, step C. Yield=83%.

$^1$H NMR (CDCl$_3$, 400 MHz) δ2.39 (3H, s); 3.85 (3H, s); 6.72 (1H, s); 6.93 (1H, s); 7.00 (1H, s); 7.3–7.58 (5H, m).

Iodotrimethyl silane (26.4 ml; 0.185 mol) was added to a solution of 3-methoxy-5-phenyltoluene (26.6 g; 0.168 mol) in trichloromethane (110 ml). The mixture was reflux for 12 hours and extracted with ether. The organic phase was evaporated and purified by flash chromatography, eluting with petroleum ethyl acetate (90/10) to give 3-methyl-5-phenylphenol as a foam. Yield=93%.

$^1$H NMR (CDCl$_3$, 400 MHz) δ2.37 (3H, s); 4.8 (1H, s); 6.65 (1H, s); 6.86 (1H, s); 6.99 (1H, s); 7.29–7.57 (5H, m).

Triflic anhydride (26 ml; 0.15 mol) was added to a solution of 3-methyl-5-phenylphenol (22.4 g; 0.15 mol) in pyridine (140 ml), at 0° C. The mixture was stirred at ambient temperature for 4 hours. After evaporation of the pyridine, the residue was acidified to pH 3 with 6N HCl and extracted with ether. The organic phase was evaporated and the residue purified by flash chromatography eluting with petroleum ether/ethyl acetate (94/6) to give 3-trifluoromethanesulfonyloxy-5-phenyltoluene as an oil. Yield=83%.

$^1$H NMR (CDCl$_3$, 400 MHz) δ2.46 (3H, s); 7.06 (1H, s); 7.26–7.56 (7H, m).

A mixture of 3-trifluoromethanesulfonyloxy-5-phenyltoluene (35.6 g; 0.128 mol), tetrakis (triphenylphosphine)palladium (12 g; 0.01 mol) and KCN (15.11 g; 0.23 mol) in dioxan (300 ml) was heated at reflux under argon an atmosphere for 24 hours. After extraction with ether and evaporating, the residue was purified by flash chromatography eluting with petroleum ether/ethyl acetate (84/6) to give 3-cyano-5-phenyltoluene. Yield=20%.

$^1$H NMR (CDCl$_3$, 400 MHz) δ2.46 (3H, s); 7.26–7.67 (8H, m).

A solution of 3-cyano-5-phenyltoluene (5.06 g; 26 mmol) and potassium hydroxide (2.94 g; 52 mmol) in methanol (40 ml) and water (60 ml) was refluxed for 24 hours. After evaporation of the methanol and filtration of the unsoluble material, the mixture was acidified to pH 2 with 6N HCl. The resulting precipitate was filtered, washed with water and dried to give 3-methyl-5-phenylbenzoic acid. Yield=65%.

$^1$HNMR (CDCl$_3$, 400 MHz) δ2.49 (3H, s); 7.25–7.65 (6H, m); 7.91 (1H, s); 8.15 (1H, s).

MP: 170° C.

A solution of 3-methyl-5-phenylbenzoic acid (3.5 g; 16.5 mmol) and concentrated H$_2$SO$_4$ (30 drops) in methanol (25 ml) was heated at reflux overnight. After evaporation to dryness, the residue was extracted with ether. The organic phase was evaporated and purified by flash chromatography eluting with petroleum ether/ethyl acetate (90/10) to give methyl 3-methyl-5-phenylbenzoate as an oil. Yield=94%.

$^1$H NMR (CDCl$_3$, 400 MHz) δ2.46 (3H, s); 3.93 (3H, s); 7.26–7.62 (6H, m); 7.84 (1H, s); 8.08 (1H, s).

A solution of methyl 3-methyl-5-phenylbenzoate (3.5 g; 15.6 mmol); N-bromosuccinimide (2.78 g; 15.6 mmol), 2,2'-azobis(2'-methylpropionitrile) (0.12 g; 0.72 mmol) and benzoylperoxide (0.12 g; 0.48 mmol) in tetrachloroamethane (120 ml) was heated at reflux for 5 hours. After evaporation to dryness, the residue was purified by flash chromatography eluting with petroleum ether/ethyl acetate (97/3) to give methyl 3-bromomethyl-5-phenylbenzoate as a solid. Yield=80%.

$^1$H NMR (CDCl$_3$, 400 MHz) δ3.95 (3H, s); 4.58 (2H, s); 7.37–8.24 (8H, m).

A solution of methyl 3-bromomethyl-5-phenylbenzoate (3.78 g; 1.23 mmol) and triphenyl phosphine (3.26 g; 1.23 mmol) in toluene (40 ml) was heated at reflux under argon atmosphere for 9 hours. The resulting solid was filtered, washed with ether and pentane to give 3-methoxycarbonyl-5-phenylbenzyl triphenylphosphonium bromide. Yield=76%.

$^1$H NMR (CDCl$_3$, 400 MHz) δ3.82 (3H, s); 5.67–5.71 (2H, d); 7.30–8.14 (23H, m).

Potassium tert-butoxide (1.05 g; 9.39 mmnol) was added to mixture of thiazol-2-yl imidazol-1-ylmethyl ketone (1.20 g; 6.25 mmol), 3-methoxycarbonyl-5-phenylbenzyl triphenyl phosphonium bromide (5.3 g; 9.39 mmol) and 18-crown-6 (0.08 g; 0.24 mmol) in dichloromethane (20 ml), at −60° C. under an argon atmosphere. After stirring overnight, at room temperature, the resulting mixture was treated with a saturated aqueous solution of ammonium chloride purified by flash chromatography eluting with dichloromethane/ethanol (95/5) to give methyl 3-[2-(thiazol-2-yl)-3-(imidazol-1-yl)prop-1-en-1-yl]-5-phenylbenzoate (Z isomer). Yield=39%.

$^1$H NMR (CDCl$_3$, 400 MHz) δ3.92 (3H, s); 5.25 (2H, s); 6.77 (1H, s): 7.05–7.83 (12H, m); 8.23 (1H, s).

A solution of methyl 3-[2-(thiazol-2-yl)-3-(imidazol-1-yl)prop-1-en-1-yl]-5-phenylbenzoate (Z isomer) (1.41 g; 3.5 mmol) in methanol (15 ml) was heated at reflux with 2N aqueous sodium hydroxide solution (4.4 ml; 8.79 mmol) for 5 hours. Methanol was then evaporated and the solution acidified to pH 6 with 6N HCl. The resulting precipitate was triturated with ethanol/ether to give 3-[2-(thiazol-2-yl)-3-(imidazol-1-yl)prop-1-en-1-yl]-5-phenylbenzoic acid as a solid.

Yield=68%.

$^1$H NMR (CDCl$_3$+CF$_3$COOD, 400 MHz) δ5.54 (2H, s); 7.42–7.64 (9H, m); 7.75 (1H, s); 8.02–8.03 (1H, d); 8.32 (1H, s); 9.06 (1H, s).

Preparation of methyl (2S)-(Z)-2-{5-[(Z)-2-(thiazol-2-yl)-3-(imidazol-1-yl)prop-1-en-1-yl]-3-phenylbenzamido}-4-methylsulfanylbutyrate The title compound was prepared using similar methodology to that described in Example 14. Yield=70%.

$^1$H NMR (DMSOd$_6$+CF$_3$COOD) δ2.07 (3H, s); 2–2.2 (2H, m); 2.5–2.7 (2H, m); 4.57 (1H, m); 5.53 (2H, s); 7.42–7.85 (11H, m); 7.90 (1H, s); 8.22 (1H, s); 8.85–8.90 (1H, s); 9.29 (1H, s).

MS (ESI) m/z 519 (MH$^+$).

Anal calcd for C$_{28}$H$_{28}$N$_4$O$_3$S$_2$, 0.95 H$_2$O C, 63.13; H, 5.30; N, 10.52; S, 12.04.

Found: C, 62.35; H, 5.37; N, 11.02; S, 11.76.

MS (ESI) m/z 533 (MH$^+$).

EXAMPLE 18

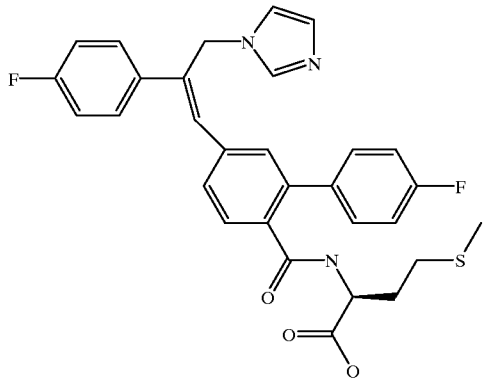

Preparation of (2S)-2-{4-[(Z)-2-(4-fluorophenyl)-3-(imidazol-1-yl)prop-1-en-1-yl]-2-(4-fluorophenyl)benzamido]-4-methylsulfanylbutyric acid The title compound was prepared by deprotecting the appropriate methyl ester using the similar methodology to that described in step A) of example 1. compound A.

Yield=51%.

$^1$H NMR (DMSO-d$_6$+CF$_3$COOD, 400 MHz) δ1.7–2.1 (2H, m); 2.01 (3H, s); 2.15–2.4 (2H, m); 4.3 5 (1H, m); 5.5 7 (2H, s); 7.1–7.7 (14H, m); 8.65 (1H, d); 9.09 (1H, s).

Anal calcd C$_{30}$H$_{27}$F$_2$N$_3$O$_3$S, 1 H$_2$O C, 63.70; H, 5.17; N, 7.43; S, 5.67.

Found: C, 63.44; H, 5.26; N, 7.45; S, 5.52.

MS (ESI) m/z 548 (MH$^+$).

Preparation of methyl (2S)-2-{4-[(Z)-2-(4-fluorophenyl)-3-(imidazol-1-yl)prop-1-en-1-yl]-2-(4-fluorophenyl)benzamido}-4-methylsulfanylbutyrate The starting material was prepared from 3-[(Z)-2-(4-fluorophenyl)-3-(imidazol-1-yl)prop-1-en-1-yl]benzoic acid (which is the Z isomer prepared in step D of Example 1, compound a)) using similar methodology to that described in step A of Example 1, compound a). Yield=38%.

$^1$H NMR (CDCl$_3$, 400 MHz) δ1.7–2.15 (2H, m); 2.03 (3H, s); 2.15–2.25 (2H, m); 3.69 (3H, s); 4.7 (1H, m); 5.10 (2H, m); 6.08 (2H, m); 6.80 (1H s); 6.95–7.45 (13H, m); 7.70 (1H, d).

Anal calcd C31H29F2N3O$_3$S C, 66.29; H, 5.20; N, 7.48; S, 5.71.

Found: C, 66.05; H, 5.29; N, 7.52; S, 5.50.

MS (ESI) m/z 562 (MH$^+$).

EXAMPLE 19

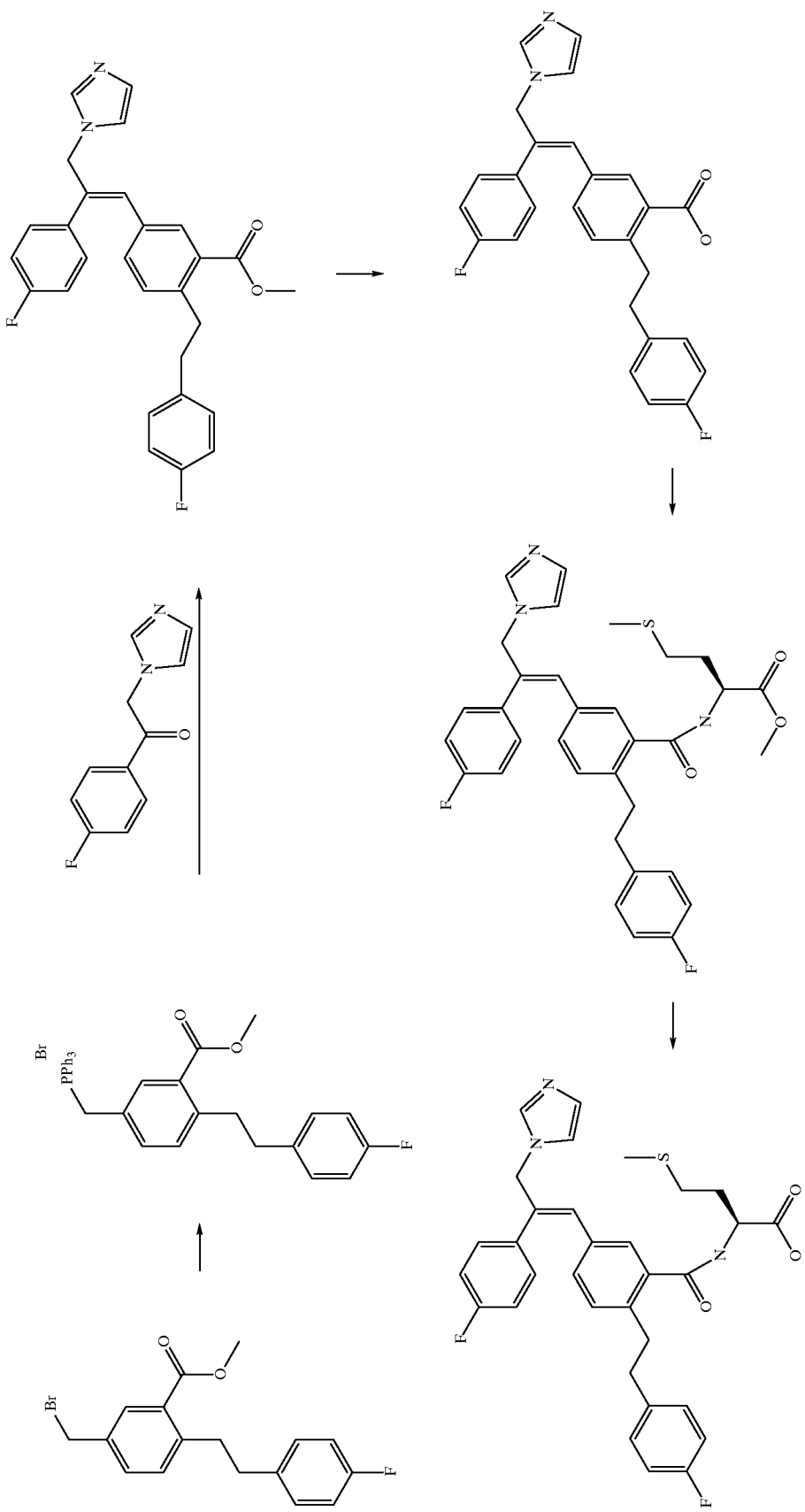

Preparation of (2S)-2-{5-[(E)-2-(4-fluorophenyl)-3-(imidazol-1-yl)prop-1-en-1-yl]-2-(2-(4-fluorophenyl)ethyl)benzamido}-4-methylsulfanylbutyric acid The title compound was prepared using similar methodology to that described in Example 1, compound a), step A. Yield=58%.

$^1$H NMR (DMSO+CF$_3$COOD, 400 MHz) δ1.95–2.05 (2H, m); 2.04 (3H, s); 2.45–2.55 (2H, m); 2.7–2.8 (2H, m); 2.85–2.95 (2H, m); 4.45–4.5 (1H, m); 5.33 (2H, s); 6.8–6.9 (2H, m); 7.0–7.2 (9H, m); 7.65 (1H, s); 7.70 (1H, s); 8.55 (1H, d); 9.05 (1H, s).

Anal calcd for $C_{32}H_{31}F_2N_3O_3S$, 1.6 $H_2O$ C, 63.58; H, 5.70; N, 6.95; S, 5.30.

Found: C, 63.86; H, 5.44; N, 6.72; S, 4.90.

MS (ESI) m/z 576 (MH$^+$).

The starting material was prepared as follows:

A mixture of dimethyl 4-bromoisophthalate (54.75 g., 200.5 mmol), water (330 ml), tributylamine (55.63 g., 300.7 mmol), 4-fluorostyrene (55.63 g., 300.7 mmol) and bis(triphenylphoshine)palladium(II)chloride (2.81 g., 4.01 mmol) was heated at reflux with stirring under an inert atmosphere for 6 hours. The reaction was cooled to ambient temperature and acidified to pH 2 with 2M HCl (700 ml). The aqueous layer was removed and the residual solid washed with water (2 L), dissolved in dichloromethane (1 L) and passed through a pad of silica, eluting with more dichloromethane (2 L). Evaporation of the dichloromethane gave a solid, which was further washed with iso-hexane (1 L), and dried to give methyl 4-[2-(4-fluorophenyl)ethenyl]-3-methoxycarbonylbenzoate (56.75 g) as a pale yellow solid.

$^1$H NMR (CDCl$_3$) δ: 3.96 (6H, 2s), 7.01–7.10 (3H, m), 7.49–7.57 (2H, m), 7.80 (1H, d), 7.97 (1H, d), 8.16 (1H, dd), 8.60 (1H, s).

MS m/e 315.3 (M+H)$^+$.

A mixture of methyl 4-[2-(4-fluorophenyl)ethenyl]-3-methoxycarbonylbenzoate (56.75 g, 180.6 mmol), ethyl acetate (900 ml), 10% palladium on carbon (6 g) was stirred under an hydrogen atmosphere for 6 hours. The catalyst was filtered and replaced with fresh catalyst (6 g). The reaction was then stirred under an hydrogen atmosphere for 16 hours. The catalyst was filtered and the filtrate evaporated to dryness to give as a colourless gum, methyl 4-(4-fluorophenethyl)-3-methoxycarbonylbenzoate (55.00 g).

$^1$H NMR (CDCl$_3$) δ: 2.84–2.93 (2H, m), 3.25–3.33 (2H, m), 3.93 (6H, 2s), 6.90–7.00 (2H, m), 7.09–7.16 (2H, m), 7.22–7.28 (1H, m), 8.05 (1H, dd), 8.57 (1H, s).

MS m/e 317.3 (M+H)$^+$.

A mixture of methyl 4-(4-fluorophenethyl)-3-methoxycarbonylbenzoate (51.00 g., 161.22 mmol), dioxane (650 ml), methanol (650 ml), sodium hydroxide (7.10 g., 177.35 mmol) and water (100 ml) was stirred at ambient temperature under an inert atmosphere for 16 hours. The reaction was evaporated to dryness, water (500 ml) was added to the residue and the mixture extracted with diethyl ether. The organic extracts were dried and evaporated to dryness to give recovered methyl 4-(4-fluorophenethyl)-3-methoxycarbonylbenzoate (7 g). The aqueous layer was acidified to pH 2 with 2M HCl (300 ml) and extracted with ethyl acetate(300 ml). The organic extracts were dried. filtered and evaporated to dryness to give as a white solid 4-(4-fluorophenethyl)-3-methoxycarbonylbenzoic acid (42.00 g).

$^1$H NMR (DMSO d$_6$) δ: 2.77–2.85 (2H, m), 3.16–3.24 (2H, m), 3.85 (3H, s), 7.04–7.12 (2H, m), 7.17–7.25 (2H, m), 7.45 (1H, d), 8.00 (1H, dd), 8.535 (1H, s).

MS m/e 301.4 (M−H)$^-$.

A mixture of 4-(4-fluorophenethyl)-3-methoxycarbonylbenzoic acid (16.5 g, 54.88 mmol), tetrahydrofuran(500 ml) and borane in tetrahydrofuran (1M; complex, 218 ml, 218 mmol) was stirred under an inert atmosphere at reflux for 6 hours. The reaction was cooled to ambient temperature and methanol (1 L) was added. It was then evaporated to dryness to give a dark oil which was purified by flash chromatography using iso-hexane/ethyl acetate (1:1) as eluant to give as a clear gum methyl 2-(4-fluorophenethyl)-5-hydroxymethylbenzoate (13.10 g).

$^1$H NMR (CDCl$_3$) δ: 1.74 (1H, t), 2.82–2.92 (2H, m), 3.17–3.27 (2H, m), 3.91 (3H, s), 4.71 (2H, d), 6.91–6.99 (2H, m), 7.11–7.20 (3H, m), 7.41 (1H, d), 7.91 (1H, s).

MS m/e 289 (M+H)$^+$.

A mixture of methyl 2-(4-fluorophenethyl)-5-hydroxymethylbenzoate (13.10 g., 45.43 mmol), carbon tetrabromide (18.08 g, 54.52 mmol) and triphenylphosphine (14.30 g, 54.52 mmol) in dichloromethane (400 ml) was stirred at ambient temperature for 4 hours. More carbon tetrabromide (7.54 g, 23.00 mmol) and triphenylphosphine (5.96 g, 23.00 mmol) in dichloromethane (50 ml) were added and then stirred for a further 2 hours. The reaction was applied directly to a silica flash column and eluted with iso-hexane/ethyl acetate (92.5:7.5) to give as a clear gum methyl 2-(4-fluorophenethyl)-5-bromomethylbenzoate (9.30 g).

$^1$H NMR (CDCl$_3$) δ: 2.81–2.91 (2H, m), 3.19–3.27 (2H, m), 3.91 (3H, s), 4.48 (2H, s), 6.91–7.00 (2H, m), 7.12–7.17 (3H, m), 7.44 (1H, dd), 7.95 (1H, s).

MS m/e's 351 and 353 (M+H)$^+$.

A mixture of methyl 2-(4-fluorophenethyl)-5-bromomethylbenzoate (2.5 g; 7.1 mmol) and triphenylphosphine (2.1 g; 7.9 mmol) in toluene (50 ml) was heated at reflux for 3 hours. The solvent was evaporated and the residue was triturated in diethyl ether, filtered and washed three times with diethylether to give 3-methoxycarbonyl-4-[2-(4-fluorophenyl)ethyl]benzyl triphenylphosphonium bromide as a white solid. Yield=96%.

$^1$H NMR (CDCl$_3$, 400 MHz) δ2.75–2.80 (2H, m); 3.11–3.16 (2H,m); 3.75 (3H, s); 5.53 (2H, d); 6.88–7.08 (5H, m); 7.5–7.8 (17 H, m).

Potassium ter-butoxide (0.735 g; 6 mmol) was added to a mixture of 4-fluorophenyl imidazol-1-ylmethyl ketone (0.816 g; 4 mmol), 3-methoxycarbonyl-4-[2-(4-fluorophenyl)ethyl]benzyl triphenylphosphonium bromide (3.7 g; 6 mmol) and 18-crown-6 (50 mg) in anhydrous dichloromethane (50 ml), at 0° under an inert atmosphere The mixture was stirred at room temperature for 5 hours, washed with brine, dried and purified by flash chromatography eluting with dichloromethane/ethanol (99/1) to give successively the Z and E isomers methyl 2-[2-(4- fluorophenyl)ethyl]-5-[2-(4-fluorophenyl)-3-(imidazol-1-yl)prop-1-en-yl]benzoate Yield=45%.

$^1$H NMR (CDCl$_3$, 400 MHz) δ2.76–2.80 (2H, m); 3.10–3.15 (2H, m); 3.8 (3H, s); 4.85 (2H, s); 6.48 (1H, s); 6.9–7.1 (10 H, m); 7.4–7.7 (4H, m).

MS (ESI) m/z 459 (MH$^+$).

To a solution of the previous methyl ester (0.760 g; 1.6 mmol) in methanol (20 ml) was added 2N aqueous sodium hydroxide (2.5 ml; 5 mmol). The mixture was heated at reflux for 4 hours. Methanol was evaporated and the aqueous residue was acidified with 12N HCl (400 μl; 5 mmol). The residue was triturated in diethyl ether to give 2-[2-(4-fluorophenyl)ethyl]-5-[2-(4-fluorophenyl)-3-(imidazol-1-yl)prop-1-en-1-yl]benzoic acid as a white solid which was dried and used without further purification Yield=72%.

$^1$H NMR (DMSOd$_6$+CF$_3$COOD, 400 MHz) δ2.73–2.8 (2H, m); 3.07–3.11 (2H, m);

5.3 (2H, s); 6.85–7.2 (12H, m); 7.7 (1H, s); 9.08 (1H, s).

MS (ESI) m/z 445 (MH$^+$).

A mixture of 2-[2-(4-fluorophenyl)ethyl]-5-[(E)-2-(4-fluorophenyl)-3-(imidazol-1-yl)prop-1-en-1-yl]benzoic acid (0.3 g; 0.67 mmol), EDC (0.154 g; 0.8 mmol), HOBT (0.108 g; 0.8 mmol), DMAP (0.090 g; 0.74 mmol), L-methionine methyl ester hydrochloride (0.2 g; 1 mmol) and N-Methylmorpholine (110 μl; 1 mmol) in dichloromethane (20 ml) was stirred at room temperature overnight. The organic phase was washed with aqueous sodium bicarbonate, dried and evaporated. The residue was purified by flash chromatography. eluting with a gradient of dichloromethane/ethanol (1–3%) to give methyl (2S)-2-{5-[(E)-2-(4-fluorophenyl)-3-(imidazol-1-yl)prop-1-en-1-yl]-2-(2-(4-fluorophenyl)ethyl)benzamido}-4-methylsulfanylbutyrate as a white solid foam Yield=50%.

$^1$H NMR (CDCl$_3$, 400 MHz) δ1.9–2 (1H, m); 2.1 (3H, s); 2.15–2.25 (1H, m); 2.4–2.5 (2H, m); 2.8–2.85 (2H, m); 2.9–3 (2H, m); 3.8 (3H, s); 4.75–4.8 (1H, m); 4.85 (2H, s); 5.95 (1H, d); 6.48 (1H, s); 6.85–7.06 (13H, m); 7.35–7.4 (1H, m).

MS (ESE) m/z 590 (MH$^+$)

Anal calcd for C$_{33}$H$_{33}$F$_2$N$_3$O$_3$S C, 67.21; H, 5.64; N, 7.13; S, 5.44.

Found: C, 66.76; H, 5.90; N, 6.82; S, 5.27.

EXAMPLE 20

Preparation of a) Methyl (2R)-2-{3-[(E)-2-(4-fluorophenyl)-3-(imidazol-1-yl)prop-1-en-1-yl]-benzamido}-4-methylsulphanylbutyrate b) Methyl (2S)-2-{3-[(E)-2-(4-fluorophenyl)-3-(imidazol-1-yl)-prop-1-enyl]-benzamido}-4-ethylsulphanylbutyrate c) Methyl 2-{3-[(E)-2-(4-fluorophenyl)-3-(imidazol-1-yl)-prop-1-enyl]-benzamido}-3-(2-thienyl) propanoate d) Methyl (2S)-2-{3-[(E)-2-(4-fluorophenyl)-3-(imidazol-1-yl)-prop-1-enyl]-benzamido}-6-aminohexanoate e) (2S)-2-{3-[(E)-2-(4-Fluorophenyl)-3-(imidazol-1-yl)prop-1-enyl]benzamido}-4-methylsulfanylbutyramide f) Trifluoromethanesulfonyl (2S)-2-{3-[(E)-2-(4-fluorophenyl)-3-(imidazol-1-yl)prop-1-enyl]benzamido}-4-methylsulfanylbutyramide; and g) Methanesulfonyl (2S)-2-{3-[(E)-2-(4-fluorophenyl)-3-(imidazol-1-yl)prop-1-enyl]-benzamido}-4-methylsulfanylbutyramide

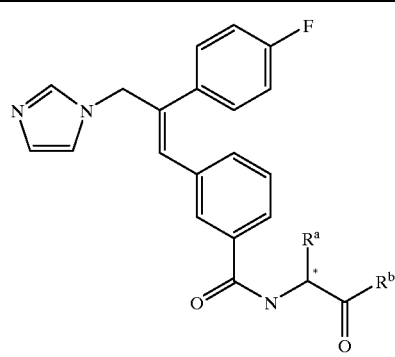

| Compound | * | R$^a$ | R$^b$ |
|---|---|---|---|
| a) | (R) | CH$_2$CH$_2$SMe | OMe |
| b) | (S) | CH$_2$CH$_2$SEt | OMe |
| c) | (R/S) | thien-2-ylmethyl | OMe |
| d) | (S) | (CH$_2$)$_4$NH$_2$ | OMe |
| e) | (S) | CH$_2$CH$_2$SMe | NH$_2$ |
| f) | (S) | CH$_2$CH$_2$SMe | NHSO$_2$CF$_3$ |
| g) | (S) | CH$_2$CH$_2$SMe | NHSO$_2$CH$_3$ |

Preparation of Compound a)

A mixture of E isomer from Example 1, compound a), step D (0.322 g, 1.0 mmol), HOBT (0.15 g, 1.1 mmol) and EDC (0.21 g, 1.1 mmol) was stirred until solution. N-methylmorpholine (0.25 ml, 2.2 mmol) and D-methionine methyl ester hydrochloride (0.22 g, 1.1 mmol) were added and the mixture stirred overnight at room temperature, washed with water and saturated sodium hydrogen carbonate solution (aqueous). The organic phase was evaporated and the residue purified on silica eluting with 1% methanol/dichloromethane. Appropriate fractions were evaporated to give the desired material as a foam (0.15 g, 32%).

¹H NMR (DMSO, 300 MHz) δ2.01(2H, m); 2.03(3H, s); 2.50(2H, m); 3.61(3H, s); 4.51(1H, q); 5.04(2H, s); 6.63(1H, s); 6.83(1H, s); 6.97(1H, d); 7.11(5H, m); 7.20(1H, t); 7.53(2H, d); 7.60(1H, d); 8.63(1H, d)

MS (ES+) m/z 468 (MH⁺).

Preparation of Compound b)

Compound b) was synthesised in a similar manner to that described for compound a) but substituting L-ethionine methyl ester hydrochloride (in place of the D-methionine methyl ester hydrochloride).

¹H NMR (DMSO, 300 MHz) δ1.15(3H,t); 1.99(2H, q); 2.43–2.62(4H, m); 3.61(3H, s); 4.52(1H, q); 5.03(2H, s); 6.63(1H, s); 6.83(1H, s); 6.97(1H, d); 7.12(5H, m); 7.21(1H, t); 7.52(2H, d); 7.60(1H, d); 8.64(1H, d)

MS (ES+) m/z 482 (MH+)

Preparation of Compound c)

Compound c) was synthesised in a similar manner to that described for compound a) but substituting 3-(2-thienyl)-DL-alanine methyl ester hydrochloride (in place of the L-methionine methyl ester hydrochloride).

¹H NMR (DMSO, 300 MHz) δ3.34(2H, m); 3.63(3H, s); 4.57(1H, m); 5.05(2H, s); 6.62(1H, s); 6.84(1H, s); 6.92(2H, m); 6.96(1H, d); 7.11(5H, m); 7.20(1H, t); 7.31(1H, m); 7.51(2H, s); 7.57(1H, d); 8.80(1H, d)

MS (ES+) m/z 490 (MH+).

Preparation of Compound d)

A) A mixture of (2S)-2-{3-[(E)-2-(2-(4-fluorophenyl)-3-(imidazol-1-yl)prop-1-enyl]benzamido}-6-aminohexanoic acid dihydrochloride (1.28 g, 1.65 mmol), dichloromethane (15 ml) and oxalylchloride (0.45 ml, 5.2 mmol) was stirred for half an hour at room temperature, evaporated, to dryness, treated with methanol (20 ml) and again evaporated to dryness. The residue was dissolved in water treated with saturated sodium hydrogen carbonate solution (aqueous), extracted with dichloromethane and evaporated to give compound d) (1.12 g).

¹H NMR (DMSO, 300 MHz) δ1.30(2H, m); 1.44(2H, m); 1.74(2H, m); 3.09(2H, q); 3.60(3H, s); 4.32(1H, m); 5.03 (2H, s); 6.63(1H, s); 6.83(1H, s); 6.93(1H, d); 7.11(5h, m); 7.20(1H, t); 7.52(2H, d); 7.61(1H, d); 8.56(1H, d); 8.90(1H, m)

MS (ES+) m/z 465 (MH+)

The desired starting material was prepared as follows:

B) Butyl (2S)-2-{3-[(E)-2-(4-fluorophenyl)-3-(imidazol-1-yl)-prop-1-enyl]-benzamido}-6-N-BOC-hexanoate (1.35 g, 83%) was synthesised in a similar manner to that described for compound a) but substituting N-ε-tert-butoxycarbonyl-L-lysine-tert-butyl ester hydrochloride (in place of the L-methionine methyl ester hydrochloride)

¹H NMR (DMSO, 300 MHz) δ1.30(4H, m); 1.32(9H, s); 1.37(9H, s); 1.69(2H, m); 2.88(2H, m); 4.18(1H, m); 5.04 (2H, s); 6.63(1H, s); 6.73(1H, m); 6.83(1H, s); 6.95(1H, d); 7.09(5H,m); 7.20(1H, t); 7.52(2H, d); 7.60(1H, d); 8.40(1H, d)

MS (ES+) m/z 607 (MH+)

C) A mixture of the product from step B (1 g, 1.65 mmol), dichloromethane (10 ml) and 2.7M hydrogen chloride in ethyl acetate (10 ml, 16.4 mmol) was stirred at room temperature overnight. The mixture was evaporated to dryness, dissolved in water, washed with ethyl acetate and evaporated to dryness to give (2S)-2-{3-[(E)-2-(4-fluorophenyl)-3-(imidazol-1-yl)-prop-1-enyl]-benzamido}-6-aminohexanoic acid dihydrochloride as a sticky glass (1.28 g).

¹H NMR (DMSO, 300 MHz) δ1.39(2H,m); 1.57(2H, m); 1.77(2H, m); 2.74(2H, m); 4.32(1H, m); 5.33(2H, s); 6.91 (1H,s); 7.00(1H, t); 7.10–7.27(5H, m); 7.54–7.73(5H, m); 7.96(3H, d); 8.51)1H, d); 9.08(1H, s);

MS (ES+) m/z 451 (MH+)

Preparation of Compound e)

A) A mixture of E isomer from Example 1, compound a), step D (0.23 g, 0.7 mmole), L-methionine amide TFA salt (0.18 g, 0.7 mmole), HOBT (0.10 g, 0.77 mmole), EDC (0.15 g, 0.77 mmole) and N-methyl morpholine (0.17 ml, 1.5 mmole) in dichloromethane (25 ml) was stirred at room temp for 18 hours. The mixture was washed with water and the organic phase dried over MgSO₄, evaporated, purified on silica eluting with a gradient of 100% dichloromethane to 3% methanol/dichloromethane and evaporated to give the desired material as a white foam. (0.17 g, 54%) 90% pure.

¹H NMR (DMSO-D6, 300 MHz) d 1.85–2.05 (5H, m); 2.3–2.5 (2H, m); 4.4 (1H, m); 5.0 (2H, s); 6.60–8.30 (14H, m)

MS (ES) m/z 453 (MH⁺)

Preparation of Compound f)

A) Compound f) was prepared in a similar manner to that described for compound a), but substituting trifluoromethanesulfonyl-L-methionine carboxamide for D-methionine methyl ester. Yield=8%, 90% pure.

¹H NMR (DMSO-D6, 300 MHz) d 1.85–2.05 (5H, m); 2.40 (2H, m); 4.30 (1H, m); 5.05 (2H, s); 6.65–7.95 (13H, m)

MS (ES⁺) m/z 583 (M–H)⁻

The trifluoromethanesulfonyl-L-methionine carboxamide was prepared as follows.

B) A mixture of L-BOC methionine (1.09, 4.0 mmole), trifluoromethane sulfonamide (0.72 g, 4.8 mmole), EDC (1.15 g, 6.0 mmole) and DMAP (0.98 g, 8.0 mmole) in dry DMF (10 ml) was stirred at room temperature for 48 hours. Most of the DMF was removed by rotary evaporation. The residue was dissolved in dichloromethane, washed with 1M citric acid, dried with MgSO₄, evaporated and purified on silica. eluting with dichloromethane to give a colourless gum (1.28 g, 84%)

¹H NMR (DMSO-D6, 300 MHz) d 1.30 (9H, s); 1.65–2.0 (5H, m); 2.40 (2H, t); 3.8 (1H, m); 6.95 (1H, d); 8.15 (1H, m)

MS (ES⁻) m/z 379 (M–H)⁻

C) The product of step B) (1.28 g, 3.3 mmole) was dissolved in methanol (5 ml) and 1M HCl/diethylether (10.1 ml, 10 mmole) added, stirred at room temp for 48 hours. The reaction mixture was evaporated and the resulting gum titurated with diethyl ether and the ether decanted. This tituration was repeated 5 times resulting in a colourless gum which began to crystallise on standing (1.04 g, 100% yield).

¹H NMR (CDCl₃, 300 MHz) d 2.10 (3H, s); 2.40 (2H, m); 2.75 (2H, m); 4.30 (1H, bs); 6.80 (1H, m); 8.30 (1H, bs); 8.80 (1H,bs)

MS (ES⁻) m/z 279 (M–H)⁻

Preparation of Compound g)

A) Compound g) was prepared in a similar manner to that described for compound a), but substituting L-methionine methane sulfonamide for D-methionine methyl ester. Yield=13%

¹H NMR (DMSO-D6, 300 MHz) d 1.95 (2H, m); 2.0 (3H, s); 2.40 (2H, m); 3.10 (3H, s); 4.40 (1H, m); 5.05 (2H, s); 6.65–7.70 (12H, m); 8.45 (1H, d)

MS (ES⁻) m/z 529 (M–H)⁻

EA Calcd for C25H27FN4O4S2.1.0 H₂O C, 54.7; H, 5.3; N, 10.2; S, 11.7. Found: C, 54.6; H, 5.5; N, 9.9; S, 11.3.

The methanesulfonyl-L-methionine carboxamide was prepared as follows:

B) The BOC protected methanesulfonyl-L-methionine carboxamide was prepared in a similar manner to that described for compound f) step B) but substituting methane sulfonamide for trifluoromethane sulfonamide. Yield=100%

¹H NMR (DMSO-D6), 300 MHz) d 1.35 (9H, s); 1.80 (2H, m); 2.0 (3H, s); 2.40 (2H, m); 3.20 (3H, s); 4.0 (1H, m); 7.20 (1H, d)

MS (ES⁺) m/z 327 (MH)⁺, 344 (M+NH₄)⁺

C) The methanesulfonyl-L-methionine carboxamide was prepared in a similar manner to that described for compound f) step C). Yield=100%

¹H NMR (DMSO-D6, 300 MHz) d 2.0 (5H, m); 2.55 (2H, m); 3.25 (3H, s); 4.0 (1H, m); 8.60 (2h, bs)

MS (ES⁺) m/z 227 (MH)⁺

EXAMPLE 21

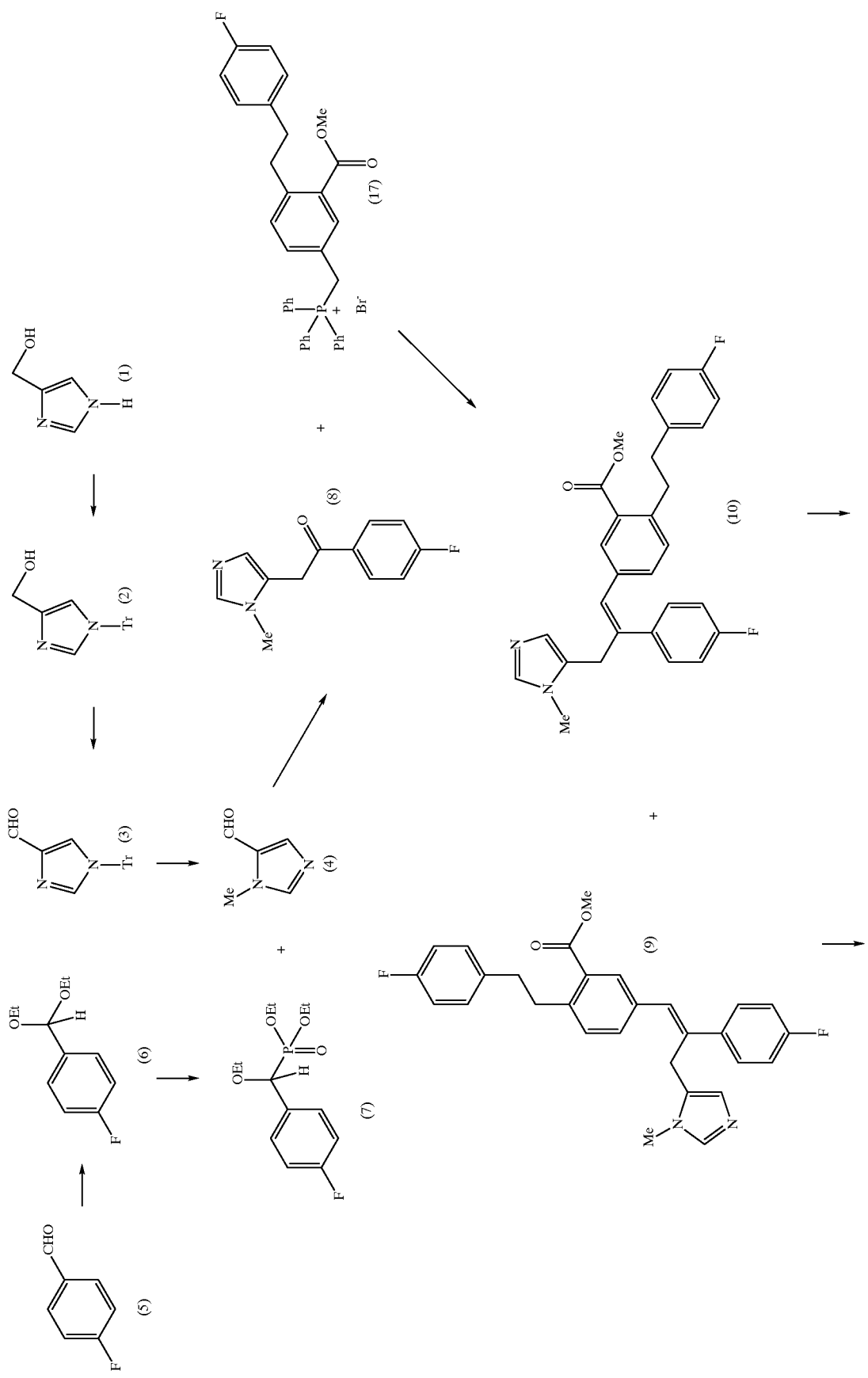

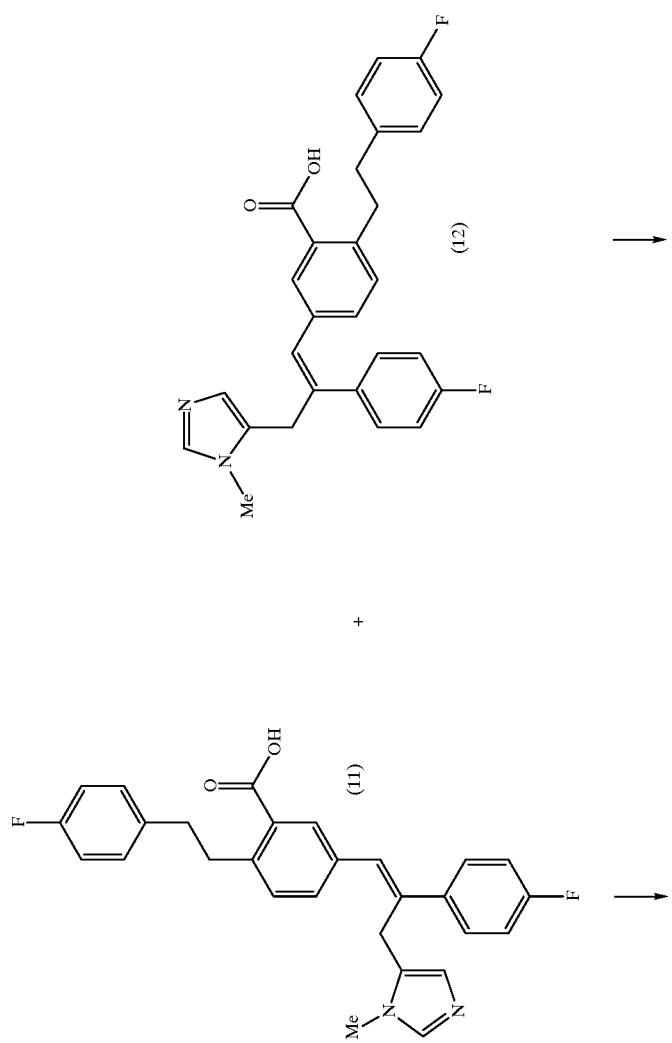

-continued
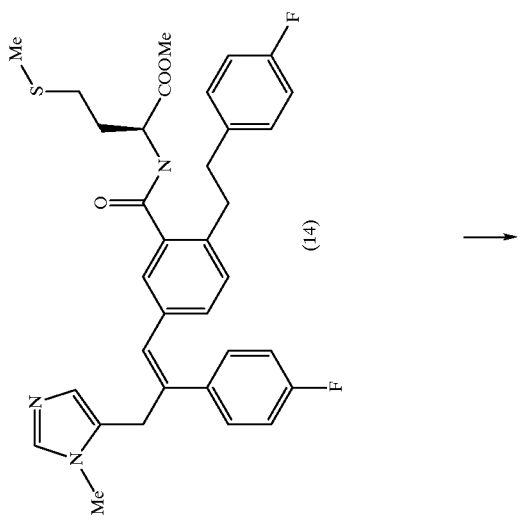
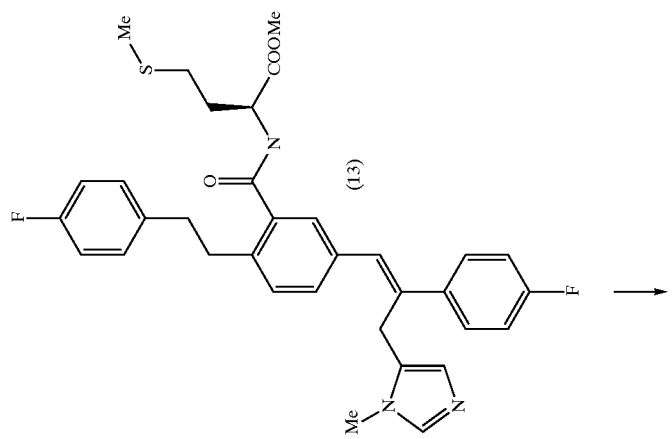

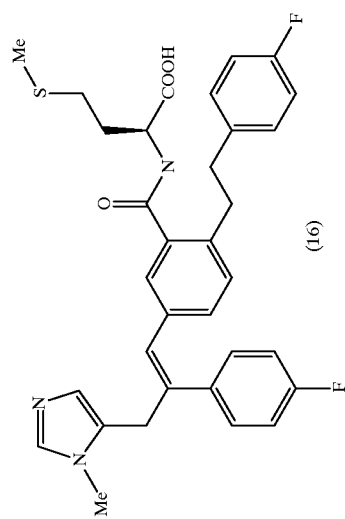
(16)
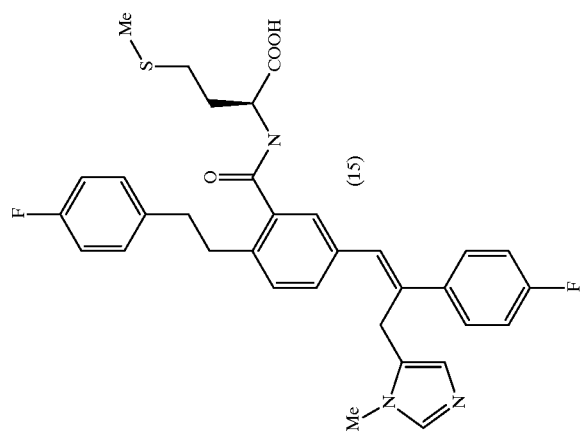
(15)

Preparation of Compounds (15) and (16)

A mixture of compound (13) (0.025 g), sodium hydroxide (0.033 g), methanol (5 ml) and water (1 ml) was stirred at ambient temperature under a nitrogen atmosphere for 2 hours. The reaction was acidified with hydrochloric acid (2M) to pH 2 and the methanol/water evaporated away. The residue was treated with water (1 ml), the water removed and the resulting gum washed with more water (0.5 ml) and the water again removed. The residue was dried under high vac. to give compound (15) as a white solid (0.02 g).

$^1$H NMR (DMSO-$d_6$) δ: 1.70–2.00 (2H, m), 1.90 (3H,s), 2.10–2.40 (2H, m), 2.55–2.94 (4H, m), 3.70 (3H,s), 4.05 (2H, s), 4.38 (1H, m), 6.90–7.30 (10 H, m), 7.40–7.65 (3H, m), 8.55 (1H,d), 8.90 (1H,s).

MS (MH$^+$). 590.3

Elemental Analysis: Found: C,51.10; H, 4.40; N, 5.20; S, 4.4.

2HCl.2NaCl Theory C, 50.8; H, 4.49; N, 5.38; S, 4.1.

Compound (16) was prepared from compound (14) using a similar method to that used to prepare compounds (15).

$^1$H NMR (DMSO-$d_6$) δ: 2.0–2.3(2H, m), 2.16(3H, s), 2.6–2.8(2H, m), 2.8–3.15(4H, m), 3.92(3H, s), 4.1(2H, s), 4.59(1H, m), 6.7(1H, s), 6.9(1H, d), 7.05–7.43(10H, m), 7.46(1H, s), 8.55(1H, d), 9.15(1H, s)

MS (MH$^+$). 590.3

Elemental Analysis: Found: C,56.40; H, 5.00; N, 5.90; S, 4.80.

2HCl.0.75NaCl Theory C, 56.00; H, 4.95; N, 5.94; S, 4.53

The starting materials for compounds (15) and (16) were prepared as follows:

Preparation of 1-methyl-1H imidazole-5-carboxaldehyde, compound(4)

See:

J. Med. Chem.: 1996,Vol.39, pp353–358

Tet. Letts: Vol. 53, No.22 pp 7605–7614, 1997

Preparation of 4-Fluorobenzaldehyde diethyl acetal, compound (6)

A mixture of 4-fluorobenzaldehyde, compound (5) (20 g, 17.3 ml, 161.15 mmol), triethylorthoformate (29.85 g, 33.5 ml, 201.43 mmol) and para-toluenesulphonic acid (0.28 g, 1.61 mmol ) in ethanol (100 ml) was stirred for 16 hours under a nitrogen atmosphere at ambient temperature. The mixture was treated with anhydrous sodium carbonate to pH 9, stirred for a further five minutes and then filtered and the filtrate evaporated to dryness. Purification by flash column chromatography eluting with iso-hexane/dichloromethane (1:1) and then with iso-hexane/ethyl acetate (9:1) gave a clear oil, compound (6)(22.77 g, 71% Yield).

$^1$H NMR (CDCl$_3$) δ: 1.23 (6H, t), 3.46–3.65 (4H, m), 5.48 (1H, s), 7.03 (2H, t), 7.45 (2H,dd).

MS (MH$^+$). 198

Preparation of Compound (7)

Boron trifluoride etherate was added dropwise to a mixture of acetal, compound (6)(22.77 g, 114.86 mmol) and triethylphosphite (19.09 g, 20 ml, 114.86 mmol) in dichloromethane (200 ml) stirred at −20° C. under a nitrogen atmosphere. The reaction was then stirred at ambient temperature for 18 hours, treated with water (50 ml) and stirred for a further 5 minutes. The organic phase was separated, dried and evaporated to dryness. Purification was by flash column chromatography, eluting with iso-hexane/dichloromethane (1:1), dichloromethane and dichloromethane/ethyl acetate (4:1) gave a clear gum, compound (7) (28.73 g, 86%. Yield).

$^1$H NMR (CDCl$_3$) δ: 1.18 −1.30 (9H,m), 3.45–3.62 (2H, m), 3.93–4.16 (4H, m), 4.60 (1H, d), 7.00–7.11 (2H, t), 7.40–7.48(2H,m).

MS (MH$^+$). 290

Preparation of Compound (8)

A solution of n-butyl lithium (1.6 M in hexane) (7 ml, 11.21 mmol) was added dropwise over 5 minutes to a solution of compound (7) (3.26 g, 11.21 mmol) in tetrahydrofuran (45 ml) cooled to −78° C. under a nitrogen atmosphere and the mixture then stirred for a further 10 minutes. A solution of 1-methyl-1H-imidazole-5-carboxaldehyde, compound (4) (0.95 g, 8.63 mmol) in tetrahydroftiran (45 ml) was then added over 10 minutes to the reaction which was stirred for a further 20 minutes after the addition was completed. It was then treated with water (30 ml), allowed to warm to ambient temperature, acidified with hydrochloric acid (10M, 10 ml) and refluxed for 18 hours. The reaction mixture was then cooled back down to ambient temperature, basified with saturated aqueous sodium bicarbonate to pH 8, the tetrahydrofuran evaporated away and the aqueous residue extracted with ethyl acetate (2×50 ml). The combined organic extracts were washed with brine. dried and evaporated to dryness. Purification by flash column chromatography eluting with dichloromethane/methanol (19:1) and dichloromethane/methanol(9:1) gave an orange solid, compound (8) (1.16 g, 62% Yield).

$^1$H NMR (CDCl$_3$) δ: 3.60 (3H, s), 4.26 (2H, s), 6.93 (1H, s), 7.11–7.21 (2H, m), 7.45 (1H, s), 8.00–8.11 (2H, m).

MS (MH$^+$). 219

Preparation of Compound (17)

See Example 19.

Preparation of Compounds (9) and (10)

A solution of potassium tertiary-butoxide (1M, 3 ml in THF) was added dropwise to a mixture of compound (8) (0.5 g), compound (17) and 18-crown-6 (0.05 g) in dichloromethane (50 ml) stirred under a nitrogen atmosphere at ambient temperature. The reaction was then stirred for a further 2 hours, treated with saturated ammonium chloride solution (50 ml) and the organic layer separated. It was then washed with saturated brine solution, dried and applied directly to a silica flash column which was eluted with ethyl acetate, ethyl acetate/methanol (9:1) and ethyl acetate/methanol (4:1) to give compound (9) (0.15 g) and compound (10) (0.16 g) as colourless gums. Compound (9):

$^1$H NMR (CDCl$_3$) δ: 2.85–2.91 (2H, m), 3.19–3.28 (2H, m), 3.50 (3H, s), 3.82–3.90 (5H,d), 6.68 (1H,s),6.92–7.08 (5H,m), 7.13–7.18 (3H,m), 7.30–7.60 (2H, m), 7.65–7.73 (2H, m), 7.81 (1H, d).

MS (MH$^+$). 473.3

Compound (10):

$^1$H NMR (CDCl$_3$) δ: 2.73–2.83 (2H, m), 3.05–3.16 (2H, m), 3.55 (3H, s), 3.71 (2H,s) 3.80 (3H,s), 6.28 (1H, s), 6.85–7.13 (11 H,m),7.43 (1H,s), 7.47 (1H,s).

MS (MH$^+$). 473.3

Preparation of Compounds (11) and (12)

A mixture of compound (9) (0.15 g), sodium hydroxide (0.127 g), methanol (10 ml) and water (1 ml) was stirred under an atmosphere of nitrogen at reflux for 3 hours, cooled to ambient temperature and the methanol evaporated off. The residue was treated with aqueous citric acid (1M, 10 ml) and extracted with ethyl acetate. The organic extracts were dried and evaporated to dryness to give compound (11) as a colourless gum (0.145 g).

Compound (10) was similarly converted to compound (12) which was isolated as a white solid.

Compound (12)

$^1$H NMR (DMSO-$d_6$) δ: 2.70 (2H, m), 3.03 (2H, m), 3.63 (3H, s), 3.83 (2H,s), 6.46 (1H, s), 6.89(2H,m), 6.96–7.30 (9H,m), 7.45 (1H,s), 8.03 (1H,s), 11.50–12.70 (1H,br).

MS (MH$^+$). 459

Preparation of Compounds (13) and (14)

A mixture of compound (11) (145 g), L-methionine methyl ester HCl (0.196 g), DMAP (0.28 g), EDC (0.126 g) and dichloromethane (20 ml) was stirred under a nitrogen atmosphere at ambient temperature for 16 hours. The reaction mixture was then washed with aqueous citric acid (1M 20 ml), saturated brine, dried and applied directly to a silica flash column which was then eluted with ethyl acetate and ethyl acetate/methanol (9:1) to give compound (13) as a colourless gum. This was then redissolved in ethyl acetate and treated with ethereal HCl (10 ml). The resulting solid was isolated by centrifuging, further washing with more diethyl ether and finally drying under high vac. to give compound (13) as a white solid (0.13 g).

$^1$H NMR (DMSO-$d_6$) δ: 1.84–2.16 (2H, m), 2.00 (3H,s), 2.33–2.67 (2H, m), 2.71–3.10(4H, m), 3.62 (3H,s), 3.80 (3H, s), 4.16 (2H, s), 4.60 (1H,m),7.00–7.44 (10 H, m),7.50–7.80 (3H, m), 8.80 (1H,d), 9.02 (1H,s), 13.90–14.6 (1H, brs).

MS (MH$^+$). 604.4

Elemental Analysis: Found: C, 62.1; H, 5.60; N, 6.10. 1HCl.1H$_2$O Theory C, 62.0; H, 5.77; N, 6.38

Compound (14) was prepared from compound (12) using a similar method to that used to prepare compound (13).

$^1$H NMR (DMSO-$d_6$) δ: 1.84–2.16 (2H, m), 2.00 (3H,s), 2.33–2.67 (2H, m), 2.71–3.00 (4H, m), 3.62 (3H,s), 3.80 (3H, s), 4.00 (2H, s), 4.52 (1H,m), 6.55(1H,s),6.80(1H,d) 6.92–7.30 (10 H, m), 7.32 (1H, s), 8.60 (1H,d), 9.03 (1H,s), 14.00–14.90 (1H, brs).

MS (MH$^+$). 604.4

Elemental Analysis: Found: C,62.0; H, 5.40; N, 6.20. 1HCl.1H$_2$O Theory C,62.0; H, 5.77; N, 6.38

EXAMPLE 22
Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1 M Sodium hydroxide solution | 15.0% v/v |
| 0.1 M Hydrochloric acid | |
| (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1 M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A compound which is an inhibitor of ras farnesylation of Formula I:

Formula I

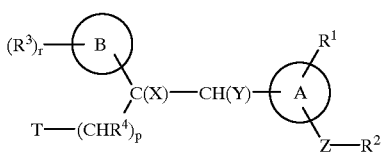

Formula III

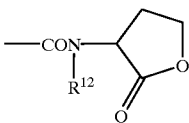

wherein

T is of the formula:

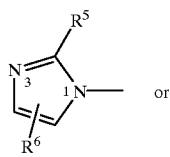 (1)

or

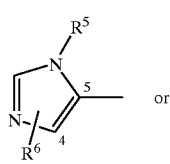 (2)

or

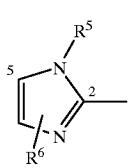 (3)

A is aryl or heteroaryl;
B is aryl or heteroaryl;
X and Y are hydrogen, or, together X and Y form a bond;
$R^1$ represents a group of the Formula II:

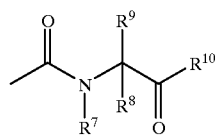

Formula II wherein $R^7$ is hydrogen or $C_{1-4}$alkyl, $R^8$ is hydrogen or $C_{1-4}$alkyl, $R^9$ is of the formula —$(CH_2)_q$—$R^{11}$ wherein q is 0–4 and $R^{11}$ is $C_{1-4}$alkylsulfanyl, $C_{1-4}$alkylsulfinyl, $C_{1-4}$alkylsulfonyl, hydroxy, amino, $C_{1-4}$alkoxy, carbamoyl, N-($C_{1-4}$alkyl) carbamoyl, N,N-(di$C_{1-4}$alkyl)carbamoyl, $C_{1-4}$alkyl, phenyl, thienyl, or $C_{1-4}$alkanoylamino, $R^{10}$ is hydroxy, heterocyclyl$C_{1-4}$alkoxy, heterocyclyloxy, $C_{5-7}$cycloalkyl$C_{1-4}$alkoxy, $C_{1-4}$alkoxy, amino, or —NH—$SO_2$—$R^{13}$ wherein $R^{13}$ represents $CF_3$, $C_{1-4}$alkyl, aryl, heteroaryl, aryl $C_{1-4}$alkyl or heteroaryl$C_{1-4}$alkyl or $R^1$ represents a lactone of Formula III:

wherein $R^{12}$ is hydrogen or $C_{1-4}$alkyl;
the group of Formula II or III (having L or D configuration at the chiral alpha carbon in the corresponding free amino acid);
$R^2$ represents hydrogen, aryl or heteroaryl;
Z represents a direct bond methylene, ethylene, vinylene, oxy, —$CH_2$—O— or —O—$CH_2$—;
$R^3$ is selected from at least one of hydrogen, $C_{1-4}$alkyl, halogen, hydroxy, $C_{1-4}$alkoxy, $C_{1-4}$alkanoyl, $C_{1-4}$alkanoyloxy, amino, $C_{1-4}$alkylamino, di($C_{1-4}$alkyl) amino, $C_{1-4}$alkanoylamino, nitro, cyano, carboxy, carbamoyl, $C_{1-4}$alkoxycarbonyl, thiol, $C_{1-4}$alkysulfanyl, $C_{1-4}$alkylsylfinyl, $C_{1-4}$alkylsulfonyl, aminosulfonyl, carbamoyl$C_{1-4}$alkyl, N-($C_{1-4}$alkyl) carbamoyl$C_{1-4}$alkyl, N-(di$C_{1-4}$alkyl)carbamoyl-$C_{1-4}$alkyl, hydroxy$C_{1-4}$alkyl and $C_{1-4}$alkoxy$C_{1-4}$alkyl;
r is 0–3;
$R^4$ is selected from at least one of hydrogen or $C_{1-4}$alkyl; $R^5$ is hydrogen, $C_{1-4}$alkyl or aryl$C_{1-4}$alkyl; $R^6$ is hydrogen, $C_{1-4}$alkyl, hydroxy$C_{1-4}$alkyl, aryl$C_{1-4}$alkyl, sulfanyl$C_{1-4}$alkyl, amino$C_{1-4}$alkyl, or $C_{1-4}$alkylamino$C_{1-4}$alkyl;
p is 0–3;
or a pharmaceutically acceptable salt, prodrug or solvate thereof.

2. A compound according to claim 1 wherein A is phenyl.
3. A compound according to either claim 1 or claim 2 wherein T is of the formula (1) or (2) and $R^5$ and $R^6$ are as defined in claim 1.
4. A compound according to claim 1 wherein B is thiazolyl or phenyl.
5. A compound according to claim 1 wherein >C(X)—CH(Y)— is >C=CH—.
6. A compound according to claim 1 wherein $R^2$ is phenyl, thienyl or pyridyl.
7. A compound according to claim 1 wherein $R^1$ is of the formula II.
8. A compound according to claim 1 which is:

(2S)-2-{4-[(E)-2-(4-fluorophenyl)-3-(5-methylimidazol-1-yl)-prop-1-enyl]-2-phenylbenzamido}-4-methylsulfanylbutyric acid;
(2S)-2-{4-[2-(4-fluorophenyl)-3-(5-methylimidazol-1-yl)-propyl]-2-phenyl-benzamido}-4-methylsulfanylbutyric acid;
(2S)-2-{3-[(E)-2-(4-fluorophenyl)-3-(imidazol-1-yl)-prop-1-enyl]-benzamido}-4-methylsulfanylbutyric acid;
(2S)-2-{4-[(Z)-3-(imidazol-1-yl)-2-(thiazol-2-yl)-prop-1-enyl]-2-phenyl-benzamido}-4-methylsulfanylbutyric acid;
(2S)-2-{3-[(E)-2-(4-fluorophenyl)-3-(imidazol-1-yl)-prop-1-enyl]-benzamido}-4-carbamoylbutyric acid;
(2S)-2-{3-[(E)-2-(4-fluorophenyl)-3-(imidazol-1-yl)-prop-1-enyl]-benzamido}-4-methylsulfanyl-N-(trifluoromethylsulfonyl)-butanamide;
(2S)-2-{3-[(Z)-2-(4-fluorophenyl)-4-(imidazol-1-yl)-but-1-enyl]-benzamido}-4-methylsulfanylbutyric acid;

(2S)-2-{3-[(E)-2-(4-fluorophenyl)-3-(imidazol-1-yl)-prop-1-enyl]-benzamido}-4-hydroxybutyric acid;

(2S)-2-{3-[(Z)-2-(4-fluorophenyl)-3-(imidazol-1-yl)-prop-1-enyl]-benzamido}-4-methylsulfanylbutyric acid;

(2S)-2-{3-[(E)-2-(4-fluorophenyl)-3-(imidazol-1-yl)-prop-1-enyl]-benzamido}-4-methylsulfonylbutyric acid;

(2S)-2-{4-[(E)-2-(4-fluorophenyl)-3-(5-methylimidazol-1-yl)-prop-1-enyl]-2-phenylbenzamido}-4-carbamoylbutyric acid;

(2S)-2-{3-[(Z)-3-(imidazol-1-yl)-2-(thiazol-2-yl)-prop-1-enyl]-benzamido}-4-carbamoylbutyric acid;

(2S)-2-{3-[(E)-2-(4-fluorophenyl)-3-(5-methylimidazol-1-yl)-prop-1-enyl]-benzamido}-4-methylsulfanylbutyric acid;

(2S)-2-{3-[(Z)-3-(imidazol-1-yl)-2-(thiazol-2-yl)-prop-1-enyl]-benzamido}-4-methylsulfanylbutyric acid;

methyl (2S)-2-{3-[(E)-2-(4-fluorophenyl)-3-(imidazol-1-yl)-prop-1-enyl]-benzamido}-4-methylsulfanylbutanoate;

tert-butyl (2S)-2-{3-[(E)-2-(4-fluorophenyl)-3-(imidazol-1-yl)-prop-1-enyl]-benzamido}-4-carbamoylbutanoate;

(2S)-2-{4-[(Z)-3-(imidazol-1-yl)-2-(thiazol-2-yl)-prop-1-enyl]-2-phenyl-benzamido}-4-carbamoylbutyric acid;

(2S)-2-{3-[(E)-2-(4-fluorophenyl)-4-(imidazol-1-yl)-but-1-enyl]-benzamido}-4-methylsulfanylbutyric acid;

(2S)-2-{4-[(E)-2-(4-fluorophenyl)-3-(imidazol-1-yl)-prop-1-enyl]-benzamido}-4-carbamoylbutyric acid;

methyl (2S)-2-{4-[(E)-2-(4-fluorophenyl)-3-(5-methylimidazol-1-yl)-prop-1-enyl]-2-phenylbenzamido}-4-methylsulfanylbutanoate;

(2S)-2-{4-[(E)-2-(4-fluorophenyl)-3-(imidazol-1-yl)prop-1-enyl]-2-phenyl-benzamido}-4-methylsulfanylbutyric acid;

methyl (2S)-2-{4-[(E)-2-(4-fluorophenyl)-3-(imidazol-1-yl)prop-1-enyl]-2-phenyl-benzamido}-4-methylsulfanylbutyrate;

(2S)-2-{4-[(E)-2-(4-fluorophenyl)-3-(imidazol-1-yl)prop-1-enyl]-2-(4-fluorophenyl)benzamido}-4-methylsulfanylbutyric acid;

methyl (2S)-2-{4-[(E)-2-(4-fluorophenyl)-3-(imidazol-1-yl)prop-1-enyl]-2-(4-fluorophenyl)benzamido}-4-methylsulfanylbutyrate;

t-butyl (2S)-2-{4-[(E)-2-(4-fluorophenyl)-3-(imidazol-1-yl)prop-1-enyl]-2-(4-fluorophenyl)-benzamido}-4-methylsulfanylbutyrate;

(2S)-2-{4-[(E)-2-(4-fluorophenyl)-3-(imidazol-1-yl)prop-1-enyl]-2-(4-fluorophenyl)-benzamido}-4-methylsulfonylbutyric acid;

methyl (2S)-2-{4-[(E)-2-(4-fluorophenyl)-3-(imidazol-1-yl)prop-1-enyl]-2-(4-fluorophenyl)benzamido}-4-methylsulfonylbutyrate;

t-butyl(2S)-2-{4-[(E)-2-(4-fluorophenyl)-3-(imidazol-1-yl)prop-1-enyl]-2-(4-fluorophenyl)benzamido}-4-methylsulfonylbutyrate;

(2S)-2-{4-[(E)-2-(4-fluorophenyl)-3-(imidazol-1-yl)prop-1-enyl]-2-(4-fluorophenyl)-benzamido}-4-methylsulfinylbutyric acid;

methyl (2S)-4-{3-[(E)-2-(4-fluorophenyl)-3-(imidazol-1-yl)prop-1-enyl]-2-(4-fluorophenyl)benzamido}-4-methylsulfinylbutyrate;

N-methylpiperidin-4-yl (2S)-2-{4-[(E)-2-(4-fluorophenyl)-3-(imidazol-1-yl)prop-1-enyl]-2-(4-fluorophenyl)benzamido}-4-methylsulfanylbutyrate;

1-(morpholin-4-yl)prop-2-yl-(2S)-2-{4-[(E)-2-(4-fluorophenyl)-3-(imidazol-1-yl)prop-1-enyl]-benzamido}-4-methylsulfanylbutyrate;

(2S)-2-{4-[(Z)-2-(thiazol-2-yl)-3-(imidazol-1-yl)prop-1-enyl]-2-(4-fluorophenyl)-benzamido}-4-methylsulfanylbutyric acid;

methyl (2S)-4-{[(Z)-2-(thiazol-2-yl)-3-(imidazol-1-yl)prop-1-enyl]-2-(4-fluorophenyl)benzamido}-4-methylsulfanylbutyrate;

tert-butyl(2S)-2-{4-[(Z)-2-(thiazol-2-yl)-3-(imidazol-1-yl)prop-1-enyl]-2-(4-fluorophenyl)benzamido}-4-methylsulfanylbutyrate;

(2S)-2-{4-[(Z)-2-(thiazol-2-yl)-3-(imidazol-1-yl)prop-1-enyl]-2-(4-fluorophenyl)-benzamido}-4-methylsulfonylbutyric acid;

methyl (2S)-2-{4-[(Z)-2-(thiazol-2-yl)-3-(imidazol-1-yl)prop-1-enyl]-2-(4-fluorophenylbenzamido}-4-methylsulfonylbutyrate;

tert-butyl (2S)-2-{4-[(Z)-2-(thiazol-2-yl)-3-(imidazol-1-yl)prop-1-enyl]-2-(4-fluorophenyl)benzamido}-4-methylsulfonylbutyrate;

N-methylpiperidin-4-yl (2S)-2-{4-[(Z)-2-(thiazol-2-yl)-3-(imidazol-1-yl)prop-1-enyl]-2-(4-fluorophenyl)benzamido}-4-methylsulfanylbutyrate;

(2S)-2-{4-[(Z)-2-(thiazol-2-yl)-3-(imidazol-1-yl)prop-1-enyl]-2-(thien-3-yl)benzamido}-4-methylsulfanylbutyric acid;

methyl (2S)-2-{4-[(Z)-2-(thiazol-2-yl)-3-(imidazol-1-yl)prop-1-enyl]-2-(thien-3-yl)benzamido}-4-methylsulfanylbutyrate;

methyl (2S)-2-{4-[(Z)-2-(thiazol-2-yl)-3-(imidazol-1-yl)prop-1-enyl]-2-(pyrid-3-yl)benzamido}-4-methylsulfanylbutyrate;

methyl (2S)-2-{4-[(Z)-2-(4-fluorophenyl)-3-(imidazol-1-yl)prop-1-enyl]-2-(pyrid-3-yl)benzamido}-4-methylsulfanylbutyric acid;

N-(3,5-dimethylisoxazol-4-ylsulfonyl (2S)-2-{4-[(Z)-2-(4-fluorophenyl)-3-(imidazol-1-yl)prop-1-enyl]-2-(4-fluorophenyl)benzamido}-4-methylsulfanylbutyramide;

N-(4-chlorophenylsulfonyl) (2S)-2-{4-[(E)-2-(4-fluorophenyl)-3-(imidazol-1-yl)prop-1-enyl]-2-(4-fluorophenyl)benzamido}-4-methylsulfanylbutyramide;

(2S)-2-{4-[(E)-2-(4-fluorophenyl)-3-(imidazol-1-yl)prop-1-enyl]-2-(4-fluorophenyl)benzamido}-4-methylsulfanylbutyric acid;

methyl(2S)-2-{4-[(E)-2-(4-fluorophenyl)-3-(imidazol-1-yl)prop-1-enyl]-2-(4-fluorophenyl)benzamido}-4-methylsulfanylbutyrate;

N-benzylsulfonyl(2S)-2-{4-[(E)-2-(4-fluorophenyl)-3-(imidazol-1-yl)prop-1-enyl]-2-(4-fluorophenyl)benzamido}-4-methylsulfanylbutyramide;

(2S)-2-{4-[(E)-2-(4-fluorophenyl)-3-(imidazol-1-yl)prop-1-enyl]-2-(4-fluorophenyl)benzamido}propanoic acid;

methyl (2S)-2-{4-[(E)-2-(4-fluorophenyl)-3-(imidazol-1-yl)prop-1-enyl]-2-(4-fluorophenyl)benzamido}-4-propanoate;

(2S)-2-{4-[(Z)-2-(thiazol-2-yl)-3-(imidazol-1-yl)prop-1-enyl]-3-phenylbenzamido}-4-methylsulfanylbutyric acid;

methyl (2S)-2-{4-[(Z)-2-(thiazol-2-yl)-3-(imidazol-1-yl)prop-1-enyl]-3-phenylbenzamido}-4-methylsulfanylbutyrate;

(2S)-2-{4-[(E)-2-(4-fluorophenyl)-3-(imidazol-1-yl)prop-1-enyl]-2-(4-fluorophenyl)benzamido}-4-methylsulfanylbutyric acid;

methyl(2S)-2-{4-[(E)-2-(4-fluorophenyl)-3-(imidazol-1-yl)prop-1-enyl]-2-(4-fluorophenyl)benzamido}-4-methylsulfanylbutyrate;

(2S)-2-{5-[(E)-2-(4-fluorophenyl)-3-(imidazol-1-yl)prop-1-enyl]-2-(2-(4-fluorophenyl)ethyl)benzamido}-4-methylsulfanylbutyric acid;

methyl (2R)-2-{3-[(E)-2-(4-fluorophenyl)-3-(imidazol-1-yl)prop-1-enyl]-benzamido}-4-methylsulfanylbutyrate;

methyl (2S)-2-{3-[(E)-2-(4-fluorophenyl)-3-(imidazol-1-yl)prop-1-enyl]-benzamido}-4-methylsulfanylbutyrate;

methyl (2S)-2-{3-[(R/S)-2-(4-fluorophenyl)-3-(imidazol-1-yl)prop-1-enyl]benzamido}-3-(thien-2-yl)propanoate methyl (2S)-2-{3-[(E)-2-(4-fluorophenyl)-3-(imidazol-1-yl)prop-1-enyl]-benzamido}-6-aminohexanoate.

(2S)-2-{3-[(E)-2-(4-fluorophenyl)-3-(imidazol-1-yl)prop-1-enyl]-benzamido}-4-methylsulfanylbutyramide;

trifluoromethanesulfonyl (2S)-2-{3-[(E)-2-(4-fluorophenyl)-3-(imidazol-1-yl)prop-1-enyl]-benzamido}-4-methylsulfanylbutyramide;

methanesulfonyl (2S)-2-{3-[(E)-2-(4-fluorophenyl)-3-(imidazol-1-yl)prop-1-enyl]-benzamido}-4-methylsulfanylbutyramide; or a pharmaceutically acceptable salt thereof.

9. A pharmaceutical composition which comprises a compound according to claim 1 and a pharmaceutically-acceptable carrier.

10. A method of treating a disease or medical condition characterized by farnesylation of ras which comprises administering to a warm-blooded animal an effective amount of a compound of the Formula I or a pharmaceutically acceptable salt thereof, as claimed in claim 1 or claim 8.

11. A compound of Formula I:

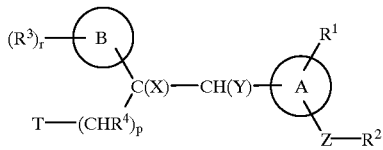

Formula I wherein
T is of the formula:

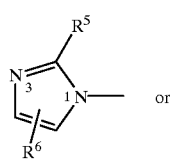

(1)

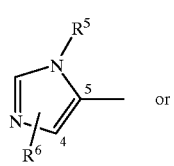

(2)

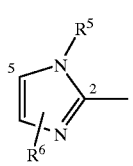

(3)

A is aryl or heteroaryl;
B is aryl or heteroaryl;

X and Y are hydrogen, or, together X and Y form a bond;
$R^1$ represents a group of the Formula II:

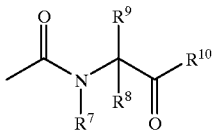

Formula II wherein $R^7$ is hydrogen or $C_{1-4}$alkyl, $R^8$ is hydrogen or $C_{1-4}$alkyl, $R^9$ is of the formula $-(CH_2)_q-R^{11}$ wherein q is 0–4 and $R^{11}$ is $C_{1-4}$alkylsulfanyl, $C_{1-4}$alkylsulfinyl, $C_{1-4}$alkylsulfonyl, hydroxy, amino, $C_{1-4}$alkoxy, carbamoyl, N-($C_{1-4}$alkyl)carbamoyl, N,N-(di$C_{1-4}$alkyl)carbamoyl, $C_{1-4}$alkyl, phenyl, thienyl, or $C_{1-4}$alkanoylamino, $R^{10}$ is hydroxy, heterocyclyl$C_{1-4}$alkoxy, heterocyclyloxy, $C_{5-7}$cycloalkyl$C_{1-4}$alkoxy, $C_{1-4}$alkoxy, amino, or $-NH-SO_2-R^{13}$ wherein $R^{13}$ represents $CF_3$, $C_{1-4}$alkyl, aryl, heteroaryl, aryl $C_{1-4}$alkyl or heteroaryl$C_{1-4}$alkyl or $R^1$ represents a lactone of Formula III:

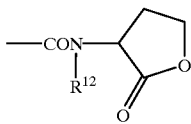

Formula III wherein $R^{12}$ is hydrogen or $C_{1-4}$alkyl;
the group of Formula II or III (having L or D configuration at the chiral alpha carbon in the corresponding free amino acid);

$R^2$ represents hydrogen, aryl or heteroaryl;

Z represents a direct bond methylene, ethylene, vinylene, oxy, $-CH_2-O-$ or $-O-CH_2-$;

$R^3$ is selected from at least one of hydrogen, $C_{1-4}$alkyl, halogen, hydroxy, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, carbamoyl, $C_{1-4}$alkoxycarbonyl, thiol, $C_{1-4}$alkysulfanyl, $C_{1-4}$alkylsylfinyl, $C_{1-4}$alkylsulfonyl, aminosulfonyl, carbamoyl$C_{1-4}$alkyl, N-($C_{1-4}$alkyl)carbamoyl$C_{1-4}$alkyl, N-(di$C_{1-4}$alkyl)carbamoyl-$C_{1-4}$alkyl, hydroxy$C_{1-4}$alkyl and $C_{1-4}$alkoxy$C_{1-4}$alkyl;
r is 0–3;

$R^4$ is selected from at least one of hydrogen or $C_{1-4}$alkyl;
$R^5$ is hydrogen, $C_{1-4}$alkyl or aryl$C_{1-4}$alkyl; $R^6$ is hydrogen, $C_{1-4}$alkyl, hydroxy$C_{1-4}$alkyl, aryl$C_{1-4}$alkyl, sulfanyl$C_{1-4}$alkyl, amino$C_{1-4}$alkyl, or $C_{1-4}$alkylamino$C_{1-4}$alkyl;

p is 0–3;

or a pharmaceutically acceptable salt, prodrug or solvate thereof.

12. A method for treatment of a disease characterized by farnesylation of mutant ras comprising administering a compound or a salt thereof, as claimed in claim 1 or claim 8.

13. A method for the treatment of a disease characterized by farnesylation comprising administering a compound or a salt thereof, as claimed in claim 11.

14. A method for the treatment of a disease characterized by farnesylation comprising administering a compound or a salt thereof, as claimed in claim 1 or claim 8.

15. The method according to claim 14 wherein the disease characterized by farnesylation is cancer.

16. The method according to claim 15 wherein the cancer is selected from carcinoma, hematpoietic tumors of lymphoid lineage, hematopoietic tumors of myeloid lineage, tumors of mesenchymal origin, melanoma, seminoma, tetratocarinoma, neuroblastoma, and glioma.

17. The method according to claim 15, wherein cancer is selected from tumors of the colon, lung, and pancreas.

18. The method according to claim 15, wherein the cancer is selected from tumors of the bladder, breast, kidney, liver, ovary, stomach, cervix, thyroid, and skin.

19. The method according to claim 16, wherein the hematopoietic tumors of lymphoid lineage are selected from acute lymphocytic leukemia, B-cell lymphoma, and Burketts lymphoma.

20. The method according to claim 16, wherein the hematopoietic tumors of myeloid lineage are selected from acute and chronic myelogenous leukemias and promyelocytic leukemia.

21. The method according to claim 16, wherein the tumors of mesenchymal origin are selected from fibrosarcoma and rhabdomyosarcoma.

22. The method according to claim 14, wherein the disease is not cancer.

23. The method according to claim 22, wherein the disease is neuro-fibromatosis.

24. The method according to claim 13 wherein the disease characterized by farnesylation is cancer.

25. The method according to claim 24 wherein the cancer is selected from carcinoma, hematpoietic tumors of lymphoid lineage, hematopoietic tumors of myeloid lineage, tumors of mesenchymal origin, melanoma, seminoma, tetratocarinoma, neuroblastoma, and glioma.

26. The method according to claim 24, wherein cancer is selected from tumors of the colon, lung, and pancreas.

27. The method according to claim 24, wherein the cancer is selected from tumors of the bladder, breast, kidney, liver, ovary, stomach, cervix, thyroid, and skin.

28. The method according to claim 25, wherein the hematopoietic tumors of lymphoid lineage are selected from acute lymphocytic leukemia, B-cell lymphoma, and Burketts lymphoma.

29. The method according to claim 25, wherein the hematopoietic tumors of myeloid lineage are selected from acute and chronic myelogenous leukemias and promyelocytic leukemia.

30. The method according to claim 25, wherein the tumors of mesenchymal origin are selected from fibrosarcoma and rhabdomyosarcoma.

31. The method according to claim 13, wherein the disease is not cancer.

32. The method according to claim 31, wherein the disease is neuro-fibromatosis.

* * * * *